United States Patent
Rooney et al.

(10) Patent No.: US 8,620,435 B2
(45) Date of Patent: Dec. 31, 2013

(54) COMBINATION THERAPY INCLUDING PERIPHERAL NERVE FIELD STIMULATION

(75) Inventors: Ethan A. Rooney, White Bear Lake, MN (US); Carl D. Wahlstrand, Lino Lakes, MN (US); Gary W. King, Fridley, MN (US); Thomas E. Cross, Jr., St. Francis, MN (US); Jeffrey S. Evanson, Minneapolis, MN (US); Kenneth T. Heruth, Edina, MN (US); Paul W. Wacnik, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2092 days.

(21) Appl. No.: 11/450,133

(22) Filed: Jun. 9, 2006

(65) Prior Publication Data

US 2007/0073356 A1     Mar. 29, 2007

Related U.S. Application Data

(63) Continuation-in-part of application No. 11/374,852, filed on Mar. 14, 2006, now Pat. No. 7,813,803, and a continuation-in-part of application No. 11/375,492, filed on Mar. 14, 2006, now Pat. No. 7,890,166, and a continuation-in-part of application No. 11/374,793, filed on Mar. 14, 2006, now Pat. No. 8,244,360.

(60) Provisional application No. 60/689,203, filed on Jun. 9, 2005, provisional application No. 60/700,627, filed on Jul. 19, 2005, provisional application No. 60/761,823, filed on Jan. 25, 2006.

(51) Int. Cl.
 *A61N 1/34* (2006.01)

(52) U.S. Cl.
 USPC .......................................................... 607/46

(58) Field of Classification Search
 USPC .......................................................... 607/46
 See application file for complete search history.

(56) References Cited

U.S. PATENT DOCUMENTS

| 3,211,151 A | 10/1965 | Foderick et al. |
| 3,385,300 A | 5/1968 | Holter |

(Continued)

FOREIGN PATENT DOCUMENTS

| WO | WO 01/89626 | 11/2001 |
| WO | WO 02/34330 | 5/2002 |

(Continued)

OTHER PUBLICATIONS

Kapural et al., "Occipital Nerve Electrical Stimulation via the Midline Approach and Subcutaneous Surgical Leads for Treatment of Severe Occipital Neuralgia: A Pilot Study," Anesthesia Analgesia 2005; 101, pp. 171-174.

(Continued)

*Primary Examiner* — Tammie K Heller
(74) *Attorney, Agent, or Firm* — Shumaker & Sieffert, P.A.

(57) ABSTRACT

Delivery of peripheral nerve field stimulation (PNFS) in combination with one or more other therapies is described. The other therapy delivered in combination with PNFS may be, for example, a different type of neurostimulation, such as spinal cord stimulation (SCS), or a drug. PNFS and the other therapy may be delivered simultaneously, in an alternating fashion, according to a schedule, and/or selectively, e.g., in response to a request received from a patient or clinician. A combination therapy that includes PNFS may be able to more completely address complex or multifocal pain than would be possible through delivery of either PNFS or other therapies alone. Further, the combination of PNFS with one or more other therapies may reduce the likelihood that neural accommodation will impair the perceived effectiveness PNFS or the other therapies.

31 Claims, 27 Drawing Sheets

(56) References Cited

U.S. PATENT DOCUMENTS

| | | | |
|---|---|---|---|
| 3,978,865 | A | 9/1976 | Trabucco |
| 4,058,128 | A | 11/1977 | Frank et al. |
| 4,142,530 | A | 3/1979 | Wittkampf |
| 4,177,818 | A | 12/1979 | De Pedro |
| 4,379,462 | A * | 4/1983 | Borkan et al. ............... 607/117 |
| 4,759,748 | A | 7/1988 | Reed |
| 5,300,110 | A | 4/1994 | Latterell et al. |
| 5,545,207 | A | 8/1996 | Smits et al. |
| 5,792,187 | A * | 8/1998 | Adams ............................ 607/46 |
| 6,038,480 | A | 3/2000 | Hrdlicka et al. |
| 6,058,331 | A | 5/2000 | King |
| 6,249,707 | B1 | 6/2001 | Kohnen et al. |
| 6,473,653 | B1 | 10/2002 | Schallhorn et al. |
| 6,517,477 | B1 | 2/2003 | Wendlandt |
| 6,735,475 | B1 | 5/2004 | Whitehurst et al. |
| 6,978,180 | B2 * | 12/2005 | Tadlock ........................ 607/46 |
| 7,010,345 | B2 | 3/2006 | Hill et al. |
| 7,120,495 | B2 | 10/2006 | Bardy et al. |
| 2002/0107553 | A1 | 8/2002 | Hill et al. |
| 2002/0143369 | A1 | 10/2002 | Hill et al. |
| 2002/0165586 | A1 | 11/2002 | Hill et al. |
| 2002/0198572 | A1 * | 12/2002 | Weiner ............................ 607/46 |
| 2003/0004549 | A1 | 1/2003 | Hill et al. |
| 2003/0078633 | A1 | 4/2003 | Firlik et al. |
| 2003/0144709 | A1 | 7/2003 | Zabara et al. |
| 2003/0212445 | A1 | 11/2003 | Weinberg |
| 2004/0015204 | A1 | 1/2004 | Whitehurst et al. |
| 2004/0059348 | A1 | 3/2004 | Geske et al. |
| 2004/0122477 | A1 | 6/2004 | Whitehurst et al. |
| 2004/0176830 | A1 | 9/2004 | Fang |
| 2004/0243205 | A1 | 12/2004 | Keravel et al. |
| 2005/0015117 | A1 | 1/2005 | Gerber |
| 2005/0070969 | A1 | 3/2005 | Gerber |
| 2005/0222628 | A1 * | 10/2005 | Krakousky ........................ 607/3 |
| 2005/0246006 | A1 | 11/2005 | Daniels |
| 2005/0256452 | A1 | 11/2005 | DeMarchi et al. |
| 2006/0030899 | A1 * | 2/2006 | O'Keeffe et al. ............... 607/46 |
| 2006/0270978 | A1 | 11/2006 | Binmoeller et al. |
| 2007/0118196 | A1 | 5/2007 | Rooney et al. |

FOREIGN PATENT DOCUMENTS

| | | |
|---|---|---|
| WO | WO 02/068042 | 9/2002 |
| WO | WO 03/026736 | 4/2003 |
| WO | WO 03/047687 | 6/2003 |
| WO | WO 2004/012812 | 2/2004 |

OTHER PUBLICATIONS

Notification of Transmittal of the International Search Report and the Written Opinion for corresponding PCT Application No. PCT/US2006/022490, dated Dec. 18, 2006 (12 pgs.).
Reply to Written Opinion for corresponding PCT Application No. PCT/US2006/022490, dated Apr. 9, 2007 (11 pgs.).
Notification of Transmittal of the International Preliminary Report on Patentability for corresponding PCT Application No. PCT/US2006/022490, dated May 21, 2007 (10 pgs.).
Notification of Transmittal of the International Search Report and the Written Opinion for PCT Application No. PCT/US2006/022565, dated Dec. 1, 2006 (12 pgs.).
Reply to Written Opinion for PCT Application No. PCT/US2006/022565, dated Apr. 9, 2007 (10 pgs.).
Notification of Transmittal of the International Preliminary Report on Patentability for PCT Application No. PCT/US2006/022565, dated Sep. 26, 2007 (10 pgs.).
U.S. Appl. No. 11/450,127, filed Jun. 9, 2006, entitled "Implantable Medical Device with Electrodes on Multiple Housing Surfaces."
U.S. Appl. No. 11/450,147, filed Jun. 9, 2006, entitled "Introducer for Therapy Delivery Elements."
U.S. Appl. No. 11/450,144, filed Jun. 9, 2006, entitled "Peripheral Nerve Field Stimulation and Spinal Cord Stimulation."
U.S. Appl. No. 11/450,148, filed Jun. 9, 2006, entitled "Implantable Medical Lead."
U.S. Appl. No. 11/374,852, filed Mar. 14, 2006, entitled "Regional Therapies for Treatment of Pain."
U.S. Appl. No. 11/375,492, filed Mar. 14, 2006, entitled "Regional Therapies for Treatment of Pain."
U.S. Appl. No. 11/374,793, filed Mar. 14, 2006, entitled "Regional Therapies for Treatment of Pain."
Office Action dated Jun. 10, 2009 for U.S. Appl. No. 11/450,144 (6 pgs.).
Responsive Amendment dated Sep. 10, 2009 for U.S. Appl. No. 11/450,144 (16 pgs.).
Responsive Amendment dated Jan. 6, 2010 for U.S. Appl. No. 11/450,127 (9 pgs.).
Office Action dated Sep. 8, 2009 for U.S. Appl. No. 11/450,148 (5 pgs.).
Office Action dated Oct. 6, 2009 for U.S. Appl. No. 11/450,127 (7 pgs.).
Responsive Amendment dated Dec. 8, 2009 for U.S. Appl. No. 11/450,148 (8 pgs.).
Response to final Office action dated Apr. 11, 2013, from U.S. Appl. No. 11/450,144, filed Jun. 11, 2013, 10 pp.
Pre-Appeal Brief Request for Review and Notice of Appeal for U.S. Appl. No. 11/450,144, filed Jul. 11, 2013, 66 pp.
Office Action from U.S. Appl. No. 11/450,144, dated Oct. 19, 2012, 15 pp.
Response to Office Action dated Oct. 19, 2012, for U.S. Appl. No. 11/450,144, filed Jan. 22, 2013, 18 pp.
Office Action from U.S. Appl. No. 11/450,144, dated Apr. 11, 2013, 14 pp.
Office Action dated Dec. 22, 2009 for U.S. Appl. No. 11/450,144 (11 pgs.).
After Final Response dated Feb. 22, 2009 for U.S. Appl. No. 11/450,144 (13 pgs.).
Request for Continued Examination and Responsive Amendment for U.S. Appl. No. 11/450,144 (23 pgs.), Dated Mar. 22, 2010.

* cited by examiner

COMBINATION THERAPY INCLUDING PERIPHERAL NERVE FIELD STIMULATION

This application claims the benefit of U.S. Provisional Application No. 60/689,203, filed Jun. 9, 2005. This application is also a continuation-in-part of each of U.S. application Ser. No. 11/374,852, filed on Mar. 14, 2006, Ser. No. 11/375,492, filed on Mar. 14, 2006, and Ser. No. 11/374,793, filed on Mar. 14, 2006, each of which claims the benefit of U.S. Provisional Application Nos. 60/700,627, filed on Jul. 19, 2005, and 60/761,823, filed on Jan. 25, 2006. The entire content of each of these applications is incorporated herein by reference.

TECHNICAL FIELD

The invention relates to medical devices, more particularly, to delivery of therapies by medical devices to treat pain.

BACKGROUND

A variety of therapies, such as neurostimulation or therapeutic agents, e.g., drugs, may be delivered to a patient to treat chronic or episodic pain. Examples of neurostimulation therapies used to treat pain are transcutaneous electrical nerve stimulation (TENS), percutaneous electrical nerve stimulation (PENS), peripheral nerve stimulation (PNS), spinal cord stimulation (SCS), deep brain stimulation (DBS) and cortical stimulation (CS). Examples of drugs used to treat pain are opioids, cannabinoids, local anesthetics, baclofen, adenosine and alpha-blockers.

PNS, SCS, DBS and CS are typically delivered by an implantable medical device (IMD). An IMD delivers neurostimulation therapy via electrodes, which are typically coupled to the IMD by one or more leads. The number and positions of the leads and electrodes is largely dependent on the type or cause of the pain, and the type of neurostimulation delivered to treat the pain. In general, an IMD delivers neurostimulation therapy in the form of electrical pulses.

SCS involves stimulating the spinal cord at specifically targeted locations, typically via leads and electrodes that are either surgically implanted post laminectomy, or inserted percutaneously in the epidural space. Delivering stimulation to the appropriate location on the spinal cord causes paresthesia that overlay the pain region to reduce the area of perceived pain. SCS can result in the patient experiencing paresthesia in a relatively large area, including more than one limb.

SCS has been shown to be effective for axial or longitudinal back pain, failed back surgery syndrome (FBBS), cervical pain, C1-C2 cervicogenic headaches, supra-orbital pain, facial pain, inguinal and pelvic pain, and chest and intercostal pain. As examples, electrodes for SCS may be implanted in the epidural space near vertebral levels T8-T10 to treat axial back pain, over the dorsal columns at vertebral levels T10-L1 to treat pain in the back, legs, ankles or feet, or over the dorsal roots, i.e., at the dorsal root entry zone, of vertebral levels L3-S1. SCS may be most effective for neuropathic pain, such as neuropathy or radiculopathy that involves a significant portion of one limb and more than one dermatome.

PNS is typically used to treat patients suffering from intractable pain associated with a single nerve. PNS places a group of electrodes in very close proximity to, e.g., in contact with, and approximately parallel to a major nerve in the subcutaneous tissue. PNS may also place a group of electrodes in very close proximity to a nerve that may be deeper in the limb. Placing electrodes in very close proximity to the nerve may ensure that only fibers within that nerve are activated at low amplitudes.

PNS electrodes may be located on percutaneous leads, but for stability and to prevent stimulation of other tissues proximate to the target peripheral nerve, PNS electrodes are generally located within insulative material that wraps around a nerve, i.e. cuff electrodes, or on one surface of a flat paddle of insulative material placed under a nerve. In any case, the electrodes for PNS are placed in close proximity to the nerve "upstream" from the source of damage or pain, e.g., closer to the spinal cord than the region of damage or pain. When electrodes are implanted upstream, the paresthesia resulting from PNS may extend to a broader area innervated by the target peripheral nerve. The most common upper extremity nerves treated with PNS are the ulnar nerve, median nerve, radial nerve, tibial nerve and common peroneal nerve.

DBS and CS can be used to treat neuropathic and nociceptive pain through delivery of stimulation to various structures of the brain. DBS may treat pain through delivery of stimulation to gray matter within the midbrain, or the thalamus, via electrodes implanted in the brain. CS may treat pain through delivery of stimulation to the sensory and/or motor cortex via electrodes placed in or on the cortex.

Therapeutic agents that treat pain may be delivered by an implantable pump, external pump, transdermally, or orally. Typically, an implantable pump delivers one or more therapeutic agents to a target location via a catheter. The target location may be intrathecal or extradural.

The pain experienced by a patient may be complex and/or multifocal. Complex or multifocal pain may include pain experienced by a patient at different locations of the body, pain attributable to different causes or pathologies, and/or pain of different types, e.g., neuropathic and/or nociceptive pain. For some patients with complex and/or multifocal pain, any one of the pain treatment modalities identified above may be unable to completely treat the experienced pain. For example, SCS may not adequately treat pain in a large number of cases, perhaps the majority, because it has been shown to help neuropathic, but not nociceptive, pain states. Nociceptive pains can come from pressure, inflammation, and temperature changes.

Further, over time, the nervous system of a patient may accommodate to a particular treatment modality. Such neural accommodation may render a previously effective modality, or dose or intensity for the modality, ineffective. Neural accommodation may result from noxious sensations being rerouted to traverse alternative pathways in the nervous system that are not affected by the accommodated modality, at least at the current dose or intensity. Simply increasing the dose or intensity of a current modality to overcome accommodation may not be effective, or may be undesirable for a variety of reasons, such as increased battery or reservoir consumption, increased side-effects, or increased likelihood of chemical dependency.

SUMMARY

In general, the invention is directed to techniques for delivering peripheral nerve field stimulation (PNFS) in combination with one or more other types of therapy, such as spinal cord stimulation (SCS). A combination therapy that includes PNFS and one or more other types of therapy may be able to more completely address complex and/or multifocal pain than would be possible through delivery of either PNFS or the other therapies alone. Further, combining PNFS with one or more other types of therapy may reduce the likelihood that neural accommodation will impair the perceived effectiveness of any of the therapies.

PNFS is electrical stimulation delivered via one or more implanted electrodes. The electrodes are positioned, i.e., implanted, in the tissue of a patient within the region where the patient experiences pain. The electrodes may be implanted within, for example, intra-dermal, deep dermal, or subcutaneous tissues of the patient. The PNFS current may spread along paths of lower resistance in any of numerous directions from electrodes, but generally spreads parallel to the skin surface. The PNFS current may spread over an area of several square centimeters. PNFS is not deliberately delivered to a specific nerve, but may excite nearly nerves.

Depending on the location at which the electrodes are implanted PNFS may be used to treat a variety of types of pain. PNFS may be particularly effective at treating localized types of pain. For example, PNFS may be used to treat pain associated with failed back surgery syndrome (FBBS) or other low back pain, cervical pain, such as in the shoulder or neck, neuralgia or other pain associated with occipital nerves, supra-orbital pain, facial pain, inguinal or other pelvic pain, intercostal or other chest pain, limb pains, phantom limb pain, visceral pain, especially if it is referred to a superficial structure, peroneal pain, or arthritis.

PNFS may ameliorate pain within the region through stimulation of axons or small nerve fibers in the nearby dermal, subcutaneous, or muscular tissues, or the tissues themselves. The stimulation of these axons or fibers may cause orthodromic action potentials that propagate toward the spinal cord, and modulate larger peripheral nerves and dorsal horn cells and/or synapses within the dermatomes that include the pain region, which may reduce pain experienced by a patient in that region. The patient may experience paresthesia in the dermatome where the electrodes are placed. The stimulation of these axons or fibers may also cause antidromic action potentials that propagate toward the skin and modulate sympathetic outflow, which may reduce pain mediated by the sympathetic system, such as with some forms of complex regional pain syndrome. The electrodes that deliver PNFS are not deliberately implanted proximate to or aligned with larger, peripheral nerves, to avoid delivery of stimulation to smaller fibers in the peripheral nerves, e.g., A-delta fibers, which may result in a patient experiencing unpleasant sensations.

By way of contrast, peripheral nerve stimulation (PNS), involves delivery of stimulation to a specific peripheral nerve via one or more electrodes implanted proximate to or in contact with a peripheral nerve, e.g., cuff electrodes surrounding the peripheral nerve. PNS may be used to deliver stimulation to, for example, the vagal nerves, cranial nerves, trigeminal nerves, ulnar nerves, median nerves, radial nerves, tibial nerves, and the common peroneal nerves. When PNS is delivered to treat pain, one or more electrodes are implanted proximate to or in contact with a specific peripheral nerve that is responsible for the pain sensation.

PNS causes orthodromic action potentials to propagate to the spinal cord via the specific peripheral nerve, diminishing pain. Typically, however, the electrodes are implanted proximate to the peripheral nerve, "upstream" from the region in which a patient perceives the pain, i.e., closer to the spinal cord than the region of pain. For PNS therapy, it is considered desirable to implant the electrodes upstream from the region in which a patient perceives pain so that the paresthesia resulting from PNS is as widely distributed as the areas innervated by the peripheral nerve, covering one or more complete dermatomes.

In some embodiments, the one or more implanted electrodes that deliver PNFS may be coupled to an implantable medical device (IMD) via one or more implanted leads. In other embodiments, the IMD may include an array of one or more electrodes formed on a surface of the IMD housing, e.g., as pad electrodes or ring electrodes, for delivery of PNFS. In such embodiments, the IMD may include a miniaturized housing with a low profile that permits dermal or subcutaneous implantation in a region in which the patient experiences pain. In either case, the IMD generates the electrical stimulation for delivery via the electrodes. In some embodiments, the IMD includes pulse generation circuitry, and delivers PNFS in the form of electrical pulses.

In some embodiments, another type of neurostimulation therapy is delivered in combination with PNFS. The PNFS and the other neurostimulation may be delivered to respective sites via respective implanted electrodes. The PNFS and other neurostimulation may be delivered with different stimulation parameters, e.g., different pulse amplitudes, pulse widths, pulse rates, or electrode polarities. In some embodiments, a single IMD may deliver both the PNFS and the other neurostimulation therapy to respective site via respective leads and sets of electrodes. In other embodiments, a plurality of IMDs may deliver respective neurostimulation therapies. In such embodiments, one or more of the IMDs may comprise a miniaturized housing with electrodes formed thereon for implantation and delivery of stimulation at a selected site, such as a region in which the patient experiences pain in the case of PNFS.

As another example, the other therapy delivered in combination with PNFS may be a drug, biological agent, genetic material, or other therapeutic agent. In such embodiments, the IMD may include a reservoir and pump to deliver the therapeutic agent. However, the other therapy delivered in combination with PNFS, whether electrical stimulation, a drug, or some other therapy, need not be delivered by the same IMD, as mentioned above, or an IMD at all. For example, the other therapy may be delivered by an external medical device, or a non-device delivery modality, such as ingestion of a drug. SCS, PNS, deep brain stimulation (DBS), cortical stimulation, and one or more drugs are examples of other therapies that may be delivered in combination with PNFS.

PNFS and the one or more other therapies may be delivered simultaneously, or in an interleaved or alternating fashion. For example, when the combined therapies include a plurality of neurostimulation therapies delivered by an IMD, the IMD may deliver pulses according to each of the therapies in an alternating or interleaved fashion, e.g., each pulse delivered according to different one of the therapies. As another example, the different neurostimulation therapies may have different pulse rates, duty cycles or scheduled times for delivery, which may result in alternating delivery of the therapies. Interleaved or alternating delivery of PNFS and one or more other therapies may, for example, reduce the likelihood that neural accommodation or tolerance to a particular drug will impair the efficacy of one or more of the therapies, while still providing therapy at any given time. Further, any or all of the combined therapies may be delivered selectively, e.g., upon request by a user, such as a patient or physician.

In one embodiment, the invention is directed to a method for treating pain of a patient that includes delivering peripheral nerve field stimulation to a region of a body of the patient in which a patient experiences pain via at least one electrode implanted in the region, and delivering at least one other therapy that treats pain to the patient in combination with the peripheral nerve field stimulation.

In another embodiment, the invention is directed to a system for treating pain of a patient that includes at least one electrode implanted in a region of a body of the patient in which a patient experiences pain, means for delivering peripheral nerve field stimulation via the at least one electrode, and means for delivering at least one other therapy that treats pain to the patient.

In another embodiment, the invention is directed to a system for treating pain of a patient that includes a first set of one or more electrodes implanted in a first region of a body of the patient in which the patient experiences pain, a second set of one or more electrodes implanted in a second region of the body of the patient, and an implantable medical device coupled to the first and second sets of electrodes that delivers peripheral nerve field stimulation via the first set of electrodes and another neurostimulation therapy via the second set of a electrodes.

In another embodiment, the invention is directed to a system for treating pain of a patient that includes a first implantable medical device that delivers peripheral nerve field stimulation to a region of a body of the patient in which the patient experiences pain, and a second medical device that deliver sat least one other therapy that treats pain to the patient.

The invention may provide advantages. For example, a combination therapy that includes PNFS and one or more other types of therapy may be able to more completely address complex or multifocal pain than would be possible through delivery of either PNFS or the other therapies alone. Pain areas involve a substantial portion of one limb, and involve more than one dermatome. SCS is often used in this case. SCS may provide paresthesia to the lower back, an entire limb, and/or portions of more than one limb. If a patient also has a focal site of pain (axial back, ribs, prior site of surgery, one knee), SCS may not ameliorate the pain, particularly if it is nociceptive pain. In such cases, PNFS may be delivered to the site of the focal pain in combination with SCS or a different therapy to more completely address the pain experienced by the patient. The PNFS might also allow strong activation of a part of a painful dermatome, even and SCS, PNS or other therapies give broader and less intense activation of that dermatome.

Further, the combination of PNFS with one or more other types of therapy may reduce the likelihood that neural accommodation will impair the perceived effectiveness of any of the therapies. Constant delivery of a therapy may lead to neural accommodation. PNFS and another therapy may be delivered at alternate times to avoid constant delivery of either therapy while providing substantially consistent relief of the pain experienced by a patient. Additionally, delivering PNSF with another therapy may allow pain to be ameliorated while avoiding problems associated with increased intensities or doses of therapies, such as increased battery or reservoir consumption, increased side-effects, or increased likelihood of chemical dependency. Also, systems according to the invention may advantageously allow patients to selectively choose delivery of one or more therapies from among a plurality of therapy modalities, including PNFS, to address their needs.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
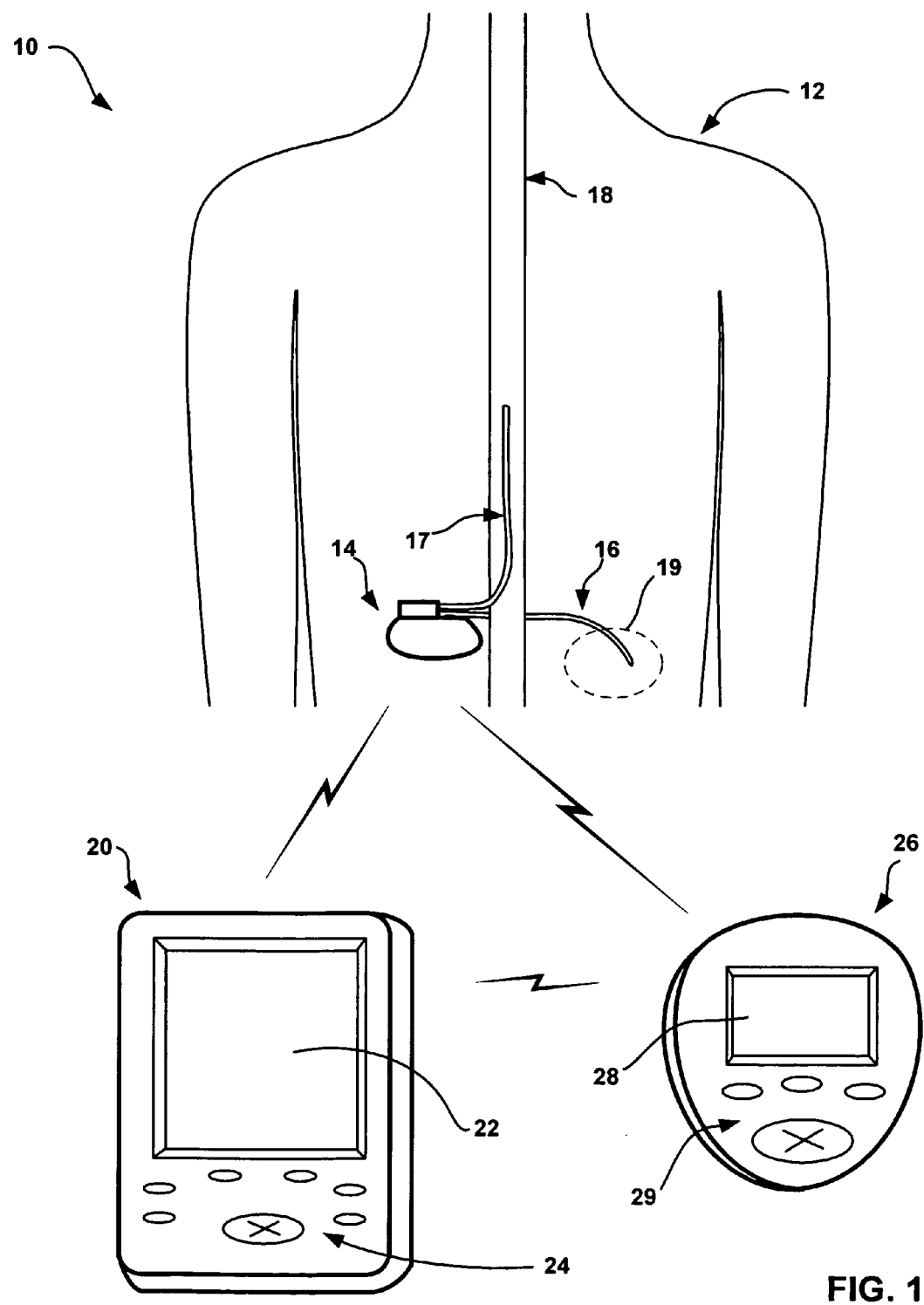
FIG. 1 is a conceptual diagram illustrating an example system for delivering peripheral nerve field stimulation (PNFS) and one or more other types of therapy to a patient in accordance with an embodiment of the invention.

FIG. 1 is a conceptual diagram illustrating an example system 10 for treating pain of a patient 12 by delivering peripheral nerve field stimulation (PNFS) in combination with one or more other types of therapy that treat pain to the patient. Through delivery of a combination therapy that includes PNFS and one or more other types of therapy, system 10 may be able to more completely address complex or multifocal pain than would be possible through delivery of either PNFS or the other therapies alone. In addition, the combination of PNFS with one or more other types of therapy may reduce the likelihood that neural accommodation or plasticity will impair the perceived effectiveness of any of the therapies.

System 10 includes an implantable medical device (IMD) 14 that delivers PNFS therapy and at least one other type of therapy to patient 12. However, the invention is not limited to embodiments in which a single IMD 14 delivers more than type of therapy, such as is illustrated in FIG. 1. In some embodiments, a separate IMD or external medical device may deliver a therapy in combination with the PNFS delivered by IMD 14. In some embodiments in which multiple medical devices deliver different therapies, the devices may communicate to coordinate delivery of the therapies, e.g., wirelessly via radio frequency or body conduction.

As mentioned above, IMD 14 may deliver another neurostimulation therapy in combination with PNFS. In the illustrated embodiment, IMD 14 delivers spinal cord stimulation (SCS) to the spinal cord 18 of patient 12 in combination with delivery of PNFS. In other embodiments, an IMD may deliver one or more of peripheral nerve stimulation (PNS), deep brain stimulation (DBS) and cortical stimulation (CS) in combination with PNFS. SCS, PNS, DBS and CS are examples of other neurostimulation therapies that may be delivered in combination with PNFS. The invention is not limited to delivery of the identified neurostimulation therapies, or any neurostimulation thearapy, in combination within PNFS. Any stimulation therapy may be delivered in combination with PNFS.

Further, the invention is not limited to embodiments in which the other therapy that treats pain is a type of stimulation. In some embodiments, for example, a drug or other therapeutic agent may be delivered in combination with PNFS. A single IMD may include circuitry to deliver PNFS, and a reservoir and pump to deliver the drug. Alternatively, systems that deliver a drug in combination with PNFS may include a separate implantable or external pump, or a transdermal delivery mechanism, such as a patch. In some embodiments, a drug is taken orally by a patient in combination with delivery of PNFS.

IMD 14 may include circuitry for the generation of electrical pulses, and deliver PNFS and other types of neurostimulation in the form of electrical pulses. IMD 14 delivers PNFS via a first set of one or more electrodes (not shown in FIG. 1) carried by a lead 16, and SCS via a second set of electrodes (not shown in FIG. 1) carried by lead 17.

Lead 16 may deliver PNFS to the tissue of patient 12 within a region 19 where patient 12 experiences pain. Lead 16 may be implanted within or between, for example, intra-dermal, deep dermal, or subcutaneous tissues of patient 12 at the region 19 where patient 12 experiences pain to deliver PNFS. These tissues include skin and associated nerves and muscles and associated nerves or muscle fibers. In the illustrated example, region 19 is an axial region of the lower back of patient 12, but the invention is not limited as such. Rather, lead 16 may be implanted in any region where patient 12 experiences pain. Lead 16 may deliver PNFS to one layer of tissue or multiple layers of a tissue as determined necessary by a physician.

For example, in other embodiments, lead 16 may extend from IMD 14 to any localized area or dermatome in which patient 12 experiences pain. For example, lead 16 may extend from IMD 14 to position electrodes at various regions of the back, the back of the head, above the eyebrow, and either over the eye or under the eye, and may be used to treat failed back surgery syndrome (FBBS), cervical pain (shoulder and neck pain), facial pain, headaches supra-orbital pain, inguinal and pelvic pain, chest and intercostal pain, mixed pain (nociceptive and neuropathic), visceral pain, neuralgia, peroneal pain, phantom limb pain, and arthritis. PNFS may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward spinal cord 18, and modulate larger peripheral nerves and dorsal horn cells and/or synapses within the dermatomes that include the pain region, which may reduce pain experienced by 12 patient in that region. The stimulation of these axons or fibers may also cause antidromic action potentials that propagate toward the skin and modulate sympathetic outflow, which may reduce pain mediated by the sympathetic system, such as with some forms of complex regional pain syndrome. Lead 16 is not implanted proximate to larger, peripheral nerves in order to avoid delivery of stimulation to smaller fibers in the nerve, e.g., A-delta fibers, which may result in a patient experiencing unpleasant sensations.

Lead 16 may comprise, as examples, a substantially cylindrical lead with ring electrodes, a paddle lead, or a lead within a more complex, three-dimensional electrode array geometry, such as a cylindrical lead with electrodes disposed at various circumferential positions around the cylinder. In some embodiments, as discussed in greater detail below, the lead may have electrodes, such as pad electrodes on more than one surface. For example, lead 16 may be a paddle-type lead with electrodes on multiple surfaces, or a multiple level lead, as will be described in greater detail below. The invention is not limited to use of any of the leads described herein, or any particular type of implantable lead.

IMD 14 may deliver another type of neurostimulation to patient 12 via lead 17 to treat pain in combination with the PNFS delivered via lead 16. In the illustrated embodiment, lead 17 extend to spinal cord 18, and IMD 14 delivers SCS via the one or more electrodes carried by lead 17. The electrodes may be implanted in, for example, an epidural space or proximal to the dorsal root entry zone of patient 12. In some embodiments, the electrodes are located within a region defined by vertebral levels T7-L1. For example, lead 17 may be implanted in the epidural space near vertebral levels T8-T10 to treat axial back pain, over the dorsal roots of L3-S1, over the dorsal columns at vertebral levels T10-L1 to treat pain in the ankle or foot, or near vertebral levels T9-T11 give paresthesia to the entire thigh. SCS may be most effective at treating neuropathic pain, such as neuropathy or radiculopathy that involves a substantial portion of one limb and more than one dermatome.

However, the invention is not limited to embodiments in which lead 17 extends to spinal cord 18, or IMD 14 delivers SCS. In other embodiments, for example, lead 17 may extend to a location closely proximate to a particular peripheral nerve responsible for causing patient 12 to experience pain, and IMD 14 may deliver PNS to the peripheral nerve. The location that the patient experiences pain may be the location that the patient perceives the pain to be. In still other embodiments, lead 17 may extend to the brain of patient 12 (not shown) via a hole formed in the cranium of the patient, and IMD 14 may deliver DBS or CS. For DBS, electrodes may be implanted within the brain, and for CS, electrodes may be implanted within or proximate to the brain.

The number and position of leads 16, 17 illustrated in FIG. 1 is exemplary. Multiple leads 16, 17 may extend to each location that receives stimulation from IMD 14. For example, four leads 16, each with two electrodes, may extend to a particular region 19 where patient 12 experiences pain, and two leads 17, each with eight electrodes may extend to spinal cord 18. Leads 16, 17 may be bifurcated, particularly if the number of interfaces that IMD 14 provides for leads 16, 17 is limited. Although not shown in FIG. 1, leads 16, 17 may be coupled to IMD 14 by one or more extensions. In some embodiments, IMD 14 may also include additional leads so as to deliver more than one other therapy in combination with PNFS.

As described herein, leads 16 and 17 may be positioned to deliver PNFS in combination with other types of therapy in order to address complex or multifocal pain. Many cases of axial pain are complex, i.e., both neuropathic (prior nerve injury) and nociceptive (ongoing stimuli). Additionally, a patient may have pain localized in a small area that is uniformly unresponsive to SCS or PNS. For example, a patient may experience arthritis pain in part of one limb, trunkal pain of post-herpetic neuralgia (PHN), or limb pain from advanced complex regional pain syndrome (CRPS) after trophic changes are irreversible. Current advanced pain management therapies for neuropathic pain, nociceptive pain, and/or axial pain may have effective treatment for a portion of the pain experienced by patient 12, but do not always relieve a patient from their pain entirely. For example, when delivering only SCS, the patient may still experience nociceptive pain since SCS only treats neuropathic pain.

As an example, patients with failed back surgery syndrome (FBBS) often have both axial pain due to pressure, instability, inflammation and nerve damage near the vertebra, and radiculopathy down one or both legs due to prior damage to nerve roots. Typically, only one modality of therapy, such as stimulation or drugs, is used since each modality has an implanted device that has its own advantages and disadvantages. Consequently, a physician may pick the modality that treats the worst pain even though pain location, nature, intensity, and other pain characteristics may change over time.

For example, SCS delivered via a set of electrodes at vertebral levels T8-T10 may be used to treat axial pain and, in some cases, may even give paresthesia into parts or all of the legs. However, such SCS stimulation often cannot give paresthesia into the feet, since fibers ascending in the dorsal columns from feet are small and possibly deep at the mid-thoracic levels. Thus, another set of electrodes may be implanted over the dorsal roots at L3-S1, or over the vertebral levels T10-L1. However, the relief of axial pain may fade over a period of time because even with delivering stimulation to different areas of the spinal cord the patient may focus on the remaining axial pain and may be relatively dissatisfied.

Furthermore, even if a patient has only axial back pain, or pain in a localized region of the trunk, using only one modality of stimulation may not be sufficient to relieve a substantial amount of the pain experienced by the patient. Moreover, SCS alone has a limitation for pain in the upper arms and neck since leads placed in the epidural space at the upper thoracic and cervical vertebral levels often move significantly relative to the spinal cord. Consequently, the level of paresthesia can change dramatically thereby preventing sleep or use during normal movements.

In addition, the nervous system has many parallel paths that communicate sensations, including pain, to the brain. Examples of such paths include the lateral spinothalamic paths, the dorsal columns (especially for visceral pain), the spinoreticular paths (for alerting), and spinocerebellar paths. When one of the paths is interrupted to diminish pain, the pain often eventually returns via another pathway.

PNFS can be used in combination with other therapies to affect different brain and spinal areas separately. In particular, delivering PNFS in combination with one or more other therapies may provide a synergistic effect by targeting different portions of the neural "circuit" thereby reducing the likelihood that neural accommodation will reduce the efficacy of one of the therapies. Thus, delivering PNFS in combination with one or more other therapies may more completely address complex pain than would be possible through delivery of either PNFS or the other therapies alone.

IMD 14 may deliver PNFS in combination with other types of therapy simultaneously, or in an interleaved or alternating fashion. For example, when the combined therapies include a plurality of neurostimulation stimulation therapies, IMD 14 may deliver electrical pulses according to each of the therapies in an alternating or interleaved fashion, e.g., each pulse delivered according to a different one of the therapies. Consequently, the delivery of each therapy can be optimized at each site.

As another example, the different electrical stimulation therapies may have different pulse rates, duty cycles, or scheduled times for delivery, which may result in alternating delivery of therapies. Thus, electrical pulses can be interleaved so as to deliver the same frequency of electrical pulses to respective sites, but with varying amplitudes or pulse widths. Alternatively, a packet of pulses may be delivered to a PNFS site, with or without ramping of amplitude from start to finish, followed by delivering another packet of pulses to, for example, a SCS site.

Interleaved or alternating delivery of PNFS and one or more other electrical stimulation therapies may, for example, reduce the likelihood that neural accommodation or plasticity will impair the efficacy of one or more of the therapies, while still providing therapy at any given time. In particular, avoiding constant stimulation at a site, PNFS or otherwise, may prevent neural accommodation that would reduce the efficacy of one or more of the therapies. Interleaved or alternating deliver of PNFS and one or more other electrical stimulation therapies may also prevent overuse or depletion of transmitters, such as GABA-B, that are major inhibitory transmitters released in the dorsal horn when electrical stimulation produces pain relief. Further any or all of the combined therapies may be delivered selectively, e.g. upon request by a user, such as a physician or a patient. In other words, system 10 may provide multiple therapies that may be selected by a user, e.g., as the pain experienced dictates, but need not deliver a plurality of therapies at all times.

System 10 also includes a clinician programmer 20. Clinician programmer 20 may, as shown in FIG. 1, be a handheld computing device. Clinician programmer 20 includes a display 22, such as a LCD or LED display, to display information relating to PNFS and one or more of the other therapies to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

A clinician or physician (not shown) may use clinician programmer 20 to program PNFS and the at least one other therapy for patient 12. In particular, the clinician may use clinician programmer 20 to select values for therapy parameters, such as pulse amplitude, pulse width, pulse rate, electrode polarity and duty cycle, for both the PNFS and the other therapy. Infusion rate, concentration, ratio (if two or more drugs are delivered), and duty cycle are examples of therapy parameters for drug delivery. IMD 14 may deliver the PNFS and the other therapy according to respective programs, each program including respective values for each of a plurality of such therapy parameters. In some embodiments, varying the pulse frequency may allow PNFS to capture target nerve fibers, such as small, medium, or large fibers sensitive to pulse frequency.

Further, IMD 14 may deliver PNFS in combination with other therapy in accordance with a program group. A program group may contain one or more programs. A program group may include one or more PNFS programs and one or more programs for the other therapy. IMD 14 may deliver stimulation pulses according to a program group by "interleaving" the pulses for each program, e.g., delivering each successive pulse according to a different one of the programs of the program group. To create a programs and program groups the clinician may select existing or predefined programs, or specify programs by selecting therapy parameter values. The clinician may test the selected or specified programs on patient 12, and receive feedback from patient 12. Highly rated programs may be provided to IMD 14 or a patient programmer, individually or as program groups, and used by IMD 14 to control delivery of stimulation. The clinician may identify preferred programs for PNFS and one or more other therapies separately or through delivery of the therapies together.

System 10 also includes a patient programmer 26, which also may, as shown in FIG. 1, be a handheld computing device. Patient programmer 26 may also include a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus or mouse.

Patient 12 may use patient programmer 26 to control the delivery of PNFS and the at least one other therapy by IMD 14. Patient 12 may use patient programmer 26 to activate or deactivate PNFS, the one or more other therapies, or both, and may use patient programmer 26 to select the programs or program group that will be used by IMD 14 to deliver PNFS in combination with one or more other types of therapy. Further, patient 12 may use patient programmer 26 to make adjustments to programs or program groups. Additionally, the clinician or patient 12 may use programmers 20, 26 to create or adjust schedules for delivery of PNFS, the one or more other therapies, or both. Such schedules may provide for alternating delivery of PNFS and the one or more other therapies.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using any telemetry techniques known in the art. Such techniques may include low frequency or radiofrequency (RF) telemetry, but other techniques are also contemplated. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

Figure 2:
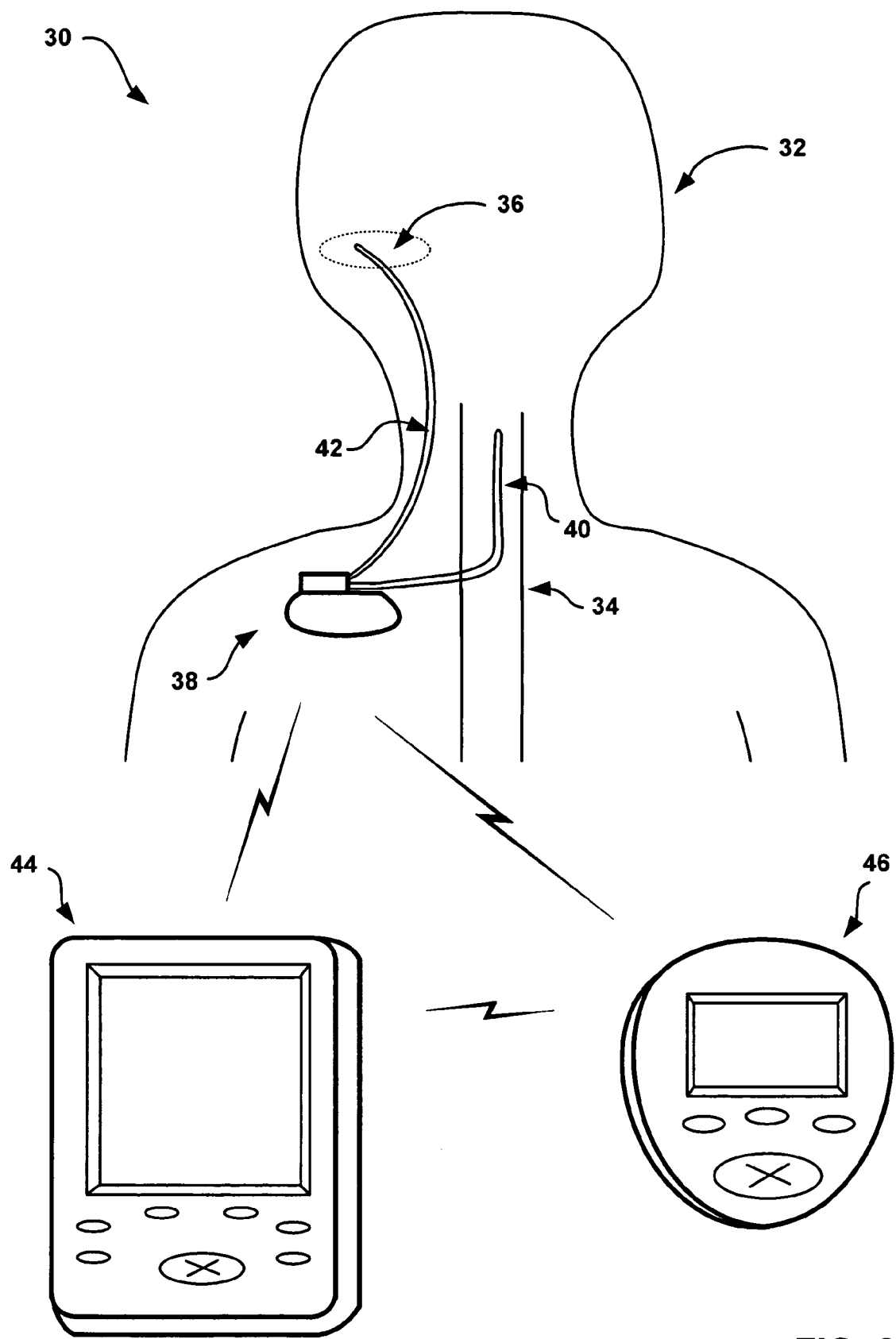
FIG. 2 is a conceptual diagram illustrating another example system for delivering PNFS and one or more other types of therapy to a patient.

FIG. 2 is a conceptual diagram illustrating another example system for delivering PNFS and one or more other types of therapy to a patient. As shown in FIG. 2, system 30 is similar to system 10; however, system 30 is utilized at a different location in patient 32. System 30 of FIG. 2 delivers PNFS in combination with SCS via IMD 38 and coupled leads 42 and 40. However, unlike system 10, system 20 delivers PNFS via lead 42 to a region 36 on the face of a patient 32 where the patient experiences pain, and SCS via lead 40 to a region at the level of the C1-C3 vertebrae of patient 32. The PNFS may, for example, alleviate supra-orbital or suborbital facial pain, while the SCS provides paresthesia to the back of the head and neck to alleviate, for example, headaches or migraines. In this manner, system 30 may more completely address a complex pain which would not be possible through delivery of PNFS of SCS alone.

System 30 includes an IMD 38 coupled to leads 42 and 40 that include electrodes, which may be substantially similar to and perform substantially similar functions as IMD 14 and leads 16 and 17 depicted and described above with reference to FIG. 1. System 30 may also include clinician and patient programmers 44 and 46, respectively, which may be substantially similar to and perform substantially similar functions as programmers 20, 26 depicted and described above with reference to FIG. 1. IMD 38 may deliver PNFS and SCS according to programs selected with one of programmers 44 or 46 and stored within a memory of IMD 38. Each stimulation program may include different therapy parameter values, and IMD 38 may deliver stimulation according to the programs in a simultaneous, interleaved, or alternating fashion, in any of the manners described above.

Figure 3:
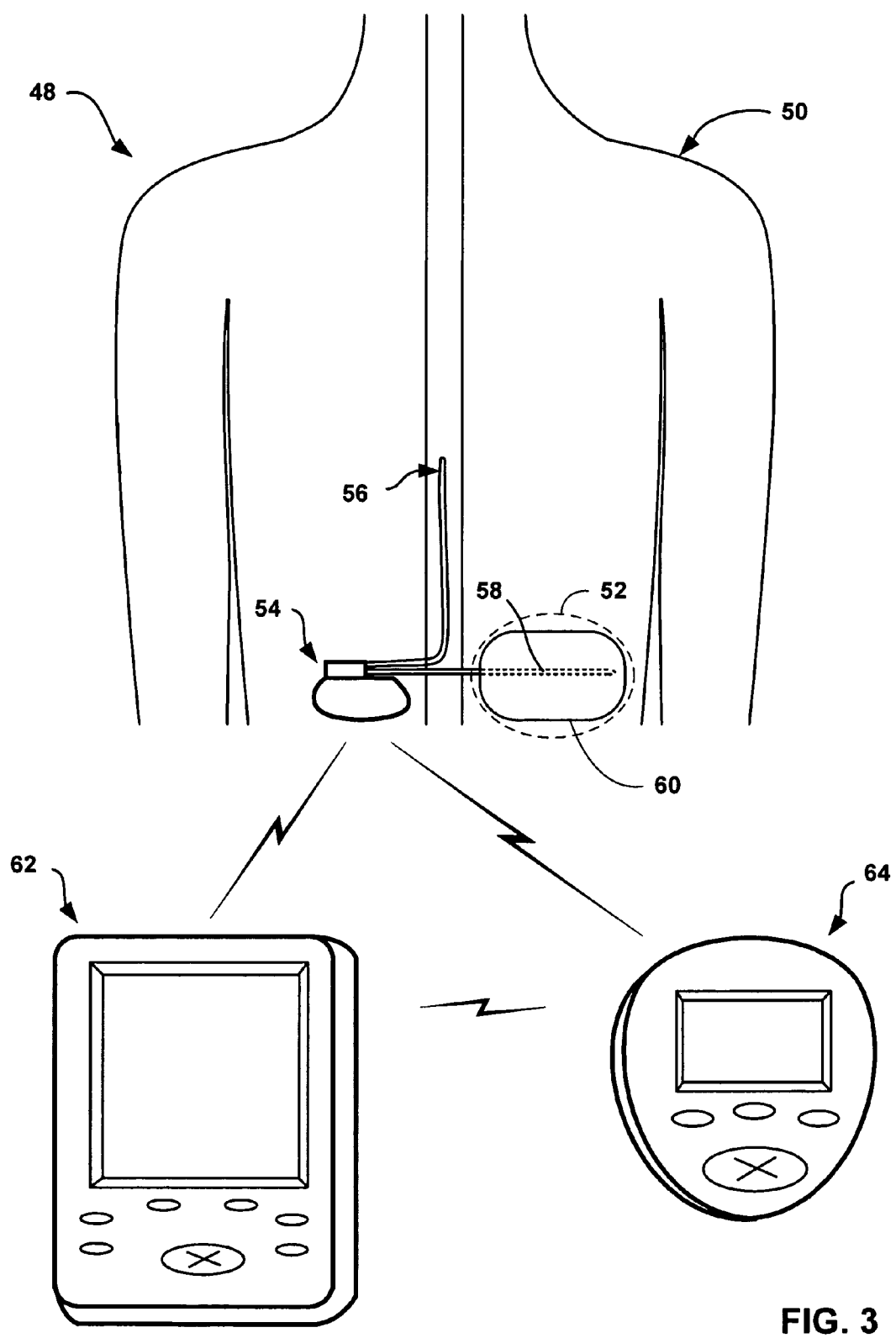
FIG. 3 is a conceptual diagram illustrating another example system for delivering PNFS and one or more other types of therapy to a patient.

FIG. 3 is a conceptual diagram illustrating another example system for delivering PNFS and one or more other types of therapy to a patient. As shown in FIG. 3, system 48 delivers PNFS to a region 52 where a patient 50 experiences pain, in combination with SCS and drug therapies. System 48 includes an IMD 54 that delivers PNFS and SCS via electrodes located on leads 58 and 56, respectively. Alternatively, separate IMDs may deliver PNFS and SCS. In such embodiments, the IMDs may communicate to coordinate therapy, e.g., wirelessly via radio frequency or electrical conduction through the body of patient 32. In the illustrated embodiment, drug therapy is also delivered to patient 50 at site 52 where pain is experienced by a patch 60 through which patient 50 transdermally absorbs a drug. Patch 60 is an example of an external medical device that delivers a therapy to patient 50.

For example, IMD 54 may deliver PNFS in combination with SCS and drug therapy in the manner illustrated by FIG. 3 for treatment of failed back surgery syndrome (FBBS) in which patient 50 experiences both axial pain and radiculopathy down one or both legs. In particular, IMD 54 may deliver PNFS at site 52 to treat axial back pain and SCS to the dorsal columns or dorsal roots of the spinal cord to treat radicular pain. Patient 50 may absorb drugs through patch 60 at site 52 to further relieve pain experienced at the site or enhance the PNFS therapy. Consequently, system 48 may more completely address complex pain than would be possible through delivery of PNFS, SCS, or drug therapy alone.

Lead 58 may be implanted in intra-dermal, deep dermal, or subcutaneous tissues of patient. In the illustrated embodiment, lead 58 extends from IMD 54 to the lower back of patient 50 to relieve pain, e.g. axial back pain, in region 52. Lead 56 may extend from IMD 54 over the dorsal roots at vertebral levels L3-S1 or over dorsal columns at vertebral levels T10-L1 to relieve radicular pain in one or both legs. IMD 54 may deliver PNFS and SCS simultaneously, or in interleaved or alternating fashion. Interleaved or alternating delivery of PNFS and SCS may reduce the likelihood that neural accommodation will impair the efficacy of the therapies while still providing one of the therapies at any given time.

In addition, patch 60 delivers drug therapy to patient 50 at region 52. Patch 60 absorbs a drug through the patch. However, the invention is not limited as such. In some embodiments drug therapy may be delivered orally, intrathecally, or extradurally. In additional embodiments, IMD 54 may also include a reservoir and drug pump to deliver the drug to region 52 or another location via a catheter. Examples of drugs that be used are opioids, cannabinoids, anti-inflammatory agents, steroids, baclofen, adenosine, local anesthesia, anti-depressants, and alpha agonists. Delivered drugs may, for example, diminish pain by their own action, especially when applied to specific sites, enhance the benefits of electrical stimulation, and treat particular pain modalities. Nociceptive pain may be treated through delivery of morphine, for example, and the action of specific nerves may be blocked through delivery of local anesthetics. Consequently, delivering PNFS in combination with drug therapy may more completely address complex pain than would be possible through the delivery of one of the other therapies alone. As one example of the synergy between therapies, PNFS delivered to region 52 by IMD 54 may reduce allodynia, thereby allowing patch 60 to be applied to the skin of patient 50 to deliver drug therapy.

System 48 includes an IMD 54 coupled to leads 58 and 56 that include electrodes, which are substantially similar to and perform substantially similar functions as IMD 14 and leads 16 and 17 depicted and described above with reference to FIG. 1. System 48 may also include clinician and patient programmers 62 and 64, respectively, which may be substantially similar to and perform substantially similar functions as programmers 20, 26 depicted and described above with reference to FIG. 1. IMD 54 may deliver PNFS and SCS according to respective programs or program groups stored within a memory of the IMD, according to different therapy parameter values, and in a simultaneous, interleaved, or alternating fashion, in any of the manners described above.

Other therapy combinations may be provided by the systems described herein. Table 1 below illustrates various combinations of PNFS therapy with other types of therapy to relieve pain associated with a number of conditions. In particular, each row of the table provides an "indication" that is treated, a location or "site" at which to deliver PNFS, reason (s) for delivering PNFS at the site, various sites at which to deliver other therapies and the reasons for delivering the other therapy types. The other types of therapy delivered in combination with PNFS include SCS, PNS, and various forms of DBS and CS. As used in Table 1, the acronyms PVG and PAG refer to midbrain gray matter stimulation locations, and the acronyms VPL and VPM refer to thalamic stimulation location. More particularly, PVG, PAG, VPL and VPM respectively refer to a periventricular gray, periaqueductal gray, ventroposterior lateral nucleus and ventroposterior medial nucleus stimulation locations.

For example, PNFS may be delivered in combination with SCS, PNS, DBS and/or CS to treat axial back pain. In this case, approximately one to four leads having approximately four to sixty-four electrodes may be implanted in the intra-dermal, deep-dermal, or subcutaneous tissue at region where the patient experiences pain. SCS may be delivered to the T7-T10 vertebral levels in combination with PNFS to give paresthesia into the back. PNS may be delivered to a branch of the median nerve in combination with PNFS to treat facet pain that the patient may experience in addition to the axial back pain. DBS may be delivered to PVG, PAG, or VPL locations in combination with PNFS to treat neuropathic components of the pain. CS may also be delivered to the motor cortex, near the midline in combination with PNFS to treat neuropathic components.

As another example, PNFS may be delivered in combination with SCS, DBS and/or CS to treat occipital neuralgia and headaches. In this case, electrode groups for PNFS may be implanted in a line transverse to the C2 and C3 nerve branches. Fascia, muscle, or tendons may be between the groups of electrodes and the nerves in order reduce the likelihood of unpleasant stimulation. SCS may be delivered to the C1-C3 nerves in combination with PNFS to give paresthesia into the back. DBS may be delivered to PVG, PAG, or VPM locations in combination with PNFS to treat neuropathic components of the pain, or triggers of the migraines. CS may be delivered to the lateral part of the motor cortex in combination with PNFS to also treat neuropathic components or triggers.

In another example, PNFS may be delivered in combination with PNS, DBS and/or CS to treat temporomandibular join pain. In this case, electrodes for PNFS may be implanted in front of the ear to deliver stimulation to or near the region where the patient experiences pain. PNS may be delivered to branches of the trigeminal nerve (V), including delivering PNS in the Gasserian ganglia foramen, in combination with PNFS to relieve neuropathic pain. DBS may be delivered to PVG, PAG, or VPM locations in combination with PNFS to give paresthesia into the face of the patient. CS may be delivered to the lateral part of the motor cortex in combination with PNFS to treat neuropathic components of the pain.

A common patient problem for stimulation therapies today is a combination of axial/back pain and radiculopathy, which is often a form of failed back surgery syndrome (FBBS). In a further example, PNFS may be delivered in combination with SCS, PNS, DBS and/or CS to treat FBBS. SCS can work very well for the radiculopathy, especially for the lower limbs, but its success for the axial pain can be less, especially after six or more months. In this case, PNFS in the painful areas of the back can help the axial pain, and the SCS part of the combined system can deal well with the radicular symptoms.

The following combination of therapies may provide relief from axial pain and radiculopathy associated with FBBS. In this case, approximately one to four electrode leads having approximately four to sixty-four electrodes may be implanted in intra-dermal, deep-dermal, or subcutaneous tissue in a region where the patient experiences pain for delivery of PNFS. SCS may be delivered to the T7-T11 vertebral levels as well as the T10-L1 vertebral levels in combination with PNFS to give paresthesia into the back, leg, and/or foot. DBS may be delivered to PVG, PAG, or VPL locations in combination with PNFS to treat neuropathic components of the pain. CS may be delivered near the midline of the motor cortex in combination with PNFS to treat neuropathic components or triggers.

In yet another example, PNFS may be delivered in combination with SCS, DBS and/or CS to treat supra-orbital or sub-orbital facial pain. In this case, electrode groups for PNFS may be implanted in a line above or below the eye, e.g., roughly parallel to the eyebrow, to deliver stimulation to branches of the facial nerve (VIII). In this case, SCS may be delivered to the C1-C3 nerves in combination with PNFS to give paresthesia into the back of the head and neck. DBS may be delivered to PVG, PAG, or VPM locations in combination with PNFS to treat neuropathic components or triggers. CS may be delivered to the lateral part of the motor cortex in combination with PNFS to treat neuropathic components or triggers.

In a further example, PNFS may be delivered in combination with SCS, PNS, DBS and/or CS to treat arthritis. In this case, electrode groups may be implanted in intra-dermal, deep-dermal, or subcutaneous tissue in any region where the patient experiences arthritis pain. SCS may be delivered to the C4-C8 vertebral levels for upper limb pain and to the T10-L1 vertebral levels for hip, knee, ankle and foot pain in combination with PNFS to give paresthesia into the painful area. PNS may be delivered to an appropriate major arm or leg nerve in combination with PNFS to give paresethesia into the painful area. DBS may be delivered to PVG, PAG, or VPL locations in combination with PNFS to treat neuropathic components or triggers. CS may be delivered near the midline of the motor cortex in combination with PNFS to treat neuropathic components in the leg and feet. CS may also be delivered near the lateral part of the motor cortex in combination with PNFS to treat neuropathic components in the arm and hand.

In another example, PNFS may be delivered in combination with SCS, PNS, DBS and/or CS to treat inguinal pain. In this case, electrode groups may be implanted in intra-dermal, deep-dermal, or subcutaneous tissue in any region where the patient experiences pain to give nonpainful PNFS stimulation to the painful area. SCS may be delivered to the T4-L1 vertebral levels in combination with PNFS to give paresthesia into the painful area. PNS may be delivered via electrodes implanted deeper along the nerves involved in the pain in combination with PNFS to give paresthesia into the painful area. DBS may be delivered to PVG, PAG, or VPL locations in combination with PNFS to treat neuropathic components or triggers. CS may be delivered near the midline of the motor cortex in combination with PNFS to treat neuropathic components in the leg and feet.

In another example, PNFS may be delivered in combination with SCS, PNS, DBS and/or CS to treat arthritis. In this case, electrode groups may be implanted in intra-dermal, deep-dermal, or subcutaneous tissue in any region where the patient experiences pain to give nonpainful PNFS stimulation to the painful area. SCS may be delivered to the T8-L1 vertebral levels in combination with PNFS to give paresthesia into the painful area. PNS may be delivered to the pudendal nerve in combination with PNFS to treat neuropathic components. DBS may be delivered to PVG, PAG, or VPL locations in combination with PNFS to treat neuropathic components or triggers. CS may be delivered near the midline of the motor cortex in combination with PNFS to treat neuropathic components in the lower body.

In another example, PNFS may be delivered in combination with SCS, PNS, DBS and/or CS to treat angina, or pain associated with other heart dysfunction, such as arrhythmia. In this case, electrodes may be implanted over the heart, any part of the thorax or at any region where the patient experiences pain, such as in the arms, jaw, or back. For example, electrodes may be implanted within or between intra-dermal, deep dermal, or subcutaneous tissues of the chest. Delivering PNFS in this manner may reduce angina attacks. A two-sided paddle for PNFS would be especially useful to deliver different parameters of stimulation to the cutaneous areas and their nerves versus the underlying muscle and its nerves. SCS may be delivered to the C1-T4 vertebral levels in combination with PNFS to give paresthesia into the painful area and reduce angina. PNS may be delivered to the vagus nerve in combination with PNFS to slow the heart and, thus, reduce stress on the heart. PNS might also be delivered to any of the major nerves in the arm, especially those which may have referred pain from cardiac nociception. DBS may be delivered to PVG, PAG, or VPL locations in combination with PNFS to treat neuropathic components. DBS may also be delivered to nuclei near the hypothalamus or in the ventral lateral medulla in combination with PNFS to lower blood pressure, which may reduce pain by reducing the stress on the heart. CS may be delivered several centimeters off the midline of the motor cortex in combination with PNFS to treat neuropathic components.

In yet another example, PNFS may be delivered in combination with SCS, PNS, DBS and/or CS to treat cancer pain or phantom limb pain. In this case, electrode groups may be implanted in intra-dermal, deep-dermal, or subcutaneous tissue in a region where the patient experiences pain to give non-painful stimulation to the painful region. SCS may be delivered at a level appropriate to the pain experienced by the patient in combination with PNFS to give paresthesia into the painful area. PNS may be delivered to a nerve involved in the pain in combination with PNFS to treat neuropathic components of the pain. DBS may be delivered to PVG, PAG, VPL, or VPM locations in combination with PNFS to treat neuropathic components or triggers. CS may be delivered at an appropriate location of the motor cortex in combination with PNFS to treat neuropathic components of the pain.

TABLE 1

| Indication | Site for PNFS | Reason for Delivering PNFS | Site for other Therapy | Reason for Delivering Other Therapy |
|---|---|---|---|---|
| Axial back pain | Axial back, 1-4 leads, 4-64 electrodes | Deliver stimulation to the region where patient experiences pain | SCS: T7-T10 | Gives paresthesia into the back |
| | | | PNS: branch of median nerve | Also treat facet pain |
| | | | DBS: PVG or PAG | Treat nociceptive components |
| | | | DBS: VPL | Treat neuropathic components |
| | | | CS: motor cortex, near midline | Treat neuropathic components |
| Occipital neuralgia, headaches | Electrode groups in a line transverse to the C2 and C3 nerve branches | Deliver stimulation to the C2 and C3 nerves to prophylactically prevent migraines and headaches | SCS: C1-C3 | Gives paresthesia into the back |
| | | | DBS: PVG or PAG | Treat nociceptive components |
| | | | DBS: VPM | Treat neuropathic components or triggers |
| | | | CS: motor cortex, lateral part | Treat neuropathic componenets or triggers |
| Temporomandibular joint pain | In front of ear | Deliver stimulation to or near the pain site. May be desirable to avoid nerves in lower jaw | PNS: branches of the trigeminal nerve (V), including in the Gasserian ganglia foramen | Relieve neuropathic pain |
| | | | DBS: PVG or PAG | Treat nociceptive components |
| | | | DBS: VPM | Gives paresthesia into the face |
| | | | CS: motor cortex, lateral part | Treat neuropathic components |
| Failed back surgery syndrome (axial pain and radiculopathy) | Axial back, 1-4 leads, 4-64 electrodes | Deliver stimulation where the patient experiences pain | SCS: T7-L1 | Gives paresthesia into the back and leg and/or foot |
| | | | PNS: Branch of median nerve or along nerves in leg | Also treat facet join pain an neuropathies in the nerves in the leg |
| | | | DBS: PNG or PAG | Treat nociceptive components |
| | | | DBS: VPL | Treat neuropathic components |
| | | | CS: motor cortex, near midline | Treat neuropathic components |
| Supra-orbital or sub-orbital facial pain | Electrode groups in a line above or below the eye, roughly parallel to the eyebrow | Deliver stimulation to branches of the facial nerve (VIII) | SCS: C1-C3 | Gives paresthesia into the back of the head and neck |
| | | | DBS: PVG or PAG | Treat nociceptive components |
| | | | DBS: VPM | Treat neuropathic components |
| | | | CS: motor | Treat |

TABLE 1-continued

| Indication | Site for PNFS | Reason for Delivering PNFS | Site for other Therapy | Reason for Delivering Other Therapy |
|---|---|---|---|---|
| Arthritis | Place electrodes in skin with the same dermatome as the painful area | Give nonpainful stimulation to the same nerves as those involved in pain | cortex, lateral part | neuropathic components |
| | | | SCS: C4-C8 for upper limb pain; T1-L1 for hip, knee, ankle or foot pain | Gives paresthesia into the painful area which may lessen pain |
| | | | PNS: of the major arm or leg nerves | Gives paresthesia into the painful area which may lessen pain |
| | | | DBS: PVG or PAG | Treat nociceptive components |
| | | | DBS: VPL | Treat neuropathic components |
| | | | CS: motor cortex, near midline for leg and feet | Treat neuropathic components |
| Pelvic pain, and or visceral organ pain | Place electrodes in skin areas over any painful area | Give nonpainful stimulation to painful area | SCS: T8-L1 | Gives paresthesia into the painful area which may lessen pain |
| | | | PNS: Pudendal nerve | Treat neuropathic components |
| | | | DBS: PVG or PAG | Treat nociceptive components |
| | | | DBS: VPL | Treat neuropathic components |
| | | | CS: motor cortex, near midline for lower body | Treat neuropathic components |
| Angina, heart dysfunction, or arrhythmia | Electrodes over the heart part of the thorax or at any painful area, even in the arms, jaw, or back | Reduce angina attacks | SCS: C1-T4 | Gives paresthesia into the painful area which may lessen pain and reduce angina |
| | | | PNS: Vagus nerve, medial nerve, unlar nerve | Slows heart, reducing stress on the heart |
| | | | DBS: PVG or PAG | Treat nociceptive components |
| | | | DBS: VPL | Treat neuropathic components |
| | | | DBS: Nuclei near the hypothalamus or in the ventral lateral medulla | Lowers blood pressure |
| | | | CS: motor cortex, several centimeters off the midline | Treat neuropathic components |
| Cancer or phantom limb pain | Place electrodes in skin areas over any painful area | Give nonpainful stimulation to painful area | SCS: at a level appropriate to the pain | Gives paresthesia into the painful area which may lessen pain |
| | | | PNS: on a nerve appropriate to the pain | Treat neuropathic components |

TABLE 1-continued

| Indication | Site for PNFS | Reason for Delivering PNFS | Site for other Therapy | Reason for Delivering Other Therapy |
|---|---|---|---|---|
| | | | DBS: PVG or PAG | Treat nociceptive components |
| | | | DBS: VPL or VBM | Treat neuropathic components |
| | | | CS: motor cortex, at a site appropriate for the painful area | Treat neuropathic components |

Table 2 below illustrates various drugs, one or more of which may be delivered in combination with PNFS, either alone or in combination with any of the other stimulation modalities indicated above. Drugs can delivered in combination with PNFS may allow complex or multifocal pain to be better addressed by: diminishing pain by their own action (additive effect), especially if applied to specific sites (patches, intrathecal, epidural); augmenting or magnifying the benefits of electrical stimulation; addressing certain types or locations of pain, such as morphine for nociceptive pain, or local anesthetics to block some nerves.

TABLE 2

| Drug | Delivery Site and Mechanism | Reason for Delivering |
|---|---|---|
| Opioid | Lumbar intrathecal space Systemic (oral, IV, fentanyl patch) Subcutaneous axial back (Permeable membrane catheter) Intracerebroventricular Intraparenchymal Local peripheral administration | Treat nociceptive aspects of pain |
| δ opioid | Systemic, ICV, IP, Local peripheral administration | Synergistic with high frequency stimulation |
| μ opioid | Systemic, ICV, IP, Local peripheral administration | Synergistic with low frequency stimulation |
| Cannabinoid | Lumbar intrathecal space Systemic (oral, IV) Subcutaneous axial back (Permeable membrane catheter) Intracerebroventricular Intraparenchymal Local peripheral administration | Treat nociceptive aspects of pain |
| Local anesthetic (e.g. Bupivacaine) | Lumbar intrathecal Epidural Lumbar sympathetic chain Vertebral disc Facet joint Patch infusion into axial back subcutaneous tissue Local peripheral administration | Additive effect for neuropathic pain |
| Baclofen (GABA agonist) | Systemic Lumbar intrathecal Local peripheral administration | Potentiates neurostimulation |
| Adenosine | Systemic Lumbar intrathecal Local peripheral administration | Potentiates neurostimulation |
| α-adrenergic agonists (e.g. Clonidine) | Systemic Lumbar intrathecal Vertebral disc Facet joint Local peripheral administration | Potentiates neurostimulation Additive effect for neuropathic pain |

TABLE 2-continued

| Drug | Delivery Site and Mechanism | Reason for Delivering |
| --- | --- | --- |
| Anti-inflammatory (e.g. NSAIDS, steroids, TNFα blocker) | Systemic<br>Patch infusion into axial back SQ tissue<br>Catheter infusion into SQ tissue<br>Lumbar intrathecal<br>Lumbar epidural<br>Vertebral disc<br>Facet joint<br>Local peripheral administration | Reduce inflammation in addition to stimulation |
| Muscle relaxant | Systemic<br>Patch infusion into axial back SQ tissue<br>Catheter infusion into axial back SQ tissue<br>Local peripheral administration | Relax back muscles in addition to stimulation |
| Antidepressant | Systemic<br>ICV, IP<br>Local peripheral administration | Additive to stimulation |
| Antiepileptic (e.g. Gabapentin) | Systemic<br>ICV, IP<br>Lumbar intrathecal<br>Local peripheral administration | Additive to stimulation |

PNFS could also be used in conjunction with physical therapy, massage therapy, or chiropractic therapy. Any of these therapies may be provided with the devices and systems described herein.

Figure 4:
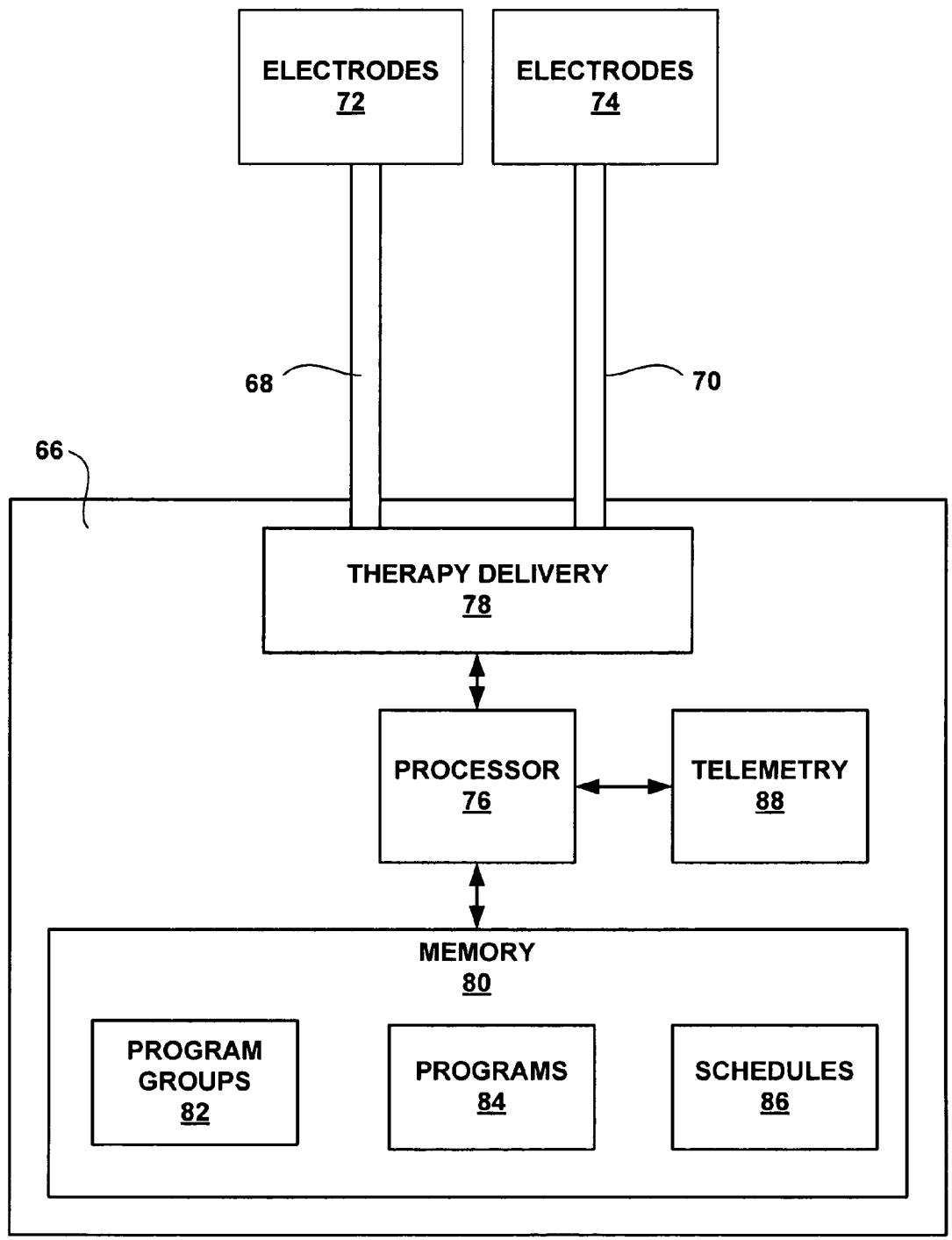
FIG. 4 is a block diagram illustrating an example implantable medical device for delivering PNFS and one or more other types of therapy to a patient.

FIG. 4 is a block diagram illustrating an example implantable medical device for delivering PNFS and one or more other types of therapy to a patient. IMD 66 may be an embodiment of any of IMDs 14, 38 or 54, whiles leads 68 and 70 may be embodiments of any leads 16 and 17, 40 and 42, and 56 and 58. As shown in FIG. 4, IMD 66 may deliver neurostimulation, such as PNFS, via electrodes 72 of lead 68 in combination with another type of stimulation, such as SCS, via and electrodes 74 of lead 70. Lead 68 may have electrodes on multiple surfaces, e.g., may be a dual sided paddle lead or a multiple level lead, as described in this disclosure. Lead 70 may be a lead as described herein or any type of known lead.

Electrodes 72 and 74 are electrically coupled to a therapy delivery module 78 via leads 68 and 70, respectively. Therapy delivery module 78 may, for example, include an output pulse generator coupled to a power source such as a battery. Therapy delivery module 78 may deliver electrical pulses to patient 12 via at least some of electrodes 72 and 74 under the control of a processor 76.

Processor 76 controls therapy delivery module 78 to deliver PNFS and another type of neurostimulation according to a selected one of program groups 82 stored in a memory 80. Specifically, processor 76 may control circuit 78 to deliver electrical pulses with the amplitudes, pulse widths, frequency, or electrode polarities specified by programs 84 of the selected program group 82, and according to the duty cycles specified by the programs. In the case of drug therapy, programs 84 may specify the amount, concentration, and rate of drug delivery. Programs 84 are also stored in memory 80.

In either case, each program group 82 may include programs 84 for peripheral neurostimulation only, another therapy only, or programs for both peripheral neurostimulation and the other therapy. Thus, processor 76 may control whether peripheral neurostimulation, another therapy, or both are delivered at any given time through selection of one of program groups 82. Similarly, a clinician or patient 12 using programmers 20 and 26, 44 and 46, or 62 and 64 to communicate with processor 76 via a telemetry module 88 may select delivery of peripheral neurostimulation, another therapy, or both through selection of one of program group 82.

Processor 76 may control therapy delivery module 78 to deliver programs 84 of a program group 82, and thus PNFS and another therapy, simultaneously. Processor 76 may control module 78 to interleave delivery of the programs 84 of the currently selected one of program groups 82 by delivering each successive stimulation pulse according to a different one of the programs. Further, the duty cycles of the respective programs 84 of the currently selected one of program groups 82 may be such that processor 76 controls therapy delivery module 78 to deliver the programs in an alternating manner.

Memory 80 may also store schedules 86. Schedules 86 may define times for processor 76 select a particular program 84 or program group 82, and control therapy delivery module 78 to deliver therapy according to that program or group. A schedule 86 may cause peripheral neurostimulation and at least one other therapy to be delivered at respective times, which may include simultaneous and/or alternate delivery. A clinician or patient may create, modify, and select schedules 86 using programmers 20 or 26, or any other programmers described herein.

Through interleaved delivery of programs 84, different duty cycles or pulse rates of programs, schedules 86, and patient selection of programs 84 or program groups 82, therapy delivery module 78 may deliver PNFS and at least one other therapy in a generally alternating fashion. For example, electrical pulses may be interleaved so as to deliver the same frequency of electrical pulses for PNFS and the other types of therapy, but with varying amplitudes or pulse widths. As another example, a packet of pulses may be delivered to provide PNFS, with or without ramping of amplitude from start to finish, followed by delivering a packet of pulses to provide one of the other types of therapy. As a result, the likelihood that neural accommodation will impair the efficacy of one or more of the therapies will be reduced, while still providing therapy at any given time. Interleaved or alternating delivery of PNFS and one or more other electrical stimulation therapies may also prevent overuse or depletion of transmitters, such as GABA-B, that are major inhibitory transmitters released in the dorsal horn when electrical stimulation produces pain relief.

In addition to program groups 82, constituent programs 84 and schedules 86, memory 80 may include program instructions that, when executed by processor 76, cause IMD 66 and processor 76 to perform the functions ascribed to IMD 66 herein. Memory 80 may include any volatile, non-volatile, magnetic, optical, or electrical media, such as a random-access memory (RAM), read-only memory (ROM), non-volatile RAM (NVRAM), electronically-erasable programmable ROM (EEPROM), flash memory, or the like. Processor 76 may include any one or more of a microprocessor, digital signal processor (DSP), application specific integrated circuit (ASIC), field-programmable gate array (FPGA), discrete logic circuitry, or the like.

IMD 66 also includes a telemetry circuit 88 that allows processor 76 to communicate with clinician programmer 20, 44, 62 and patient programmer 26, 46, 64. Processor 76 may receive programs to test on patient 12 from clinician programmer 20 via telemetry circuit 88 during programming by a clinician. Processor 76 may receive programs 84, program groups 82 and schedules 86 from clinician programmer 20 via telemetry circuit 88 during programming by a clinician, and later receive program, program group, and schedule selections or modifications made by patient 12 from patient programmer 26 via telemetry circuit 88. In embodiments in which patient programmer 26 stores the program groups, rather than memory 80 of IMD 66, processor 76 may receive programs or groups selected by patient 12 from patient programmer 26 via telemetry circuit 88.

Figure 5:
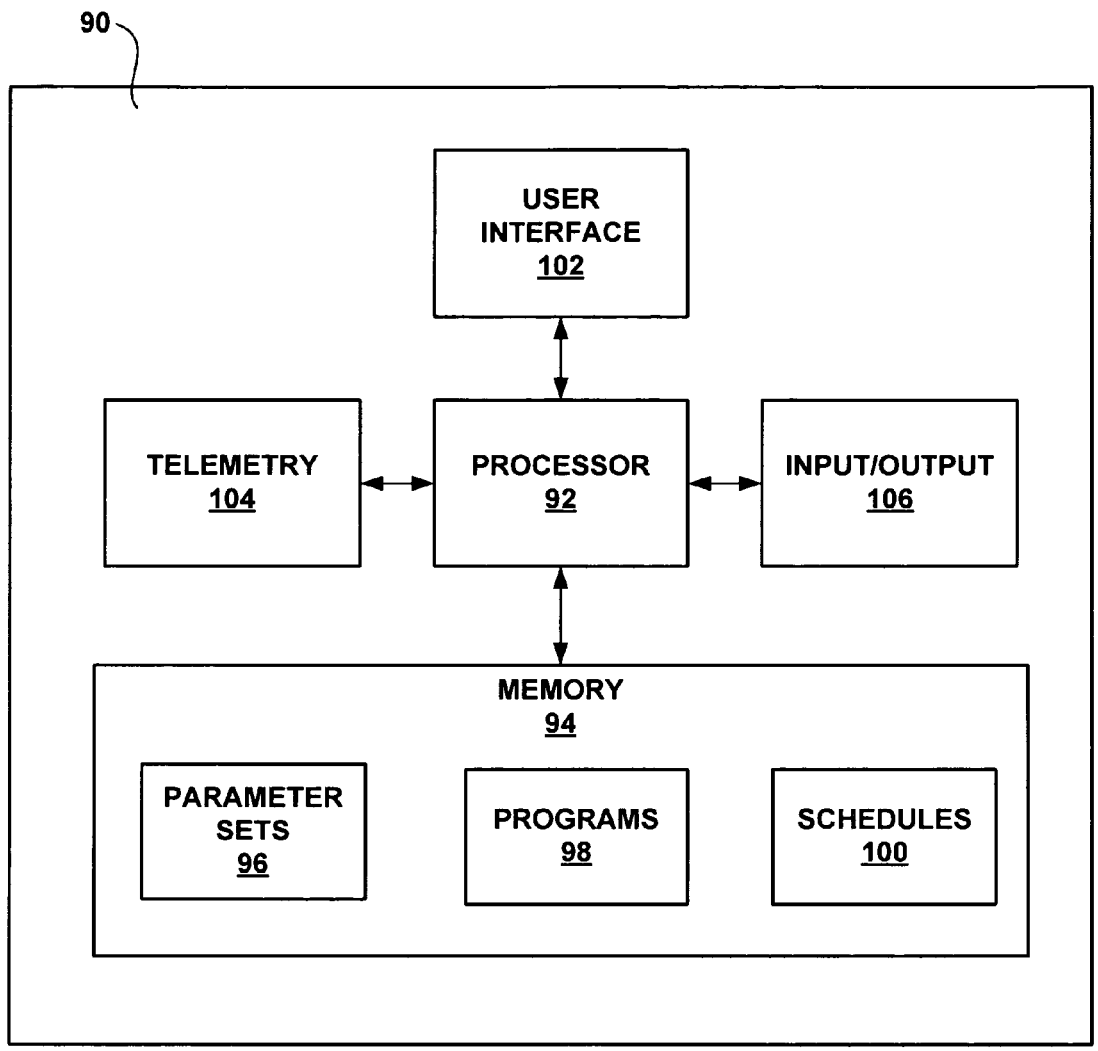
FIG. 5 is a block diagram illustrating an example clinician programmer that allows a clinician to program PNFS and one or more other types of therapy for a patient.

FIG. 5 is a block diagram illustrating an example clinician programmer that allows a clinician to program PNFS and one or more other types of therapy for a patient. As shown in FIG. 5, clinician programmer 90 is an embodiment of clinician programmers 20, 44, or 62. A clinician may interact with a processor 92 via a user interface 102 in order to program delivery of PNFS in combination with one or more other types of therapy. User interface 102 may include a display and keypad (similar to display 22 and keypad 24 of programmer 20), and may also include a touch screen or peripheral pointing devices as described above. Processor 92 may also provide a graphical user interface (GUI) to facilitate interaction with a clinician, as will be described in greater detail below. Processor 92 may include a microprocessor, a controller, a DSP, an ASIC, an FPGA, discrete logic circuitry, or the like.

Clinician programmer 90 also includes a memory 94. Memory 94 may include program instructions that, when executed by processor 92, cause clinician programmer 90 to perform the functions ascribed to clinician programmer 90 herein. Memory 94 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program delivery of PNFS and one or more types of therapy for patient 12 by specifying a program group 96 or program 98 to test on patient 12. The clinician may interact with the GUI and user interface 102 in order to specify program groups or programs. Processor 92 transmits the selected or specified programs to an IMD (such as IMD 14, 38 or 54) for delivery to patient 12 via a telemetry circuit 104. Processor 92 may transmit program groups 96 and programs 98 created by the clinician to IMD 14 via telemetry circuitry 104, or to a patient programmer (such as patient programmer 26, 46 or 64) via input/output circuitry 106. I/O circuitry 106 may include transceivers for wireless communication, appropriate ports for wired communication or communication via removable electrical media, or appropriate drives for communication via removable magnetic or optical media.

Figure 6:
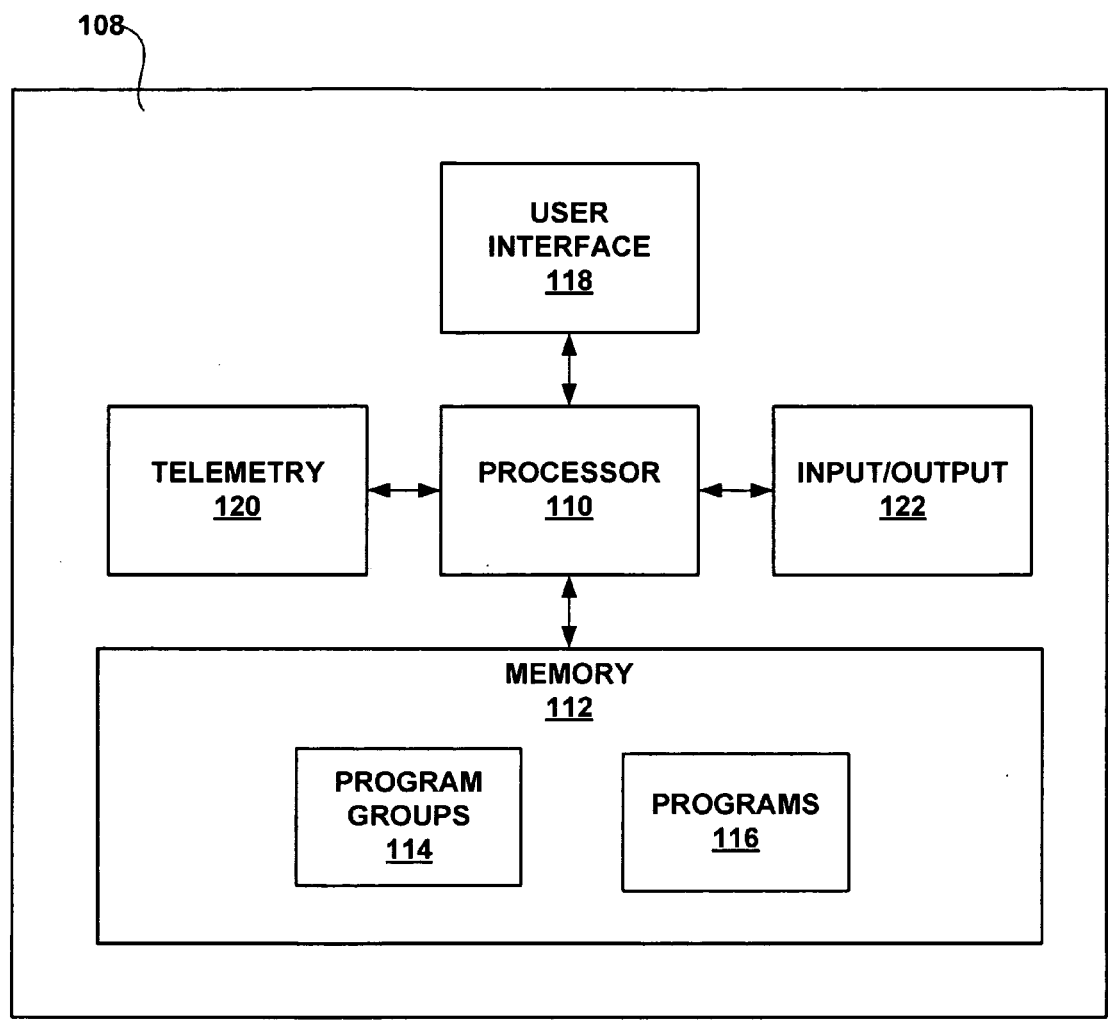
FIG. 6 is a block diagram illustrating an example patient programmer that allows a patient to control delivery of PNFS and one or more other types of therapy by an implantable medical device.

FIG. 6 is a block diagram illustrating an example patient programmer that allows a patient to control delivery of PNFS and one or more other types of therapy by an implantable medical device. As shown in FIG. 5, patient programmer 108 may be an embodiment of any patient programmers 26, 46, or 64. Patient 12 may interact with a processor 110 via a user interface 118 in order to control delivery of PNFS in combination with one or more other types of therapy. User interface 118 may include a display and a keypad (such as display 28 and keypad 30 of programmer 26), and may also include a touch screen or peripheral pointing devices as described above. Processor 110 may also provide a graphical user interface (GUI) to facilitate interaction with patient 12. Processor 110 may include a microprocessor, a controller, a DSP, an ASIC, an FPGA, discrete logic circuitry, or the like.

Patient programmer 108 also includes a memory 112. In some embodiments, memory 112 may store program groups 114 and programs 116 that are available to be selected by a patient for delivery of PNFS and one or more other types of therapy. Memory 112 may also store schedules in similar fashion as memory 80 of IMD 14 (FIG. 4). Memory 112 may also include program instructions that, when executed by processor 110, cause patient programmer 108 to perform the functions ascribed to patient programmer 108 herein. Memory 112 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Patient programmer 108 also includes a telemetry circuit 104 that allows processor 110 to communicate with an IMD 14,38,54, and input/output circuitry 106 that to allow processor 110 to communicate with clinician programmer 20,44,62. Processor 110 may receive program or program group selections made by patient 12 via user interface 118, and may either transmit the selection or the selected program or group to IMD 14 via telemetry circuitry 104 for delivery of neurostimulation therapy according to the selected program or group. Further, processor 110 may select a program groups 114 or programs 116 according to a schedule 100, and may either transmit the selection or the selected program or group to IMD 14,38,54 via telemetry circuitry 104 for delivery of neurostimulation therapy according to the selected program or group. Where patient programmer 108 stores program groups 114 and programs 116 in memory 112, processor 110 may receive program groups 114 and programs 116 from clinician programmer 20, via input/output circuitry 106 during programming by a clinician. Circuitry 106 may include transceivers for wireless communication, appropriate ports for wired communication or communication via removable electrical media, or appropriate drives for communication via removable magnetic or optical media.

Figure 7A:
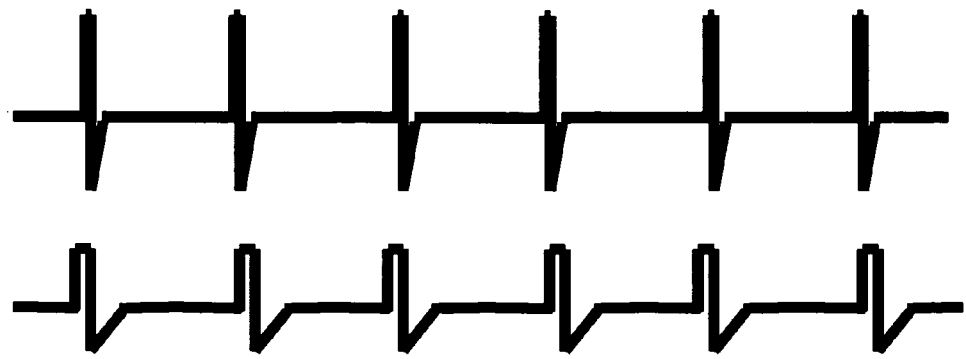
FIGS. 7A-7F are timing diagrams illustrating delivery of PNSF in combination with another neurostimulation therapy according to embodiments of the invention.
Figure 7B:
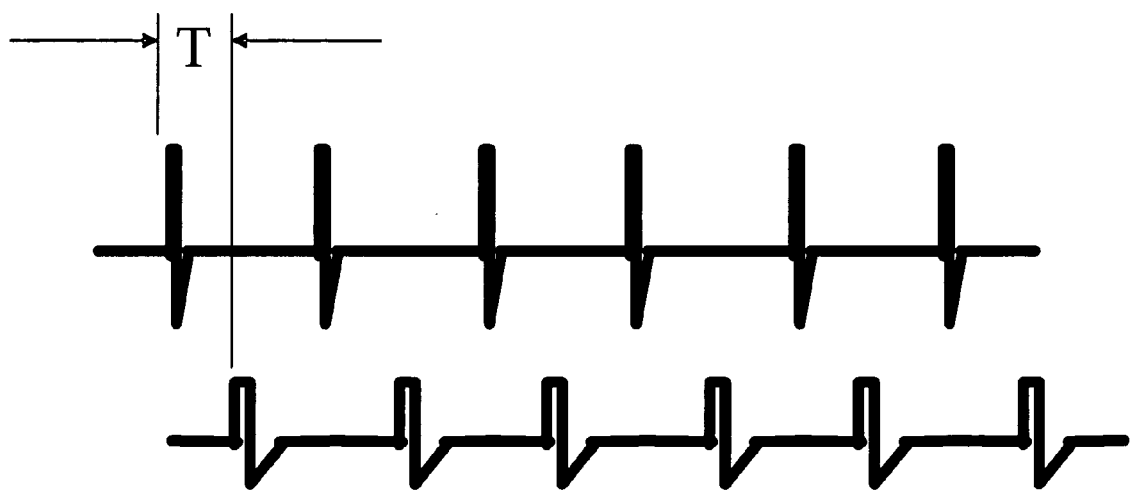
Figure 7C:
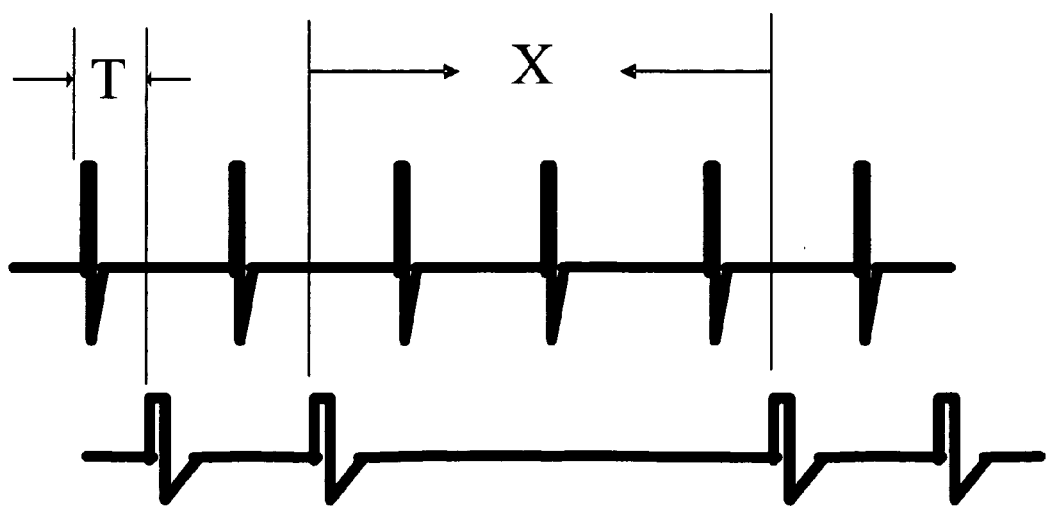
Figure 7D:
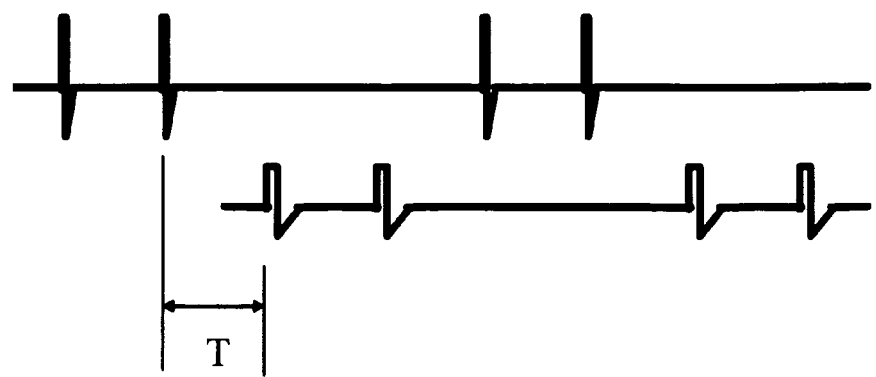
Figure 7E:
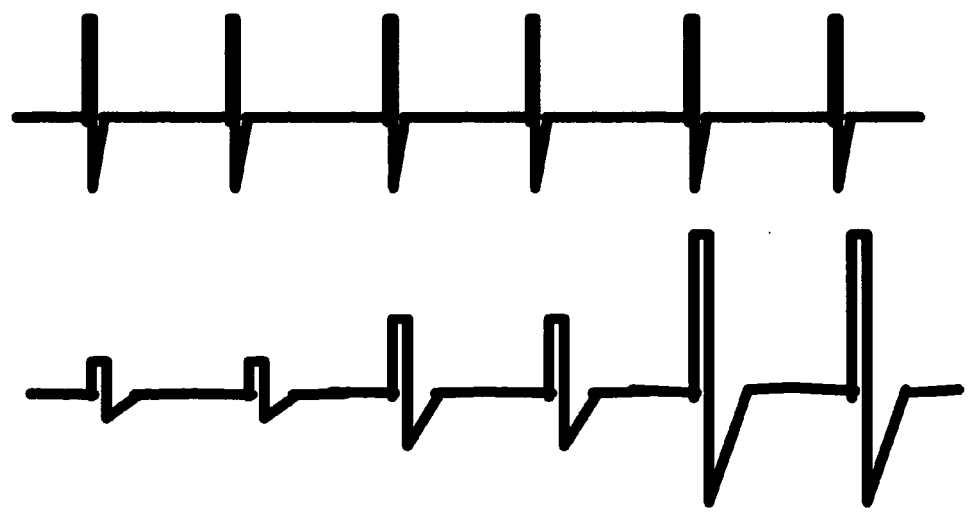
Figure 7F:
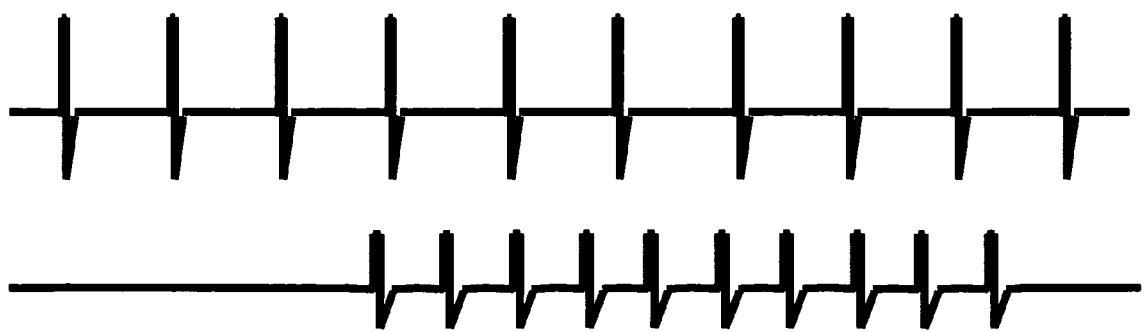

FIGS. 7A-7F are timing diagrams illustrating delivery of PNSF in combination with another neurostimulation therapy according to embodiments of the invention. FIGS. 7A-7F are timing diagrams illustrating delivery of PNSF in combination with another neurostimulation therapy according to embodiments of the invention. SCS, PNS, DBS, and CS are examples of other types of neurostimulation therapies that may be delivered in combination with PNFS. In general, IMD 14 (or other IMDs 38 or 54, IMD 14 is used as an example from here on) may deliver electrical pulses according to each of the therapies simultaneously, in an interleaved or alternating fashion, or overlapping in some degree in time. For example, each electrical stimulation therapy may have different pulse rates, duty cycles, or scheduled times for delivery, or IMD may deliver programs of a program group in an interleaved fashion, each of which may result in an alternating delivery of the therapies. In each of FIGS. 7A-7E, the bottom group of pulses represents delivery of PNFS pulses by IMD 14, and the top group of pulses represents delivery of another neurostimulation therapy, such as SCS, by the IMD. In FIG. 7F, the top group of pulses represents delivery of PNFS pulses by IMD 14, and the bottom group of pulses represents delivery of another neurostimulation therapy, such as DBS, by the IMD. Each group of pulse may represent delivery of pulses by IMD 14 according to a respective therapy program, and both groups of pulses may be included in a common program group.

FIG. 7A illustrates simultaneous delivery of PNFS and another neurostimulation therapy at a common pulse rate of 50 Hz by IMD 14. However, the PNFS and other neurostimulation are delivered with different amplitudes and pulse widths. Specifically, in the example illustrated by FIG. 7A, pulse for the other neurostimulation is delivered with a pulse amplitude and pulse width of 3 volts and 150 µs, respectively, and PNFS pulses are delivered at a pulse amplitude and pulse width of 2 volts and 300 µs, respectively.

FIG. 7B illustrates interleaved delivery of PNFS and another neurostimulation therapy by IMD 14 at the common pulse rate and different pulse amplitudes and widths illustrated by FIG. 7A. Interleaved delivery of PNFS pulses and pulses for the other neurostimulation resulting in a phase offset represented by a time T.

As was the case with FIG. 7B, FIG. 7C illustrates interleaved delivery of PNFS and another neurostimulation therapy by IMD 14 at the common pulse rate and different pulse amplitudes and widths illustrated by FIG. 7A. However, in the example illustrated by FIG. 7C, IMD 14 delivers PNFS with according to a duty cycle, rather than continuously. As a result, PNFS and the other neurostimulation are delivered for in an interleaved fashion similar to FIG. 7B for a period of time, followed by an equal period of time in which only the other neurostimulation is delivered.

FIG. 7D illustrates delivery of both PNFS and the other neurostimulation according to respective duty cycles, where the duty cycles result in alternating delivery of PNFS and the other neurostimulation.

FIG. 7E illustrates an example in which IMD 14 increases, e.g., "ramps up," the pulse amplitude of PNFS over time. In particular, FIG. 7E illustrates a pulse amplitude increase every two pulses FIG. 7F illustrates delivery of PNFS and another neurostimulation therapy by IMD according to different therapy parameters. In particular, IMD 14 delivers pulses for PNFS (top) at a frequency, amplitude, and pulse width of 40 Hz, 4.8 volts, and 400 µs, respectively, and pulse for the other neurostimulation therapy (bottom) at a frequency, amplitude, and pulse width of 240 Hz, 2 volts, and 60 µs, respectively.

FIGS. 8A-8C, 9A-9E and 10A-10D illustrate various embodiments of implantable medical leads with electrodes on multiple surfaces. Such electrodes may be used for delivery of PNFS as described herein, e.g., may be coupled to an IMD and extend from the IMD such that electrodes on the lead is located within a region in which the patient experiences pain. Such leads may allow PNFS to be delivered to a larger area, and may provide programming flexibility to a clinician for selective stimulation of various tissues or tissue layers proximate to various surfaces of the lead. The invention is not limited to the illustrated leads and, as discussed above, may be implemented using any type of lead.

Figure 8A:
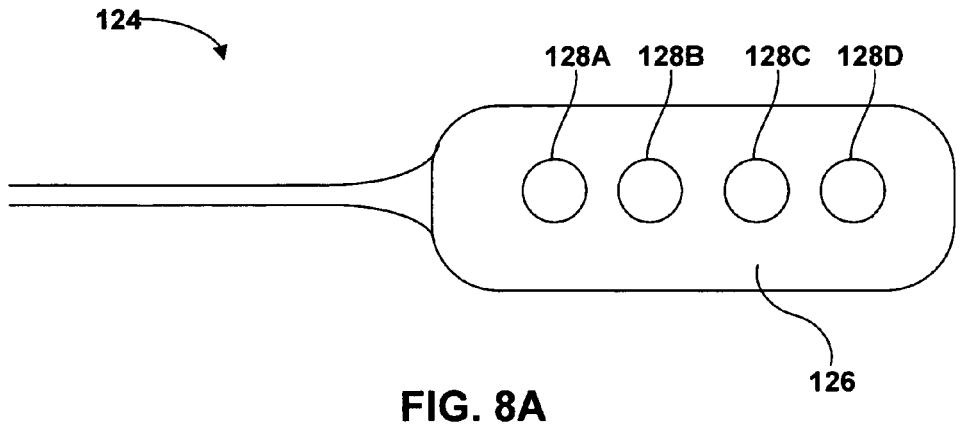
FIGS. 8A-8C are schematic diagrams illustrating a top and side views of example implantable medical leads having a plurality of electrodes located on more than one surface of the lead.
Figure 8B:
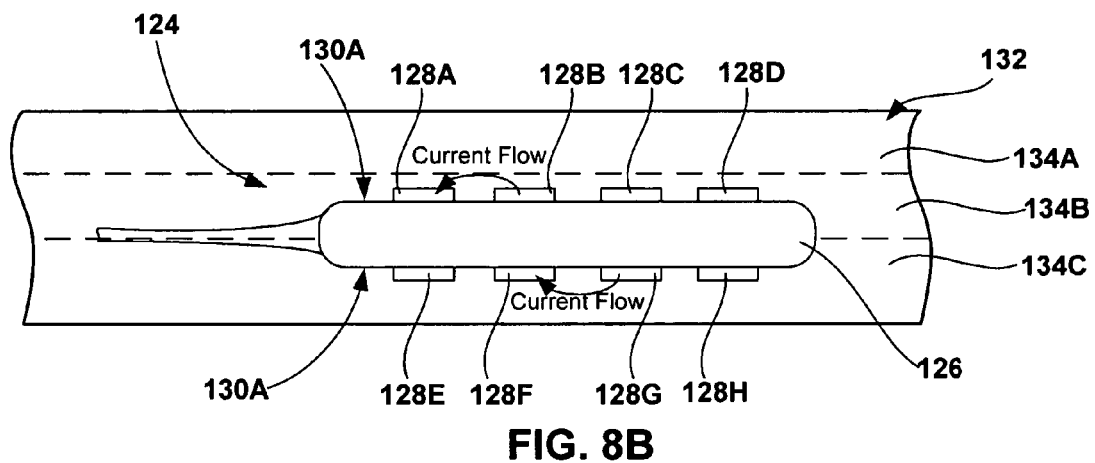
Figure 8C:
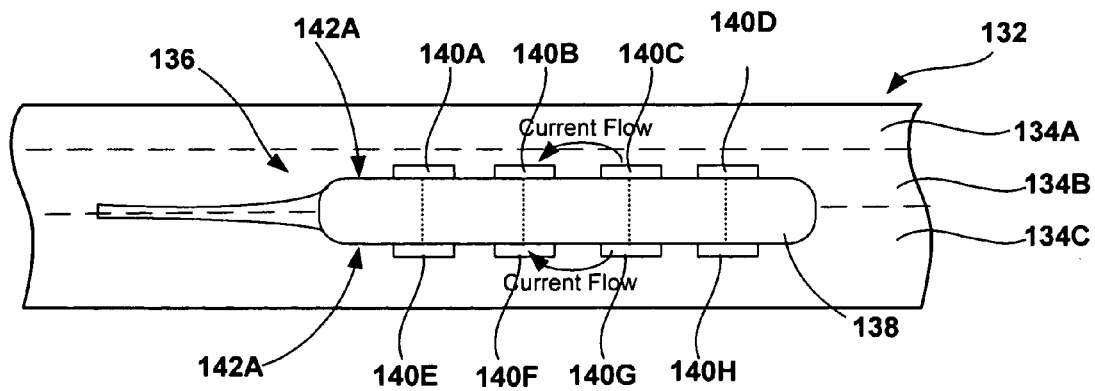

FIGS. 8A-8C are schematic diagrams illustrating a top and side views of example implantable medical leads having a plurality of electrodes located on more than one surface of the lead. More particularly, FIGS. 8A-8C illustrate examples of dual sided paddle leads. Such leads may be used in any of the systems described above with respect to FIGS. 1-3 to, for example, deliver PNFS.

FIGS. 8A and 8B are schematic diagrams illustrating a top and a side view, respectively, of dual sided paddle lead 124. FIG. 8B illustrates lead 124 implanted within tissue 132 of patient 12. Dual sided paddle lead 124 may be implanted in intra-dermal, deep dermal, or subcutaneous tissue of the patient.

Dual sided paddle lead 124 includes a lead body 126 carrying electrodes 128A-H (collectively referred to as "electrodes 128") located at its distal end. Lead body 126 may be designed similar to a paddle lead design known in the field of nerve stimulation, but, as shown, carries electrodes positioned on first and second surfaces 130A and 130B (collectively "surfaces 130"), e.g., the illustrated opposing, substantially parallel, top and bottom surfaces, instead of only on one surface. Lead body 126 has a substantially flat, paddle-like shape, e.g., has a substantially oblong or rectangular cross-sectional shape.

As shown in FIG. 8B, electrodes 128A-D are positioned on top surface 130A of lead body 126 and electrodes 128E-H are positioned on the bottom surface 130B of lead body 126. Electrodes 128A-H (collectively "electrodes 128") may extent above surfaces 130, may be recessed relative to the surfaces 130, or may be co-planar with the surfaces. Electrodes 128 may be electrically insulated from each other.

In the illustrated example of FIGS. 8A and 8B, dual sided paddle lead 124 includes eight electrodes, i.e., electrodes 128, positioned on the top and bottom surfaces of lead body 126 for purposes of illustration. However, dual sided paddle lead 124 may include a lesser or greater number of electrodes. A dual sided paddle lead having numerous electrodes may be particularly advantageous because the number of electrode possible combinations increases with the number of electrodes carried by the lead. In other words, providing a large number of electrode combinations increases the likelihood of discovering an electrode combination that achieves a high clinical efficacy with minimal side effects and favorable power consumption characteristics.

Electrodes 128 are arranged in a linear array along substantially the entire length of the top and bottom surfaces 130 of lead body 126. However, the invention is not limited as such. Rather, electrodes 128 may also be arranged in a two-dimensional array or any other regularly or irregularly spaced pattern, and may be distributed in discrete groups or "clusters," or be distributed substantially evenly over substantially the entirety of surfaces 130. FIGS. 9A-E illustrate various configurations of electrodes for dual sided paddle leads. In any case, each of electrodes 128 may be electrically coupled to an IMD (not shown), such as IMD 14 of FIG. 1, via a separate electrical conductor (not shown). The electrical conductors may reside in lead 124, where they may be electrically insulated and protected from body fluids.

The IMD may select one or more of electrodes 128 for electrode combinations to deliver stimulation to a patient as described in FIG. 1. With respect to FIG. 8B, electrodes 128 carried by dual sided paddle lead 124 deliver neurostimulation to tissue 132. In particular, electrodes 128A-D may deliver neurostimulation to tissue 134A located shallower than lead 124 and electrodes 128E-H may deliver neurostimulation therapy to tissue 134C located deeper than lead 124. For example, dual sided paddle lead 124 may be implanted between deep dermal tissue layer 134B and subcutaneous tissue layer 134C, and may stimulate nerves and/or tissue in both deep dermal tissue layer 134B and subcutaneous tissue layer 134C, as well as tissue within inter-dermal tissue layer 134A.

However, the invention is not limited as such. Rather, dual sided paddle lead 124 may be implanted within or between any of the intra-dermal, deep dermal, or subcutaneous tissue, or within any tissue or tissue layer of a patient. The thickness of dual sided paddle lead 124, e.g., the distance between electrodes 128A-D and electrodes 128E-H, may be varied or selected depending on various design parameters, such as the tissues or layers for which stimulation is desired, as well as the anticipated proximity of lead 124 to such tissues or layers. Further, the depth of different layers of tissue of the patient may vary depending on the anatomy of the patient, e.g., layers of tissue of an obese patient may be thicker than those of a slender patient.

In other embodiments in which lead body 126 is implanted within a particular tissue layer, such as deep dermal layer 134B, the thickness of lead 124 may also affect the degree of neurostimulation delivered to that layer. For example, if the thickness of lead 124 is sufficiently large, tissue 134B may not be substantially stimulated. However, the thickness of lead 124 may be sufficiently small that tissue 134B is stimulated to some degree. As a result, dual sided paddle lead 124 may be configured to stimulate substantially distinct layers of tissue.

Further, IMD 14 may selectively deliver stimulation via a variety of combinations of electrodes 128. Based on the electrodes within the combination and their polarity, as well as other stimulation parameters such as amplitude, IMD 14 may generate a current field via the selected electrodes that stimulates desired tissues or layers. IMD 14 may deliver stimulation via combinations of electrodes 128 on a single surface 130 to stimulate one or more layers of tissue proximate to that surface, or combinations that include electrodes 128 on both surfaces 130. Further, IMD 14 may simultaneously or alternatingly deliver stimulation via combinations of electrodes 128 from respective surfaces 130, to simultaneously or alternatingly stimulate layers above or below lead body 126.

In the illustrated example of FIG. 8B, electrodes 128A and 128B may be selected as the first electrode combination and electrodes 128F and 128G may be selected as the second electrode combination. Accordingly, a current flow is shown between electrodes 128A and 128B and electrodes 128F and 128G in FIG. 8. In such embodiments, the first electrode combination may deliver electrical stimulation in accordance with a first set of stimulation parameters and the second electrode combination may deliver electrical stimulation in accordance with a second set of stimulation parameters. For time-interleaved delivery, stimulation pulses may be delivered in an overlapping or non-overlapping manner, such that stimulation pulses delivered to different selected electrode sets are delivered in respective overlapping or non-overlapping time slots. In any case, the effect resulting from electrical stimulation, i.e., relief from pain or paresthesia, depends on the positions and polarities of the electrodes and the parameters associated with the stimulation pulses.

FIG. 8C is a schematic diagram illustrating a side view of another example dual sided paddle lead 136 implanted within tissue 132 of patient 12. Similar to dual sided paddle lead 124, dual sided paddle lead 136 includes a lead body 33 located at its distal end. Like lead 124, dual sided paddle lead 136 may also include electrodes 140A-D located on a first lead body surface 142A, and electrodes 140E-H located on a second lead body surface 142B.

However, in contrast to dual sided paddle lead 124, electrodes 140A-D are electrically coupled to corresponding ones of electrodes 140E-H, as illustrated by the dotted line in FIG. 8C. Any number of electrodes 140A-H on either of surfaces 142A and 142B may be electrically coupled such that they will deliver stimulation at the same time and with the same electrical characteristics, e.g., according to the same program. In the illustrated example, current flows from coupled electrodes 140C and 140G, which are act as cathodes on respective ones of surfaces 142A and 142B, to coupled electrodes 140B to 140F, which act as anodes.

Such coupling may reduce the programming flexibility of lead 136 by providing fewer different combinations of electrodes 140A-H that may be selected by a clinician. Further, where electrodes 140A-H on different surfaces 142A and 142B are electrically coupled, the ability of IMD 14 to deliver stimulation via either surface to particular layers or tissues may be limited or eliminated. However, a lead with fewer conductors may be more cost effective to manufacture, more flexible, and less prone to failure due to, for example, fracturing or degradation of the conductors. Further, in some embodiments, simultaneous delivery of stimulation to a large tissue region may be preferred over selectability of tissues or layers. If electrodes are near to the edge of a dual sided paddle, currents may be programmed to flow between two or more electrodes on opposite side of the paddle, giving the greatest possible spread of current beyond the edge of the paddle.

Figure 9A:
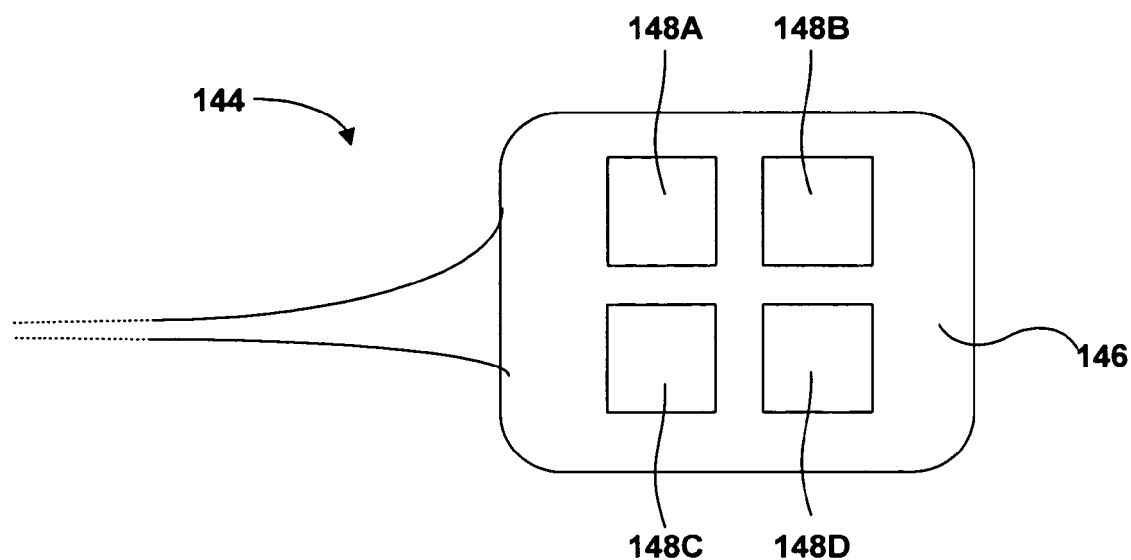
FIGS. 9A-9E are schematic diagrams illustrating top views of other example implantable medical leads having a plurality of electrodes located on more than one surface of the lead.
Figure 9B:
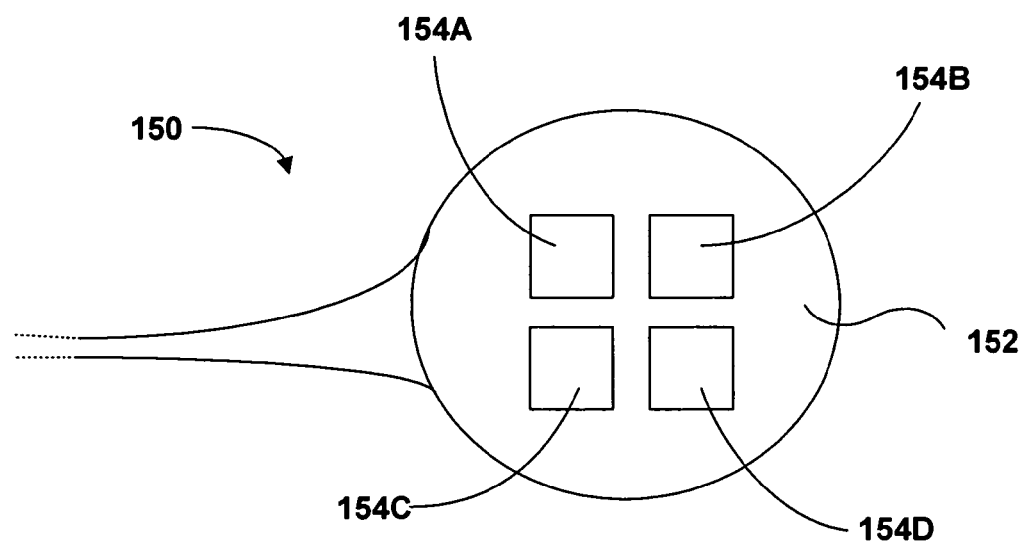

FIGS. 9A-9E are schematic diagrams illustrating top views of other example implantable medical leads having a plurality of electrodes located on more than one surface of the lead. FIGS. 9A-9E are schematic diagrams illustrating top views of example dual sided paddle leads. In particular, FIG. 9A is a top view of dual sided paddle lead 144 having a square shaped lead body 146 and FIG. 9B is a top view of dual sided paddle lead 150 having a circular shaped lead body 152. The circular shape of lead body 152 may require substantial dissection for implantation within patient 12, but may provide a form factor that best covers the patient's perceived region of pain. In contrast, the square or rectangular shape of lead body 146 is characterized by a substantially smaller width than lead body 152 and, thus, may reduce the amount of tissue damage caused during implantation. The illustrated surfaces of lead bodies 146 and 152 respectively include electrodes 148A-D and electrodes 154A-D. At least one other surface of lead bodies 146 and 152, such as an opposing or bottom surface not shown in FIGS. 9A and 9B, includes additional electrodes.

FIGS. 9A and 9B are merely exemplary and should not be considered limiting of the invention as broadly described in this disclosure. For example, a dual sided paddle lead as described in this disclosure may have a leady body that is circular, rectangular, square, round, oval, or any other uniform or non-uniform shape. Accordingly, the lead body may be shaped to match the patient's perceived region of pain, to reduce the amount of tissue damage cause during implantation, or achieve a tradeoff of these design parameters. Further, lead body shapes illustrated in FIGS. 9A and 9B are not limited to dual sided paddle leads. Rather, separate lead body levels of a multiple level lead, as will be described below, may have the illustrated shapes.

Figure 9C:
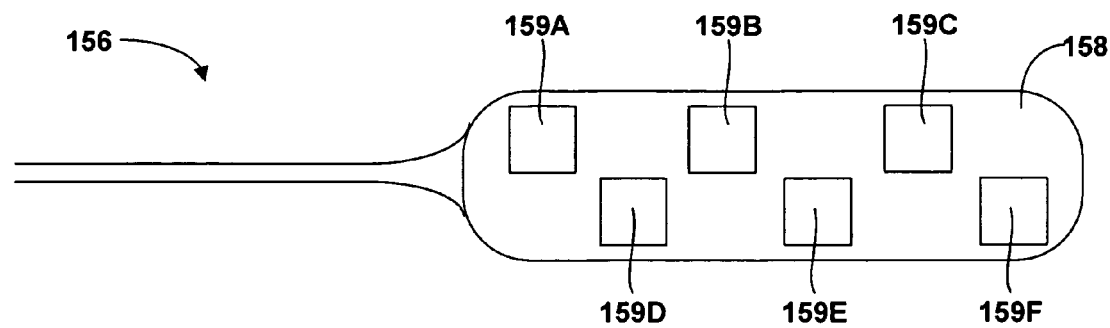
Figure 9D:
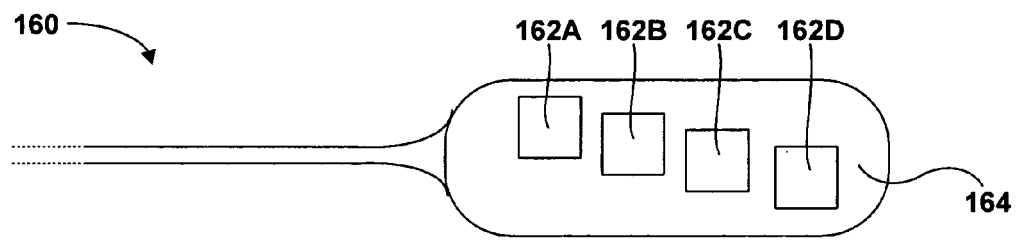
Figure 9E:
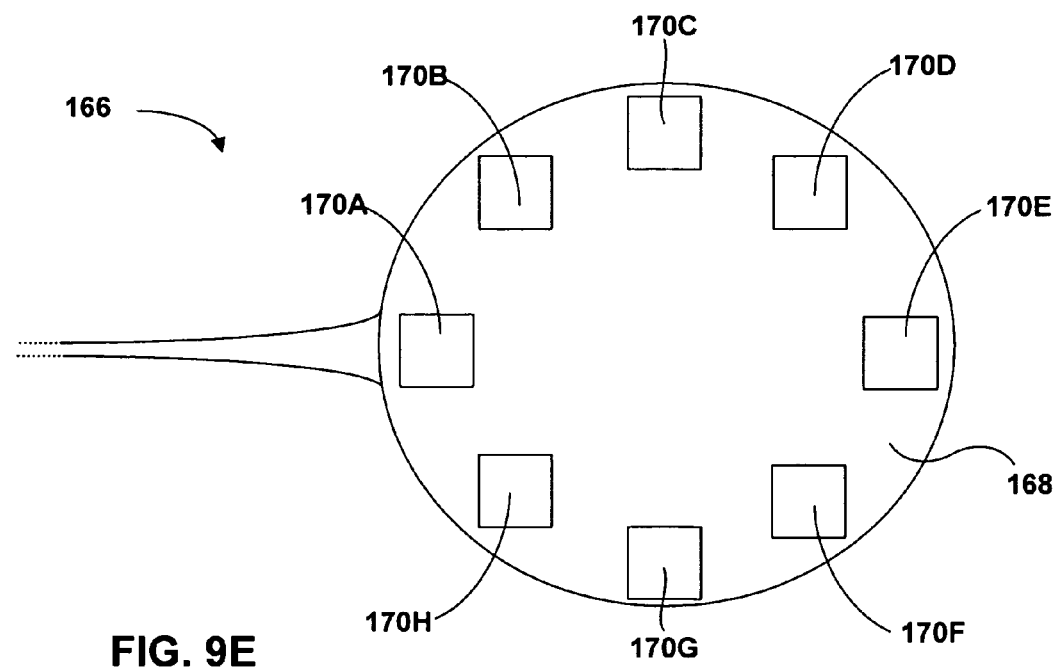

FIGS. 9C-E are schematic diagrams illustrating top views of other example dual sided paddle leads with various configurations of electrodes. However, the configurations of electrodes illustrated in FIGS. 9C-E are not limited to dual sided paddle leads. Rather, the configurations of electrodes illustrated in FIGS. 9C-E may also be used with multiple level leads described in this disclosure.

FIG. 9C is a top view of a dual sided paddle lead 156 having an elongated lead body 158 located at the distal end of the lead. Lead body 158 carries a two dimensional array of electrodes 159A-F (collectively referred to as "electrodes 159") on its top surface. A two-dimensional array generally refers to an ordering of electrodes along at least two different lines, e.g., as rows and columns. As shown in FIG. 9C, electrodes 159 are arranged in two evenly spaced rows that are staggered relative to each other. Alternatively, electrodes may be positioned irregular intervals within a line or at positions that do not represent an ordered pattern. In some embodiments, a two-dimensional array of electrodes may comprise electrodes arranged in three or more rows.

FIG. 9D is a top view of a dual sided paddle lead 160 having an elongated lead body 164 located at the distal end of the lead. Lead body 164 carries a linear array of electrodes 162A-D (collectively referred to as "electrodes 162") on its top surface. A linear array generally refers to an ordering of electrodes along a common line. In the illustrated example of FIG. 9D, electrodes 162 are arranged along the longitudinal axis of lead body 164 at regular intervals and are offset from each other rather than being in line with the longitudinal axis.

FIG. 9E is a top view of a dual sided paddle lead 166 having a circular shaped lead body 168 located at the distal end of the lead. Lead body 168 carries electrodes 170A-H (collectively referred to as "electrodes 170") on its top surface. Electrodes 170 are arranged in an ordered pattern about the circumference of lead body 168 with regular spacing. The number of electrodes shown in FIG. 9E is merely exemplary. Any number of electrodes may be arranged in an ordered pattern or, alternatively, at positions that do not represent an ordered pattern. In any case, the number and pattern of electrodes may be selected based on the patient's perceived region of pain.

FIGS. 10A-10D are schematic diagrams illustrating side views of other example implantable medical leads with electrodes positioned on various surfaces. FIGS. 10A-D are schematic diagrams illustrating side views of example multiple level leads implanted within tissue 174. Each of FIGS. 10A-D illustrates a multiple level lead with electrodes positioned on various surfaces to selectively deliver stimulation to layers of tissue located proximate to or between adjacent levels of the lead. A multiple level lead may be implanted within intra-dermal, deep dermal, or subcutaneous tissue of a patient and includes one or more electrodes positioned on at least one surface of each level of the lead.

Each of the multiple level leads illustrated in FIGS. 10A-D include a lead body with two lead body levels, i.e., an upper level and a lower level. Each of the lead body levels may have a substantially flat, paddle-like shape, as described above with reference to paddle leads 124 and FIGS. 8A-C. However, the invention is not so limited. Rather, a multiple level lead may include any number of lead body levels with any shape, even a simple cylindrical shape with a round cross section. In the interest of brevity, FIGS. 10A-D illustrate the various configurations for a multiple level lead having two levels. A multiple level lead having more than two levels follows from the description provided in this disclosure. Accordingly, FIGS. 10A-D are merely exemplary and should not be considered limiting of the invention as broadly described in this disclosure.

Figure 10A:
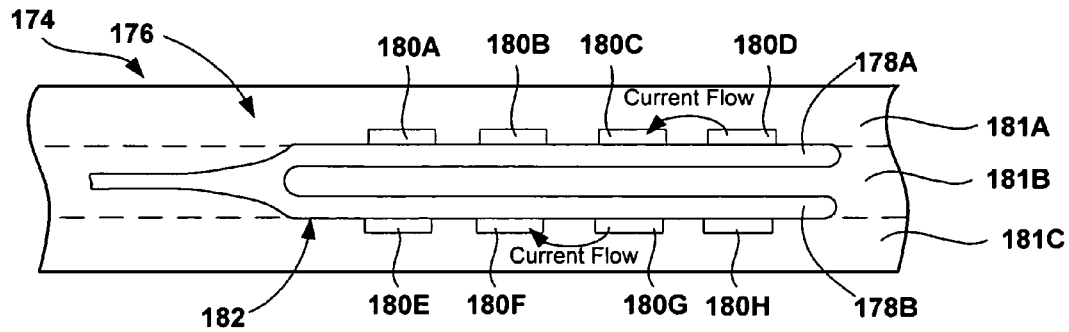
FIGS. 10A-10D are schematic diagrams illustrating side views of other example implantable medical leads with electrodes positioned on various surfaces.

FIG. 10A illustrates multiple level lead 176 implanted within tissue 174 of patient 12. Multiple level lead 176 includes a lead body 182 at its distal end comprising an upper lead body level 178A and a lower lead body level 178B (collectively "levels 178"). Upper level 178A may be located closer to the surface of the skin of patient 12 than lower level 178B. Upper level 178A carries electrodes 180A-D on its top surface and lower level 178B carries electrodes 180E-H on its bottom surface. In this manner, multiple level lead 176 carries electrodes 180A-H (collectively "electrodes 180") on opposite surfaces of adjacent levels such that electrodes 180A-D and electrodes 180E-H face away from each other.

In the illustrated example of FIG. 10A multiple level lead 176 includes eight electrodes for the purposes of illustration. However, as previously described with respect to dual sided paddle leads in FIGS. 8A and 8B, multiple level lead 176 may include a lesser or greater number of electrodes. Again, having numerous electrodes may be particularly advantageous because the number of electrode possible combinations increases with the number of electrodes carried by the lead. In other words, providing a large number of electrode combinations increases the likelihood of discovering an electrode combination that achieves a high clinical efficacy with minimal side effects and favorable power consumption characteristics.

Electrodes 180A-D and 180E-H may be arranged in any regular or irregular pattern such as those illustrated in or described with respect to FIGS. 9A-E. For example, electrodes 74A-D and 74E-H may be arranged in the same pattern, such as the two-dimensional array illustrated in FIG. 9C, or may be arranged in different patterns, such as the two-dimensional array illustrated in FIG. 9C and the linear array illustrated in FIG. 9D. In any case, each of electrodes 180A-D and 180E-H may be electrically coupled to an IMD (not shown), such as IMD 14 of FIG. 1, via a separate electrical conductor (not shown) within lead 176.

In operation, the IMD may apply stimulation across selected electrodes of 180A-D and 180E-H to deliver, for example, PNFS to various layers of tissue 174. In particular, one or more of electrodes 180A-D may deliver stimulation to tissue 181A located shallower than upper level 178A and one or more of electrodes 180E-H may deliver stimulation therapy to tissue 181C located deeper than lower level 178B. In one example, multiple level lead 176 may be implanted in deep dermal tissue 181B and may stimulate nerves and/or tissue in both intra-dermal and subcutaneous tissue 181A and 181C, respectively. However, the invention is not limited as such and multiple level lead 176 may be implanted in intra-dermal, deep dermal, or subcutaneous tissue. Regardless of which layer of tissue multiple level lead 176 is implanted, multiple level lead may deliver stimulation to a layer of tissue located shallower than upper level 178A and a layer of tissue located deeper than lower level 178B.

However, the distance between upper level 178A and lower level 178B may be selected based on one or more design parameters. For example, the distance between upper level 178A and lower level 178B may be selected in a similar manner to selecting the thickness of a dual sided paddle lead, as described with respect to dual sided paddle lead 124 in FIGS. 8A and 8B. In particular, the distance may be selected such that upper lead body 180A and lower lead body 180B are implanted within distinct layers of tissue, such as intra-dermal and subcutaneous tissue, respectively. In this case, the distance may vary depending on the anatomy of the patient, e.g., layers of tissue of an obese patient may be thicker than those of a slender patient.

The distance may also affect the degree of stimulation delivered to tissue 181B, i.e., the layer of tissue in which multiple level lead 176 is implanted. For example, if the distance between upper level 178A and lower level 178B is sufficiently large, neurostimulation may only be delivered to tissue 181A and 181C. In other words, tissue 181B may not be substantially stimulated. In contrast, however, the height may be sufficiently small such that tissue 181B is stimulated to some degree.

Again, multiple level lead 176 may deliver stimulation, such as PNFS, to tissue 181A and 181C at the same time or in an alternating or interleaved fashion. For example, a first electrode combination selected from electrodes 180A-D may deliver PNFS to tissue 181A and a second electrode combination selected from electrodes 180E-H may deliver PNFS to tissue 181C. Accordingly, a current flow is shown between electrodes 180C and 180D and electrodes 180F and 180G in FIG. 10A. In such embodiments, the first electrode combination may deliver electrical stimulation in accordance with a first set of stimulation parameters and the second electrode combination may deliver electrical stimulation in accordance with a second set of stimulation parameters. For time-interleaved delivery, stimulation pulses may be delivered in an overlapping or non-overlapping manner, such that stimulation pulses delivered to different selected electrode sets are delivered in respective overlapping or non-overlapping time slots. In any case, the effect resulting from electrical stimulation, i.e., relief from pain or paresthesia, depends on the positions and polarities of the electrodes and the parameters associated with the stimulation pulses.

Figure 10B:
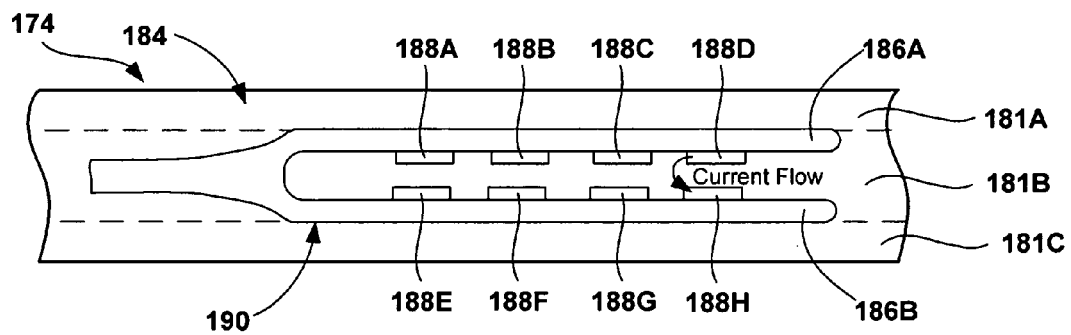

FIG. 10B is a side view illustrating multiple level lead 184 implanted within tissue 174 of patient 12. Similar to multiple level lead 176, multiple level lead 184 includes a lead body 190 with an upper lead body level 186A and a lower lead body level 186B (collectively "levels 186"). However, in contrast to multiple level lead 176, upper level 186A carries electrodes 188A-D on its bottom surface and lower lead body level 186B carries electrodes 188E-H on its top surface. As a result, multiple level lead 184 carries electrodes 188A-D and 188E-H on adjacent surfaces of adjacent levels such that electrodes 188A-D and 188E-H face each other.

Consequently, multiple level lead 184 may focus delivery of stimulation to tissue, such as layer 181B, located between adjacent levels 186. With reference to the example illustrated by FIG. 10B, multiple level lead 184 may be able to deliver stimulation to tissue 181B without substantially stimulating tissue 181A located superior to upper level 186A or tissue 186C located inferior to lower level 186B. Upper level 186A and lower level 186B may electrically isolate tissue 181A and 181C from being stimulated by neurostimulation delivered to 181B. Again, tissues 181A, 181B and 181C may correspond to intra-dermal, deep dermal and subcutaneous tissue layers within a region 19, and the IMD may deliver PNSF via lead 184.

In some embodiments, as illustrated by the labeled current flow in FIG. 10B, an IMD may apply electrical stimulation pulses across electrodes 188A-H such that an anode and cathode are not on the same level. However, the invention is not so limited. An IMD may deliver stimulation to tissue between levels 186 via any combination of electrodes 188A-H on one or both of the levels.

Figure 10C:
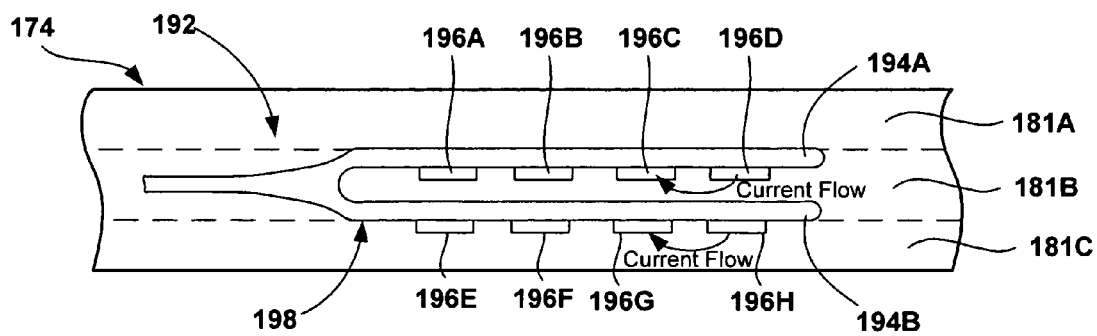

FIG. 10C is a side view illustrating another example multiple level lead 192 implanted within tissue 174 of patient 12. Again, multiple level lead 192 is similar to multiple level leads 176 and 184 with respect to physical structure, i.e., multiple level lead 192 includes a distal lead body 198 with an upper level 194A and a lower level 194B. However, unlike multiple level leads 176 and 184, upper level 194A carries electrodes 196A-D on its bottom surface and lower level 194B carries electrodes 196E-H on its bottom surface. As a result, multiple level lead 192 delivers neurostimulation to tissue 181B located between upper level 194A and lower lead level 194B and tissue 181C located deeper than lower lead body 194B.

In particular, multiple level lead 192 may deliver neurostimulation, such as PNFS, to tissue 181B and 181C without substantially stimulating tissue 181A. In operation, the IMD (not shown) coupled to multiple level lead 192 may apply electrical stimulation pulses across one or more of electrodes 196A-D and one or more of electrodes 196E-H to stimulate tissue 181B and tissue 181C, respectively. In this case, the IMD may select anode and cathode on the same level. As an example, FIG. 10C illustrates a current flow between electrodes 196C and 196D to stimulate tissue 181B and between electrodes 196G and 196H to stimulate tissue 181C. When delivering neurostimulation to tissue 181B and 181C, upper level 194A may substantially electrically isolate tissue 181A from being stimulated by neurostimulation delivered to tissue 181B and tissue 181C.

Figure 10D:
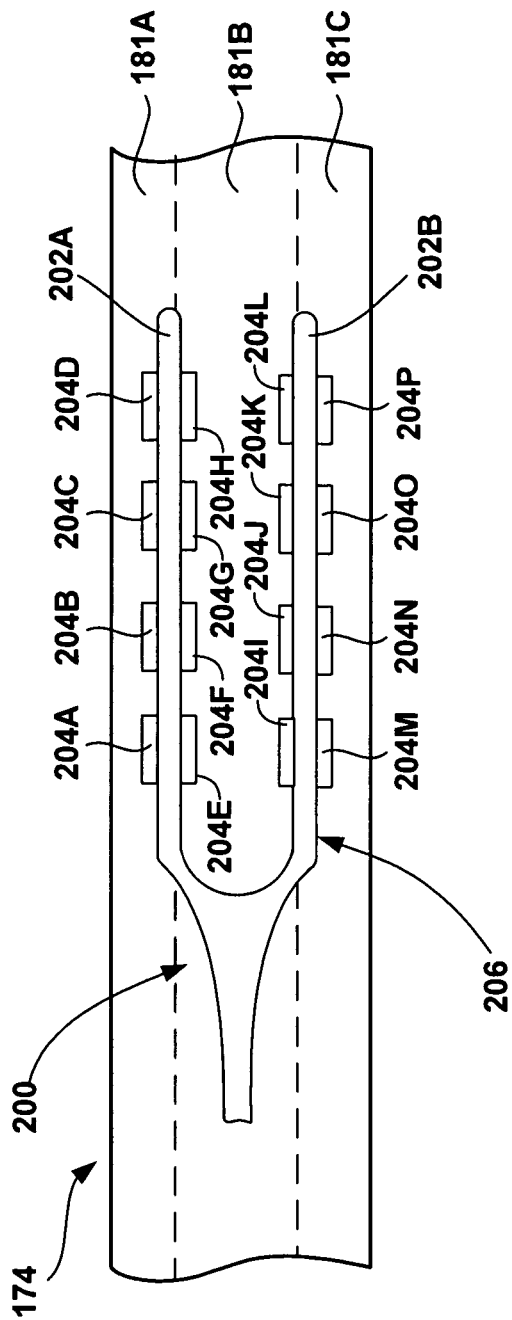

FIG. 10D is a side view illustrating multiple level lead 200 implanted within tissue 174 of patient 12. Multiple level lead 200 is similar to multiple level leads 176, 184, and 192 with respect to physical structure, i.e., multiple level lead 200 includes a distal lead body 206 with an upper level 202A and a lower level 202B. However, unlike multiple level leads 176, 184, and 192, upper level 202A carries electrodes 204A-D on its top surface and electrodes 204E-H on its bottom surface, and lower level 202B carries electrodes 204I-L on its top surface and electrodes 204M-P on its bottom surface. As a result, multiple level lead 200 may selectively deliver neurostimulation to any one or more of tissue 181A, 181B, and 181C.

Each of electrodes 204A-P are electrically isolated from each other and, thus, electrode combinations may be selected to deliver stimulation, such as PNFS, to any desired one or more of tissue layers 181A, 181B, and 181C. However, in other embodiments, electrodes on different surfaces of the levels may be electrically coupled in the manner discussed above with reference to FIG. 8C. Such coupling may simplify the structure and manufacturing of a multiple level lead.

Figure 11:
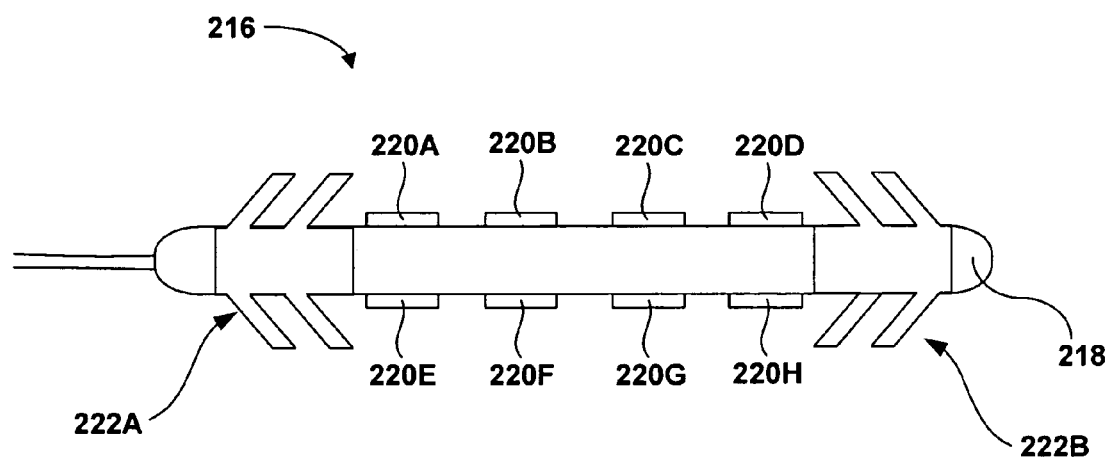
FIG. 11 is a schematic diagram illustrating an example implantable medical lead including fixation structures.

FIG. 11 is a schematic diagram illustrating a lead 216 that includes fixation structures. Lead 216 includes a lead body 206 at its distal end that carries electrodes 220A-H (collectively referred to as "electrodes 220") on multiple surfaces. Lead 216 may be a dual-sided paddle lead in which lead body 206 has a substantially flat, paddle-like shape, and may be substantially similar to dual sided paddle lead 124 of FIGS. 8A and 8B. However, unlike dual sided paddle lead 124, dual sided paddle lead 216 includes fixation structures 222A and 222B for securing lead 216 that prevent lead 216 from migrating from the implantation site.

Fixation structures may protrude from lead body 206 to engage tissue proximate to the lead body, as illustrated in FIG. 11. Fixation structure 222 may comprise one or more of tines, barbs, hooks, actively or passively deployable fixation structures, or collapsible or expandable fixation structures. Fixation structures may include titanium, stainless steel, nitinol, hydrogel, or any of a variety of materials. Tines, barbs and hooks may pierce tissue proximate to lead 216 to prevent migration after implantation. Tissue ingrowth surrounding tines or barbs may further secure lead 216. Not shown, the tines, barbs and hooks may lie in the plane of the paddle.

When not acted upon by a force, collapsible structures assume an expanded configuration with the fixation structures extending away from lead body 206. However, when inserted into an insertion device, such as a needle, the collapsible fixation structures move close to lead body 218 assuming a collapsed configuration. When lead 216 is expelled from the insertion device, the fixation structures move toward their expanded positions.

Actively deployable fixation structures may include one or more actively deployable clips which, upon deployment, provides fixation of the lead to tissue proximate to the lead. The clip may be deployed in a variety of ways, such as releasing the clip from a restraint using a surgical tool or releasing the clip upon passage of the lead through body tissue to prevent withdrawal of the lead from body tissue. In this manner, protruding fixation structures 222A and 222B may enable a less complicated and time consuming method for securing a paddle lead, such as dual sided paddle lead, a multiple level lead, or a paddle lead known in the nerve stimulation field, to tissue to prevent migration. Other embodiments may include any type of fixation mechanism used to fix cardiac leads.

In some embodiments, dual sided paddle lead 216 may only include protruding fixation structures 222B or 222A, i.e., may only include protruding fixation structures on a distal or a proximal end. Accordingly, FIG. 6 is merely exemplary and should not be considered limiting of the invention as broadly described in this disclosure. For example, protruding fixation structures 222A and 222B may be implemented with paddle leads that include electrodes on only a single surface. Protruding fixation structures located at the distal end of such paddle leads may offer similar advantages as described with respect to dual sided paddle lead 216. Further, fixation structures may be provides on multiple level leads as described herein.

Figure 12:
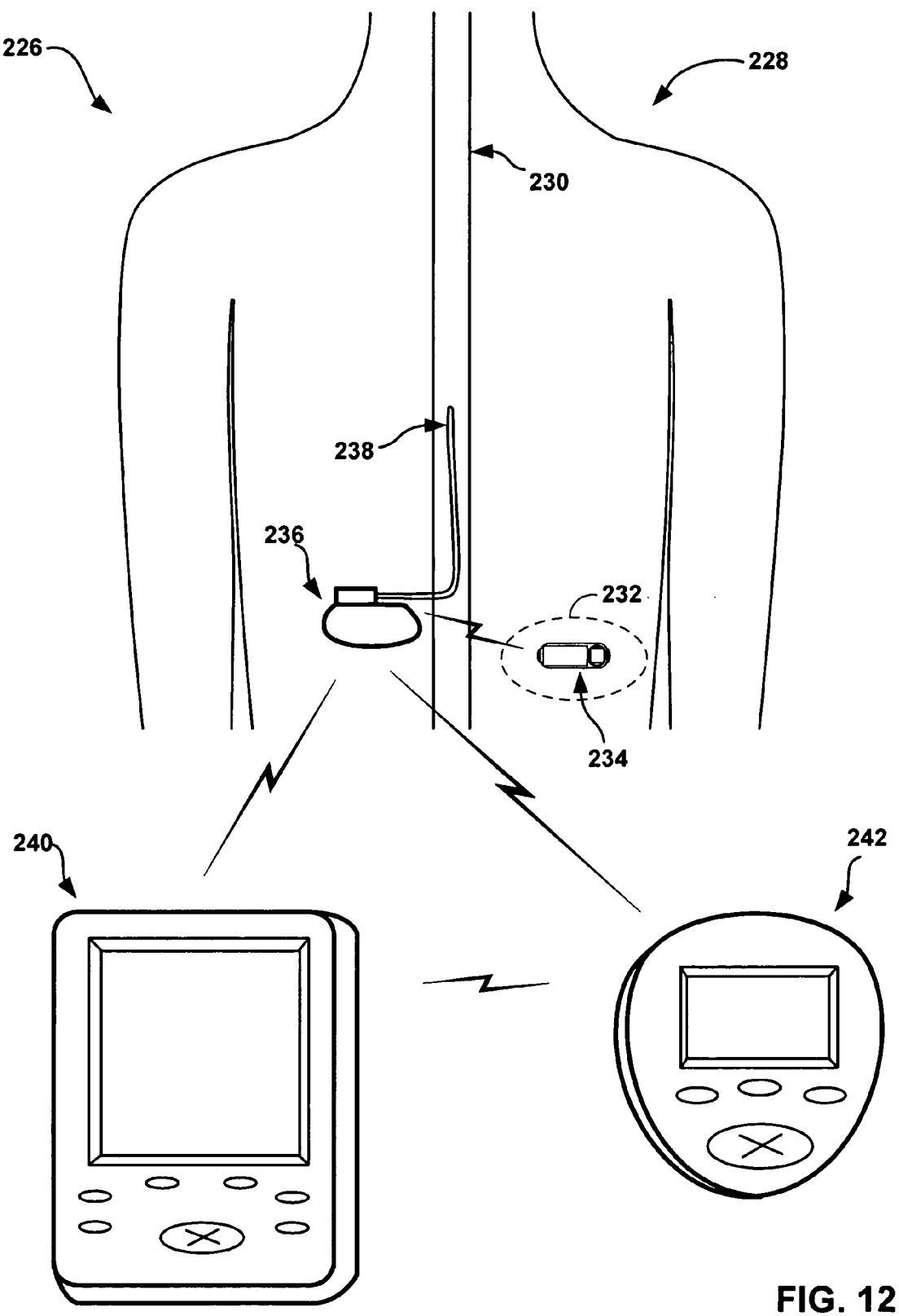
FIG. 12 is a conceptual diagram illustrating another example system for delivering peripheral nerve field stimulation (PNFS) and one or more other types of therapy to a patient, the system including multiple implantable medical devices.

FIG. 12 is a conceptual diagram illustrating another example system that delivers PNFS in combination with at least one other therapy. More particularly, FIG. 12 illustrates a system 226 that includes multiple medical devices for delivering PNFS and the at least one other therapy. In the illustrated example, system 226 includes a first IMD 234 that delivers PNFS to a region in which a patient 228 experiences pain, and a second IMD 236 that delivers the at least one other therapy.

Through delivery of a combination therapy that includes PNFS and one or more other types of therapy, system 226 may be able to more completely address complex or multifocal pain than would be possible through delivery of either PNFS or the other therapies alone. In addition, the combination of PNFS with one or more other types of therapy may reduce the likelihood that neural accommodation or plasticity will impair the perceived effectiveness of any of the therapies. In some embodiments, as illustrated in FIG. 12, IMDs 234 and 236 may communicate, e.g., wirelessly via radio frequency or body conduction, to coordinate the delivery of their respective therapies.

As illustrated in FIG. 12, IMD 234 may be configured for implantation within region 232, e.g., may include a relatively miniaturized housing. Further, as will be described in greater detail below, IMD 234 may have a housing with electrodes on multiple housing surfaces for delivery of PNFS to region 232. Location of electrodes on multiple surfaces of a housing implanted within a painful region may allow a large area and variety of tissues to be stimulated, and may provide programming flexibility with respect to selection tissues to be stimulated, as described above with respect to the implantable medical leads of FIGS. 8A-10D.

However, the invention is not limited to embodiments in which IMD 234 is implanted within an axial back region as illustrated in FIG. 12. In other embodiments, IMD 234 may be implanted in the face, head, chest, stomach, pelvis, or limbs of patient 228 for delivery of PNFS to a region in which the patient experiences pain. Moreover, the invention is not limited to embodiments in which IMD 234 includes housing electrodes, or is implanted within region 232. In other embodiments, IMD 234 may be coupled to a lead that extends to a region in which patient 232 experiences pain.

In the illustrated embodiment, additional IMD 236 delivers spinal cord stimulation (SCS) to the spinal cord 230 of patient 228 in combination with delivery of PNFS. IMD 236 delivers SCS via electrodes located on one or more leads 238 implanted proximate to spinal cord 230. IMD 236 may deliver SCS to any of the spinal cord regions and for any of the purposes described above with respect to FIGS. 1-3.

However, the invention is not limited to embodiments in which lead 238 extends to spinal cord 230, or IMD 236 delivers SCS. In other embodiments, an IMD may deliver one or more of PNS, DBS or CS via leads extending to appropriate positions proximate to target nerves, or on or within the brain, as described above with reference to FIGS. 1-3. Further, the invention is not limited to embodiments in which the other therapy that treats pain is a type of neurostimulation. In some embodiments, for example, IMD 236 may deliver a drug or other therapeutic agent in combination with the PNFS delivered by IMD 234. In such embodiments, IMD 236 may include a reservoir and pump, and be coupled to a catheter that extends to a target location for delivery any of a variety of therapeutic agents, as described above with reference to FIGS. 1-3.

Also, the invention is not limited to IMDs, for example, an external device may deliver a therapy, such as transcutaneous electrical neurostimulation (TENS), in combination with the delivery of PNFS by IMD 234. Moreover, other delivery mechanisms, such as a patch or other transdermal delivery mechanism, or oral consumption by a patient, may be used for a combination therapy including a therapeutic agent. For example, patient 228 may absorb drugs through a patch at region 232 to further relieve pain experienced at region 232 or enhance the PNFS therapy. As one example of the synergy between therapies, PNFS delivered to region 232 by IMD 234 may reduce allodynia, thereby allowing a patch to be applied to the skin of patient 228 to deliver drug therapy. Similarly, PNFS may sufficiently reduce allodynia so that a TENS electrode can be applied to the skin.

System 226 may deliver PNFS in combination with other types of therapy simultaneously, or in an interleaved or alternating fashion, as described above. For example, when the combined therapies include a plurality of electrical stimulation therapies, IMDs 234 and 236 may deliver electrical pulses according to each of the therapies in an alternating or interleaved fashion, e.g., each pulse delivered according to a different one of the therapies. Consequently, the delivery of each therapy can be optimized at each site. Clinician and patient programmers 240 and 242 may be substantially similar to the programmers discussed above, and may be used to program or control delivery of therapy by each of IMDs 234 and 236 via telemetry in the manner discussed above with reference to programming of a single IMD and FIGS. 1-6.

Figure 13A:
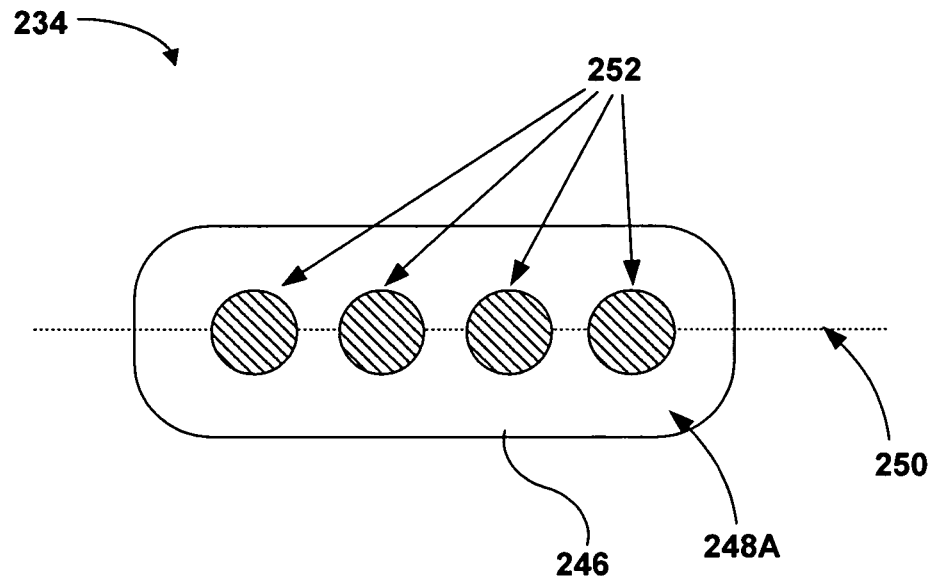
FIGS. 13A and 13B are schematic diagrams respectively illustrating top and side views of the implantable medical device of FIG. 1 with electrodes located on a top surface and a bottom surface of the implantable medical device housing.
Figure 13B:
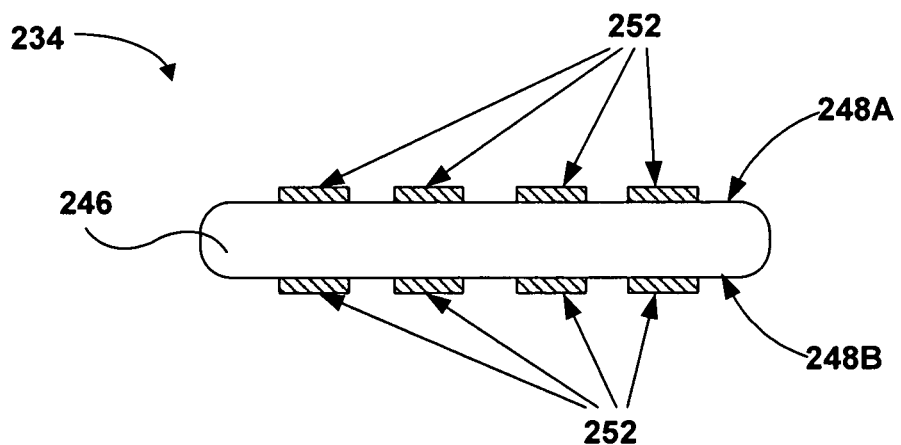

FIGS. 13A and 13B are schematic diagrams respectively illustrating top and side views of the implantable medical device of FIG. 12 with electrodes located on a top surface and a bottom surface of the implantable medical device housing. As illustrated in FIGS. 13A and 13B, IMD 234 includes a housing 246 with a top surface 248A and a bottom surface 248B. IMD 244 also includes a plurality of electrodes 252. A first subset of electrodes 252 is located on top surface 248A, while a second subset of electrodes 252 is located on bottom surface 248B.

IMD 234 may deliver electrical stimulation, e.g., pulses, via a selected combination of electrodes 252 from one or both of top surface 248A and bottom surface 248B. When IMD 234 is implanted within or between one or more of the interdermal, deep dermal, and/or subcutaneous tissue layers, the subsets of electrodes 252 on the housing surfaces 248 may be respectively located more proximate to different ones of the layers. The ability of a clinician to select electrodes 252 from one or both of housing surfaces 248 for an electrode configuration for a stimulation program, may allow the clinician to select a current field configuration that stimulates a desired one or more of the tissue layers. In other words, an IMD 244 with electrodes 252 located on multiple housing surfaces 248 according to the invention may selectively stimulate any one or more tissue layers.

As illustrated in FIG. 13B, top and bottom housing surfaces 248A and 248B (collectively "housing surfaces 248") may be substantially parallel, opposing, major surfaces of housing 246. A "major" surface of a housing has a relatively large surface area when compared to other surfaces. For example, top and bottom housing surfaces 248 are major surface in that they have a relatively large surface area when compared to the side surfaces of housing 246. While electrodes 252 are shown located on opposing, substantially parallel surfaces 248 of housing 246, electrodes 252 may be located on adjacent surfaces of the housing, e.g., top surface 248A and one of the side surfaces of housing 246. In some alternative embodiments, electrodes 252 may be located on three or more surfaces of housing 246. Electrode areas or spacing might have to be optimized depending on the tissue stimulated, e.g., skin versus muscle.

In the example illustrated by FIG. 13A, electrodes 252 are distributed over substantially the entire length of top surface 248A. Further, electrodes 252 are arranged in a row substantially along an axis 250 of top surface 248A. However, the invention is not limited to the illustrated arrangement of electrodes 252, or any particular arrangement of electrodes. For example, electrodes may be arranged on surfaces in multiple rows substantially parallel to axis 250, in a substantially "checkerboard-like" pattern, or a substantially irregular pattern. Further, electrodes 252 may be distributed across substantially the entirety of one or both of surfaces 248, or may be grouped into one or more discrete clusters at various positions on the surface.

Moreover, the number, size and shape of electrodes 252 illustrated in FIGS. 13A and 13B are merely exemplary. IMD 234 may include as few as a single electrode 252 on each of housing surfaces 248. Further, although illustrated as substantially flat electrode pads with substantially circular cross-sectional shapes, electrodes 252 may have any two or three-dimensional shape.

Figure 14A:
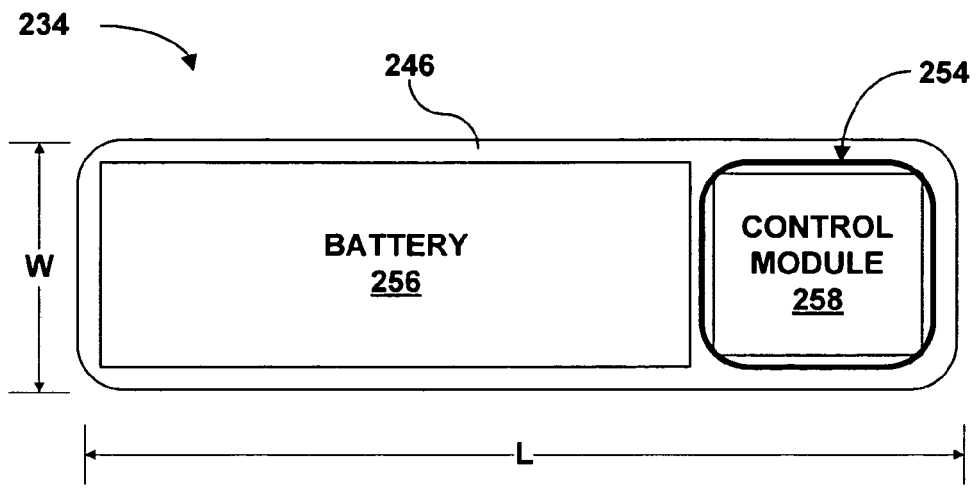
FIGS. 14A and 14B are schematic diagrams respectively illustrating top and side cross-sectional views of the implantable medical device of FIG. 13.
Figure 14B:
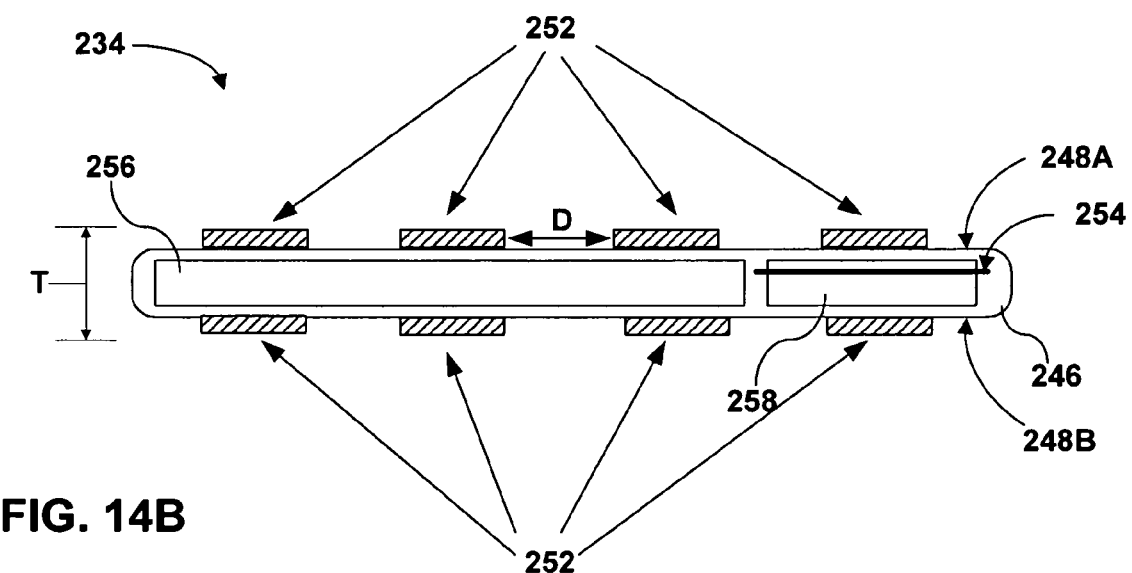

FIGS. 14A and 14B are schematic diagrams respectively illustrating top and side cross-sectional views of IMD 234. As shown in FIGS. 14A and 14B, housing 246 of IMD 244 houses a control module 258, a battery 256, and a coil 254 encircling control module 258. In some embodiments, coil 254 may encircle control module 258, battery 256, or both.

Control module 258 receives power from battery 256 to drive the electrodes 24 according to one or more stimulation programs, which may be stored within control module 258 and/or received from one of programmers 240, 242, e.g., via radio frequency (RF) or inductive telemetry. Control module 258 may include control electronics, such as any one or more of a microprocessor, DSP, ASIC, FPGA, or other digital logic circuitry. Control module 258 may also include memory, such as any one or more of ROM, RAM, NVRAM, EEPROM, or flash memory. The memory of control module may store stimulation programs, as well as program instructions that, when executed by the control circuitry of control module 258, cause control module 258 and IMD to provide the functionality ascribed to them herein. Control module 258 may also include stimulation generation circuitry, such as voltage or current pulse generators that include capacitors, regulators, current mirrors, or the like, as is known in the art.

Battery 256 may be rechargeable, and may have a capacity of at least 20 milliamp-hr, more preferably at least 25 milliamp-hr, and still more preferably at least 30 milliamp-hours. In this case, battery 256 comprises a capacity almost an order of magnitude larger than conventional microstimulators. In some embodiments, battery 256 may comprise a lithium ion rechargeable battery.

Coil 254 may serve as a telemetry coil for wireless communication with an external programmer, e.g., programmers 240 and 242. Coil 254 may be formed of windings of copper or another highly conductive material. In some embodiments in which battery 256 is rechargeable, coil 254 may also act as an inductive power interface to recharge battery 256, e.g., may inductively receive energy from an external recharging unit (not illustrated) through the skin of patient 228 to recharge battery 256. In other embodiments, separate coils may be provided for communication and recharging.

Further, the invention is not limited to embodiments in which battery 256 is rechargeable, or in which IMD 244 includes a battery. For example, IMD 234 may include a non-battery power source, such as a supercapacitor. In other embodiments, IMD 234 may not store power, and control module 258 may instead receive power substantially continuously from an external source via coil 254 or another coil.

Housing 246 may be formed from any of a variety of materials such as silicone, polyurethane, other polymeric materials, titanium, stainless steel or ceramics. As shown in FIG. 14A, housing 246 conforms to a substantially rectangular form factor. In alternative embodiments, housing 246 may include curved, angled, or asymmetric edges such that the housing fits within the implant region of the patient. Housing 246 may conform to a miniaturized form factor with a low profile in order to fit within a desired layer of tissue for implant.

IMD 234 or housing 246 may have a length (L) of approximately 30 to 160 mm, a width (W) of approximately 10 to 20 mm and a thickness (T) of approximately 3 to 6 mm. In some embodiments, IMD 234 or housing 246 may have a length (L) less than approximately 50 mm, and a thickness (T) of less than approximately 6 mm. In some embodiments, IMD 234 or housing 246 comprises a length (L) of less than or equal to 36.6 mm (1.44 inches), a width (W) of less than or equal to 14.5 mm (0.57 inches), and a thickness (T) of less than or equal to 4.5 mm (0.177 inches). In some embodiments, IMD 234 may include approximately 0.25 mm (0.01 inches) of insulation between control module 258, battery 256 and housing 246. The walls of housing 246 may comprise a total thickness of approximately 0.71 mm (0.03 inches).

Control module 258 and coil 254 are designed to be very thin and flat to fit within housing 246. For example, control module 258 may comprise a length of less than or equal to approximately 6.5 mm (0.256 inches), a width of less than or equal to approximately 9.4 mm (0.37 inches), and a thickness of less than or equal to approximately 3.6 mm (0.14 inches). Further, although battery 256 comprises a capacity almost an order of magnitude larger than some conventional microstimulators, battery 256 has a relatively small capacity compared to full size IMDs. Therefore, coil 254 may be smaller than coils within traditional IMDs. Coil 254 may comprise inner dimensions slightly larger than the dimensions of control module 258 given above.

Coil 254 may comprise an inner length of approximately 6.7 mm (0.265 inches) and an inner width of approximately 9.7 mm (0.38 inches). The outer dimensions of coil 254 may comprise an outer length of approximately 8.4 mm (0.33 inches) and an outer width of approximately 11.7 mm (0.46 inches). Coil 254 may also comprise a thickness of approximately 2.5 mm (0.10 inches).

Similarly, battery 256 may be configured to fit within the relatively thin and flat housing 246. For example, battery 256 may be a lithium ion battery with a thin, generally flat housing or cylindrical housing. In the case of a pin type cell, battery 256 may have an aluminum housing with a crimped or riveted pin feedthrough. In some embodiments, battery 256 alternatively may comprise a foil pack battery.

Battery 256 may comprise a length of less than or equal to approximately 24.9 mm (0.98 inches), a width of less than or equal to approximately 12.7 mm (0.50 inches), and a thickness of less than or equal to approximately 3.3 mm (0.13 inches). Battery 256 may be loaded with electrical charge in a standard or adjustable manner, which may affect the dimensions of possible battery dimensions. Battery 256 may conform to one of a variety of designs. Some examples are given in Table 3 below.

TABLE 3

| | 3.0 mm thick standard loading | 3.0 mm thick adjustable loading | 3.3 mm thick standard loading | 3.3 mm thick adjustable loading |
| --- | --- | --- | --- | --- |
| Length (mm) | 25.4 | 25.4 | 25.4 | 24.9 |
| Width (mm) | 16.5 | 14.2 | 13.2 | 12.7 |
| Capacity (mA-hr) | 30 | 30 | 31 | 30 |
| Battery Case Volume (cc) | 1.26 | 1.08 | 1.11 | 1.04 |
| Coating Deposition (mg/cm$^2$) | 22 | 12.1 | 22 | 12.32 |

IMD 234 may be over-discharge protected. However, since battery 256 conforms to an extremely small form factor, the over-discharge protection may be difficult to realize using traditional approaches, such as extra battery capacity. Therefore, IMD 234 may include a switch to disconnect battery 256 from the load, e.g., an adjustable loading battery, when a predetermined voltage is reached. In other cases, battery 256 may comprise an over-discharge tolerant battery.

Each of electrodes 252 may be substantially circular, square or rectangular, or may have other cross-sectional shapes or substantially irregular cross-sectional shapes. In the case of a circular cross-sectional shape, each electrode 252 may have a diameter of approximately 0.5 mm to 1.5 mm, and more preferably 1 mm. IMD 234 may include between 2 and 32 electrodes, although greater numbers of electrodes are possible. Inter-electrode distances (D) on surfaces 248 may be within a range from approximately 0.1 mm to approximately 5.0 mm, and in some embodiments may be approximately to 0.5 mm.

Electrodes 252 may be distributed on each of housing surfaces 22 in a linear or a two-dimensional array. A linear array generally refers to an ordering of electrodes 252 along a common line or axis, such as axis 250 illustrated in FIG. 13A, whereas a two-dimensional array generally refers to an ordering of electrodes 252 along at least two different lines, e.g., as rows and columns, or a checkerboard pattern. In either case, the array of electrodes 252 may have a regular, periodic pattern such that electrodes are positioned at regular spatial intervals within a line, row or column.

Alternatively, the array may be irregular such that electrodes 252 are positioned at irregular intervals or at positions that do not represent an ordered pattern. Further, as discussed above, electrodes 252 need not be located substantially along substantially the entire lengths or across substantially the entire surface areas of housing surfaces 248. Instead, electrodes 252 may be clustered or grouped at particular locations on the surfaces. However, distributing electrodes 252 along substantially the entire length or across substantially the entire surface area of a housing surface 248 may enable IMD 244 to selectively stimulate tissues within a larger region, which may make it more likely that a desirable electrode configuration and stimulation program in terms of efficacy and side effects will be discovered.

Figure 15A:
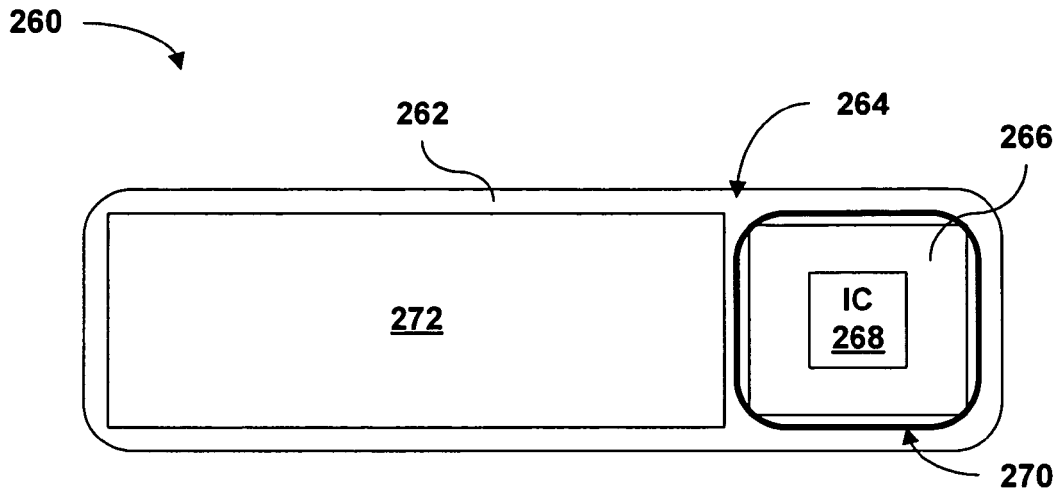
FIGS. 15A and 15B are schematic diagrams respectively illustrating top and side cross-sectional views of another example implantable medical device with electrodes located on multiple housing surfaces, in which the housing includes a bend.
Figure 15B:
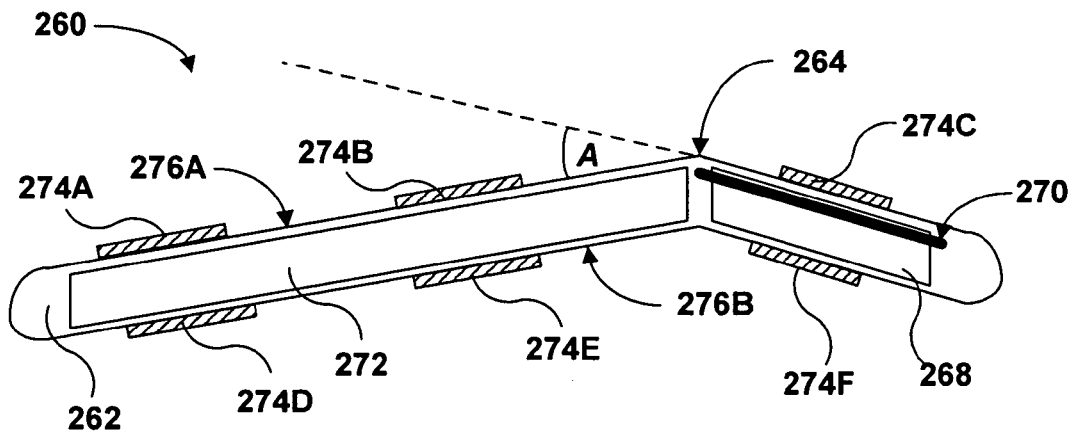

FIGS. 15A and 15B are schematic diagrams respectively illustrating top and side cross-sectional views of another example implantable medical device with electrodes located on multiple housing surfaces, in which the housing includes a bend. As shown in FIGS. 15A and 15B, IMD 260 includes a housing 262 with a top surface 276A and a bottom surface 276B, and electrodes 274A-C and 274D-F located on top surface 276A and bottom surface 276B, respectively. Electrodes 274A-F (collectively "electrodes 274") may be substantially similar to electrodes 252 discussed above, and arranged on surfaces 276A and 276B (collectively "housing surfaces 276") in substantially the same manner as discussed above with reference to electrodes 252.

Like housing 246 of IMD 234, housing 262 contains a control module 268 which provides substantially the same functionality as discussed above with reference to control module 268 of IMD 234 and FIGS. 14A and 14B. Housing 262 also contains battery 272 and coil 270 substantially similar to battery 256 and coil 254 discussed above with reference to IMD 234. In general, housing 262 may be substantially in most respects housing 246 described above with reference to IMD 234 and FIGS. 14A and 14B.

However, as illustrated in FIG. 15B, housing 262 may also comprise a degree of curvature, or angle, to conform to tissues at an implantation site for IMD 260. Housing 262 may be formed with the angle or degree of curvature. In other cases, a clinician may bend housing 262 to a degree of curvature appropriate for a specific stimulation site. For example, housing 262 may comprise a flexible material or include bellows that allow housing 262 to bend. In other embodiments, housing 262 may include a hinge that may rotate to allow the housing to change its curvature. The hinge may include a screw or other limiting mechanism to set the hinge to a desired degree of curvature.

In the example of FIGS. 15A and 15B, housing 262 is defines an angle (A) at a boundary 264 between a portion of the housing containing control module 268 and a portion containing battery 272. The angle (A) may be approximately 20 to 40 degrees, and more preferably approximately 30 degrees. Boundary 264 is illustrated in FIG. 15B as defining a sharp transition, but include a rounded curvature in other embodiments. Further, although a single boundary and angle are illustrated, IMDs according to the invention may include multiple boundaries and angles.

As illustrated in FIG. 15A, control module 268 comprises an application specific integrated circuit, e.g., IC 268, designed to minimize the number of components within IMD 260. IC 268 may be designed using the 0.8 micron process in an effort to reduce the overall size and profile of IMD 260.

With sufficient processing power, IC 268 may have a footprint of approximately 5.2 mm (0.204 inches) by 5.2 mm and a thickness of approximately 0.46 mm (0.018 inches).

IC 268 may be application specific to minimize the components needed by the IC for operation. The ASIC may include both a battery recharge module and a telemetry module that couple to coil 254, as well as a pulse generator and processor. The processor directs the pulse generator to drive one or more electrodes based on stimulation programs stored in memory accessible by the control module 268 or received by the telemetry module. A power management module coupled to battery 272 powers the control circuitry and pulse generator within control module 268.

Figure 16:
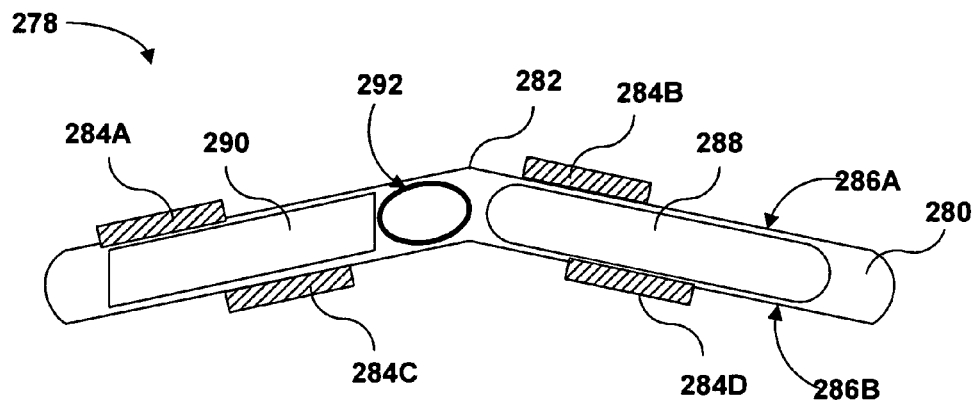
FIG. 16 is a schematic diagram illustrating a side cross-section view of another example implantable medical device with electrodes located on multiple housing surfaces and in which the housing includes a bend.

FIG. 16 is a schematic diagram illustrating a side cross-section view of another example implantable medical device 278 with electrodes located on multiple housing surfaces and in which the housing includes a bend. As shown in FIG. 16, IMD 278 includes a housing 280 with a top surface 286A and a bottom surface 286B, electrodes 284A and 284B located on top surface 286A, and electrodes 284C and 284D located on bottom surface 286B. Electrodes 284A-D (collectively "electrodes 284") may be substantially similar to electrodes 252 discussed above, and arranged on surfaces 286A and 286B (collectively "housing surfaces 286") in substantially the same manner as discussed above with reference to electrodes 252. Further, IMD 278 includes a control module 290, battery 288 and coil 292 within housing 280, which may be substantially similar to and provide substantially the same functionality as any of the control modules, batteries and coils discussed above. Additionally, like housing 262 discussed above with reference to FIGS. 15A and 15B, housing 280 defines an angle at a boundary 282, which may be substantially similar to angle (A) discussed above with reference to housing 262.

However, unlike coils 254 and 270 of IMDs 234 and 260, coil 292 of IMD 278 does not substantially surround control module 290. Instead, coil 292 is located between battery 288 and control module 290, proximate to the boundary at which housing 280 is angled. Again, in various embodiments, a coil may substantially surround a control module, battery, both the control module and the battery, or, as illustrated in FIG. 16, neither the control module nor the battery.

Figure 17:
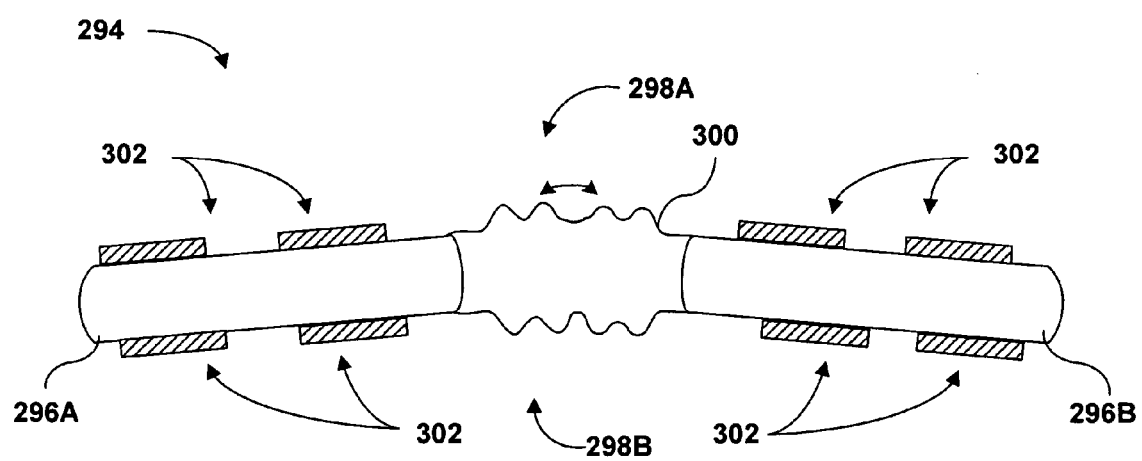
FIG. 17 is a schematic diagram illustrating a side cross-section view of another example implantable medical device with electrodes located on multiple housing surfaces, in which the housing includes a bellows that allows the housing to conform to an implant site.

FIG. 17 is a schematic diagram illustrating a side cross-section view of another example implantable medical device with electrodes located on multiple housing surfaces, in which the housing includes a bellows that allows the housing to conform to an implant site. As shown in FIG. 17, IMD 294 includes first housing 296A, second housing 296B, electrodes 302 located on two surfaces 298A and 298B, and bellows-like joint 300. IMD 294 is substantially similar to IMD 278 of FIG. 16. However, bellows-like joint 300, i.e., bellows 300, allows first and second housings 296 to change position to allow an IMD 294 to bend according to tissue at the implant site of the patient.

Figure 18:
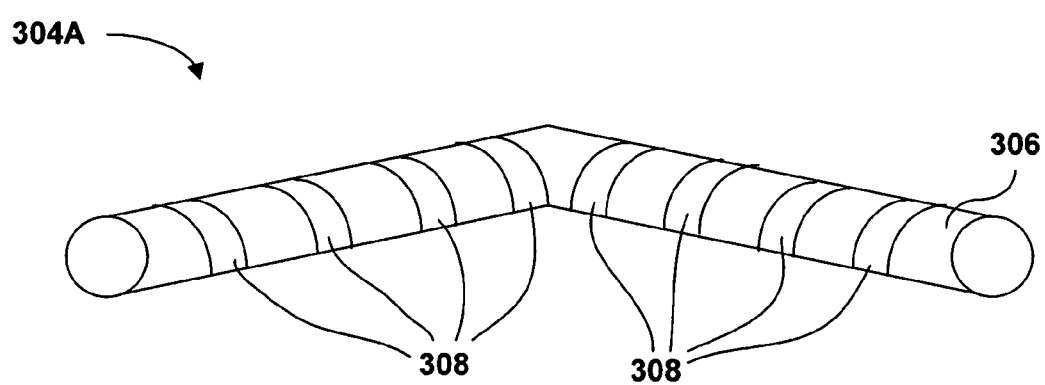
FIG. 18 is a schematic diagram illustrating a side view of an example implantable medical device with ring electrodes located along a bent cylindrical housing.

FIG. 18 is a schematic diagram illustrating a side view of an example implantable medical device with electrodes located along a bent cylindrical housing. FIG. 18 illustrates another IMD 304A. IMD 304A may substantially conform to the IMDs shown in FIGS. 12-17. For example, IMD 304A can be subcutaneously implanted at a stimulation site adjacent a neuralgic region of the patient. IMD 304A comprises a housing 306 that houses a control module, a battery, and a coil (all not shown).

IMD 304A also includes two or more electrodes 308 to provide stimulation to the neuralgic region of the patient. The array of electrodes may be integrated on housing 306 of IMD 304A. Electrodes 308 may be ring electrodes, as illustrated in FIG. 18, or may be discrete pad electrodes distributed at various circumferential positions around IMD 304A.

Housing 306 conforms to a substantially cylindrical form factor. Housing 306 may conform to a miniaturized form factor with a small diameter in order to fit directly adjacent the painful region of the patient. Housing 306 may also comprise a degree of curvature to conform to a radius of the stimulation site.

Housing 306 may be pre-formed with a degree of curvature. As illustrated in FIG. 18, housing 306 has a joint somewhere along the length of the housing. In some embodiments, housing 306 may permit the physician to bend the housing to a degree of curvature appropriate for a specific stimulation site. For example, housing 306 may comprise a flexible material or include bellows, illustrated in FIGS. 19 and 20, that allow housing 306 to bend.

Figure 19:
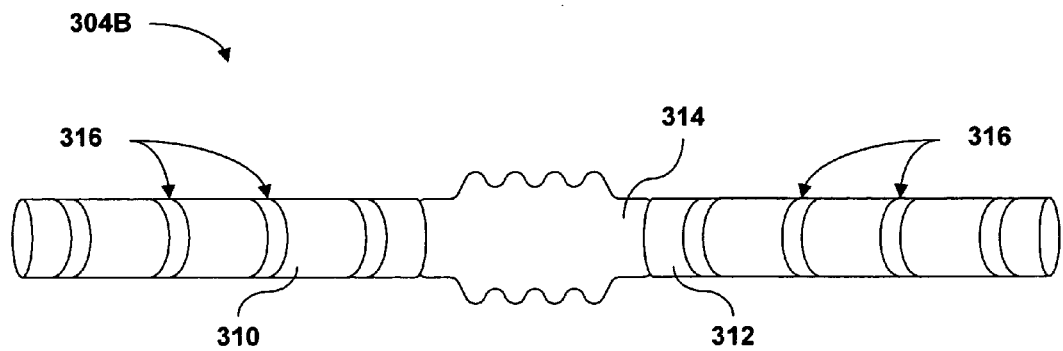
FIGS. 19 and 20 are schematic diagrams illustrating side views of a cylindrical implantable medical device that is flexible at a bellows joint.
Figure 20:
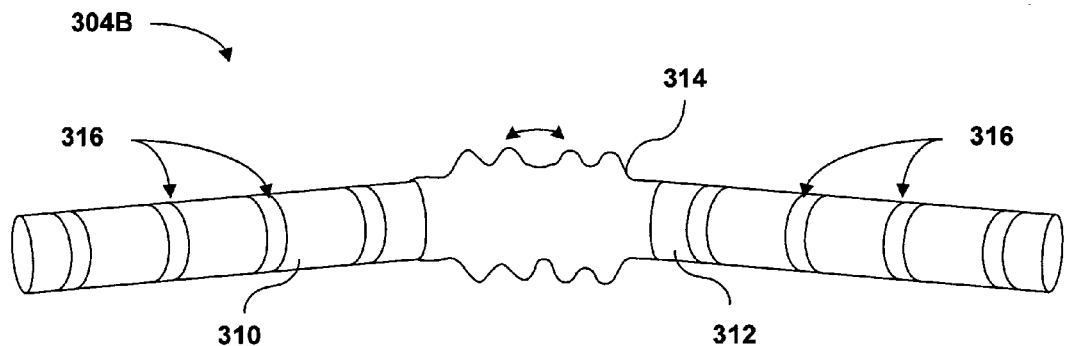

FIGS. 19 and 20 are schematic diagrams illustrating side views of a cylindrical implantable medical device that is flexible at a bellows joint. FIG. 19 is a schematic diagram illustrating an IMD 304B in accordance with another embodiment of the invention. IMD 304B is substantially similar to IMD 304A of FIG. 18. IMD 304B comprises a first housing portion 310 and a second housing portion 312. First and second housing portions 310 and 312 are connected by a bellows-like joint 314. IMD 304B includes an array of ring electrodes 316 integrated along first housing portion 310 and second housing portion 312. First and second housing portions 310 and 312 may be formed from a variety of materials such as titanium, stainless steel, ceramic material, silicone, polyurethane or other polymeric materials.

Each of electrodes 316 is coupled to a control module (not shown) within IMD 304B. The physician may implant IMD 304B at the selected stimulation site with the array of electrodes 316 within the painful region of the patient. First and second housing portions 310 and 312 may conform to a substantially miniaturized form factor and a small diameter to fit within the stimulation site.

As illustrated in FIG. 19, IMD 304B includes bellows-like joint 314 that allows bending of IMD 304B. FIG. 20 is a schematic diagram illustrating IMD 304 in a slightly bent position to better conform to an implantation site. For example, the physician may bend IMD 304B about bellows-like joint 314 to a degree of curvature that conforms to a radius of the specific stimulation site. Bellows-like joint 314 may comprise titanium, nitinol, or another biocompatible material strong enough to withstand flexing. Bellows-like joint 314 may be substantially smaller relative to IMD 304B if the material of bellows 314 is able to withstand the increased flexing force.

Figure 21A:
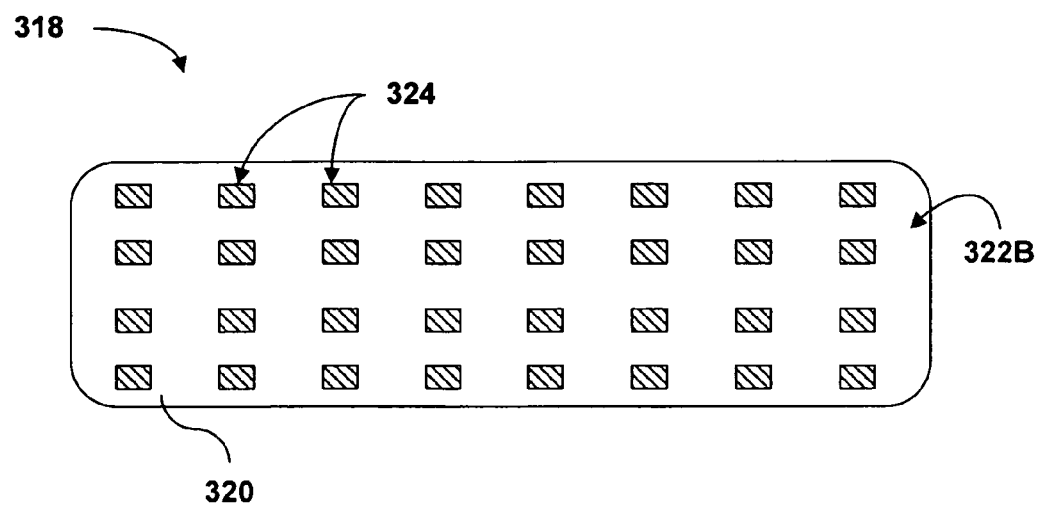
FIGS. 21A and 21B are schematic diagrams respectively illustrating a bottom view and a side cross-sectional view of another example implantable medical device with electrodes located on multiple housing surfaces, in which the top and bottom housing surfaces are respectively convex and concave.
Figure 21B:
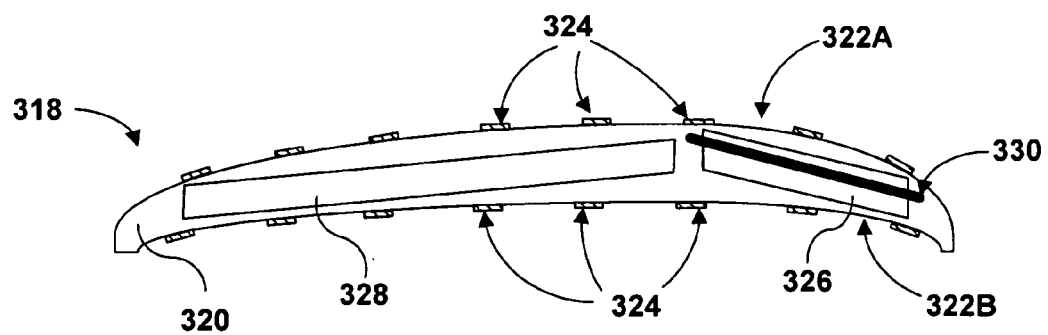

FIGS. 21A and 21B are schematic diagrams illustrating a bottom view and side cross-sectional view, respectively, of another example IMD 318. IMD 318 comprises a housing 320 with a top surface 322A and a bottom surface 322B, each of which includes a two-dimensional array of electrodes 324. As illustrated in FIG. 21A, the two-dimensional arrays of electrodes may cover substantially the entire surface areas of housing surfaces 322A and 322B.

Similar to the other embodiments described above, IMD 318 includes a control module 326, battery 328 and coil 330 within housing 320. Each of electrodes 324 may be coupled to control module 326. Control module 328 may include stimulation generation circuitry to deliver stimulation according to a stimulation program via a combination of electrodes 326 specified by the program. The combination of electrodes may be, for example, a bipolar pair of electrodes on one or both of housing surfaces 322A and 322B.

Control module 326 within IMD 318 can be programmed to apply stimulation via selected combinations of electrodes 324 to achieve desired efficacy. In particular, at the time of implantation, a clinician may test different programs and their associated electrode combinations, and then program IMD 318 with one of more of tested programs. As mentioned previously, programming of IMD 318 may take place through communication of control module 326 with programmers 240, 242 by wireless telemetry via coil 330.

As discussed above, an IMD housing may define an angle between portions of the housing, thereby promoting conformance to the stimulation site. In other embodiments, a housing may have a general curvature instead of localized angle to promote conformance to the stimulation site. For example, top surface 322A and bottom surface 322B of housing 320 illustrated in FIG. 211B respectively are convex and concave. The curvature of the surfaces 322A and 322B of housing 320 may have a radius between 10 centimeters (cm) and 100 cm, according to the dimensions of the implant site.

Figure 22:
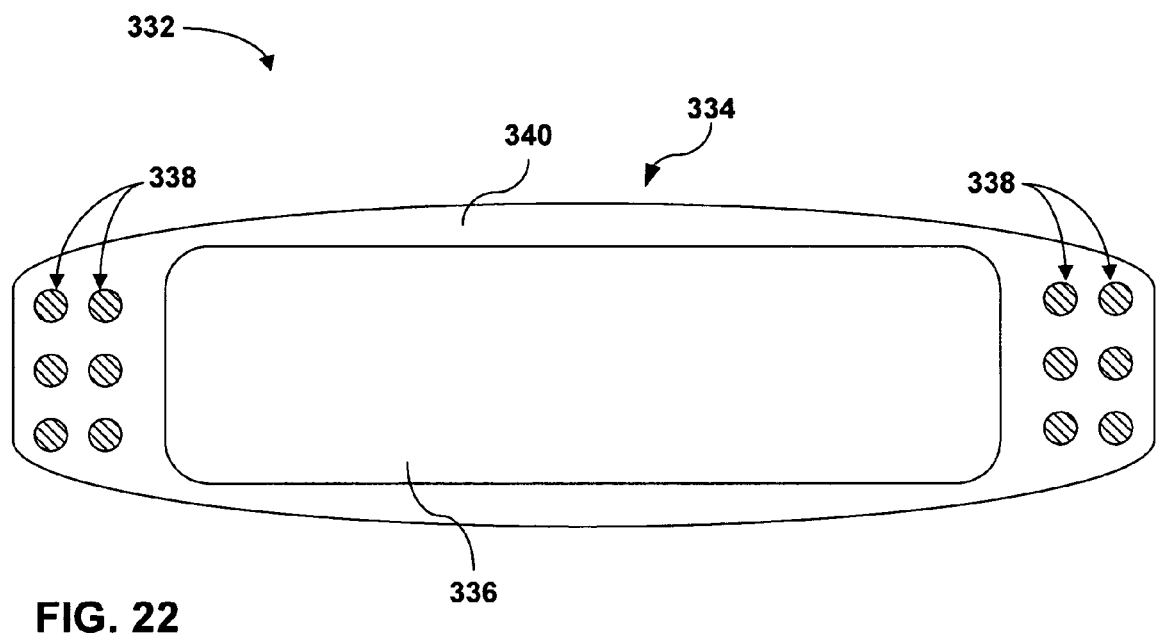
FIG. 22 is a schematic diagram illustrating a bottom view of another example implantable medical device with electrodes located on multiple housing surfaces, in which the housing includes relatively rigid and relatively flexible portions.

FIG. 22 is a schematic diagram illustrating a bottom view of another example IMD 332 in accordance with an embodiment of the invention. IMD 332 comprises a housing 334 that includes a rigid portion 336 and a flexible member 340, such as an overmold, that at least partially encapsulates rigid portion 336. IMD 332 also includes an array of electrodes 338 integrated on flexible member 340 at opposing ends of a bottom surface of housing 334. Each of electrodes 338 may be coupled to a control module (not shown in FIG. 22) within rigid portion 336. At least a portion of each of electrodes 338 protrudes through flexible member 340 for contact with one or more tissues within a patient.

While FIG. 22 illustrates electrodes 338 on the bottom surface 82 and flexible member 340, other embodiments of IMD 332 includes electrodes 338 disposed on one or more other surfaces of housing 334, such as a top surface. Further, IMD 332 may include electrodes 338 on rigid portion 336 instead of or in addition to the flexible member. FIG. 22 also illustrates electrodes 338 grouped into clusters at the ends of surface 340, rather than extending across substantially the entire length or across substantially the entire area of surface 340.

Rigid portion 336 of housing 334 may be formed of any of the rigid housing materials discussed above, such as titanium or stainless steel. Rigid portion 336 may be hermetic and house a control module and battery (not shown). A coil (not shown) for IMD 332 may be located within rigid portion 336 or flexible member 340. Locating the coil within flexible member 340 may improve the communication and energy transfer characteristics of coil by avoiding communication and energy transfer though rigid portion 336. The coil may, for example, substantially encircle rigid portion 334.

Flexible member 340 may comprise a substantially flexible polymer with tapered edges. Flexible member 340 may increase the area of top and bottom housing surfaces without significantly increasing the overall thickness of housing 334. In this way, flexible member 340 may allow more flexibility in the placement of electrodes 338 than integrating the electrodes into a rigid housing alone. Furthermore, flexible member 340 may provide a relatively smooth transition from rigid portion 336 to the tissue surrounding IMD 332. Although IMD 332 has a larger volume than an IMD without a flexible member, e.g., IMD 332, flexible member 340 may improve cosmesis and prevent erosion of the epidermal region adjacent the implantation site of IMD 332.

Figure 23:
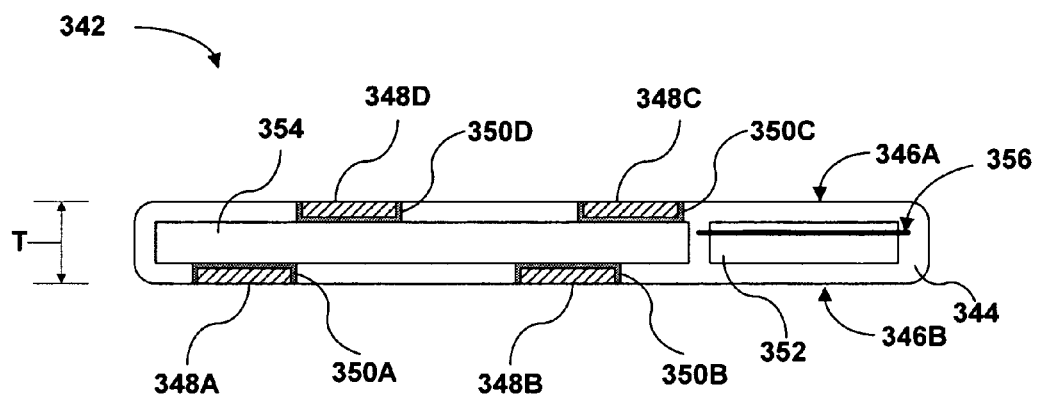
FIG. 23 is schematic diagram illustrating a side cross-sectional view of another example implantable medical device with electrodes located on multiple housing surfaces, in which the electrodes are recessed into the housing surfaces.

FIG. 23 is schematic diagram illustrating a side cross-sectional view of another example implantable medical device with electrodes located on multiple housing surfaces, in which the electrodes are recessed into the housing surfaces. Electrodes have generally been illustrated herein as being raised from the exterior surface of an IMD housing, such that the electrodes and the housing surface are not flush. However, it may be beneficial to utilize electrodes that have a small thickness to limit the extension of the electrodes into the surrounding tissue area. Further, electrodes 338 may be recessed slightly into the IMD housing to reduce the thickness of the housing.

For example, FIG. 23 is schematic diagram illustrating a side cross-sectional view of another example IMD 342 with recessed electrodes. As shown in FIG. 23, IMD 342 includes housing 344 with first and second surfaces 346A and 346B, a control module 352, coil 356, battery 354, and electrodes 348A, 348B, 348C and 348D (collectively "electrodes 348") located on first and second surfaces 346A and 346B. IMD 342 and these components may be significantly similar to the other IMDs and components described herein. However, electrodes 348 are recessed within housing 344 such that an exterior surface of each electrode is substantially flush with one of surfaces 346A and 356B. The recessing of electrodes 348 within housing 344 may reduce the thickness (T) of IMD 342 relative to the thickness (T) of, for example, IMD 244 depicted in FIG. 14B.

In order to accommodate electrodes 348, housing 344 may include insulation 350A-D disposed around each of electrodes 348 to electrically separate each electrode from the housing. Insulation 350A-D prevents electric current from being conducted through or along the surface of housing 344, or otherwise effecting the operation of IMD 342. Insulation 350 may be constructed of any material that does not conduct electricity, e.g., rubber, plastic, or composite materials.

Figure 24:
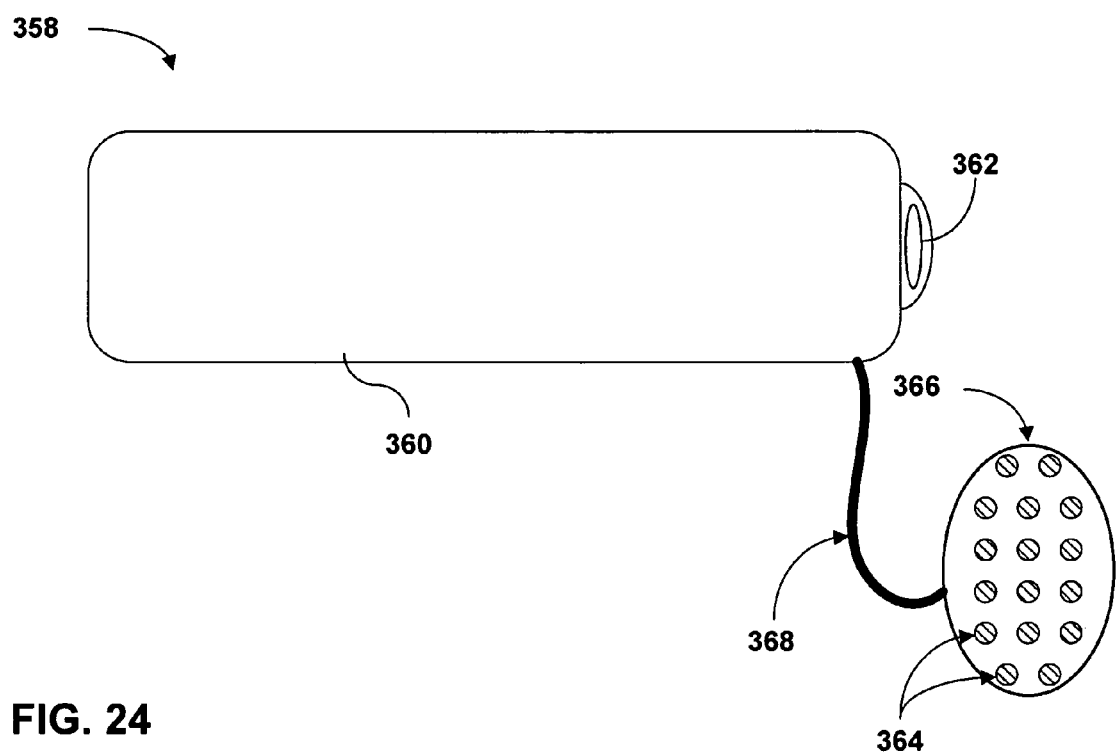
FIG. 24 is schematic diagram illustrating another example implantable medical device coupled to an additional array of electrodes.

FIG. 24 is a schematic diagram illustrating a bottom view of another example IMD 358 in accordance with an embodiment of the invention. IMD 358 comprises a housing 360, and may include electrodes (not shown) on multiple surfaces of the housing, similar to the other IMDs described above. IMD 358 may also include a control module, battery and coil, the other IMDs described above. However, like the IMDs described above, housing 360 includes an attachment mechanism 362 allows a clinician or physician to secure IMD 358 within a tissue region with suture, staples, or another securing device. In some embodiments, attachment mechanism 362 may be a self-deploying or passive fixation element that protrudes from housing 360 to engage tissue, such as hooks, barbs, screws, expandable stent-like elements, or expandable hydrogel elements.

IMD 358 further includes a separate member 366 coupled to IMD 358 via a lead 368. Member 366 may support an array of electrodes 364 on one or more of its surfaces. In this manner, IMD 358 may be capable of providing PNFS or other types of electrical stimulation to two or more tissue areas that cannot simultaneously be directly contacted by housing 360. Further, separate member 366 may be able to be tunneled to a tissue area that is not reachable through direct implantation of IMD 358 or too small to accommodate the IMD.

Figure 25:
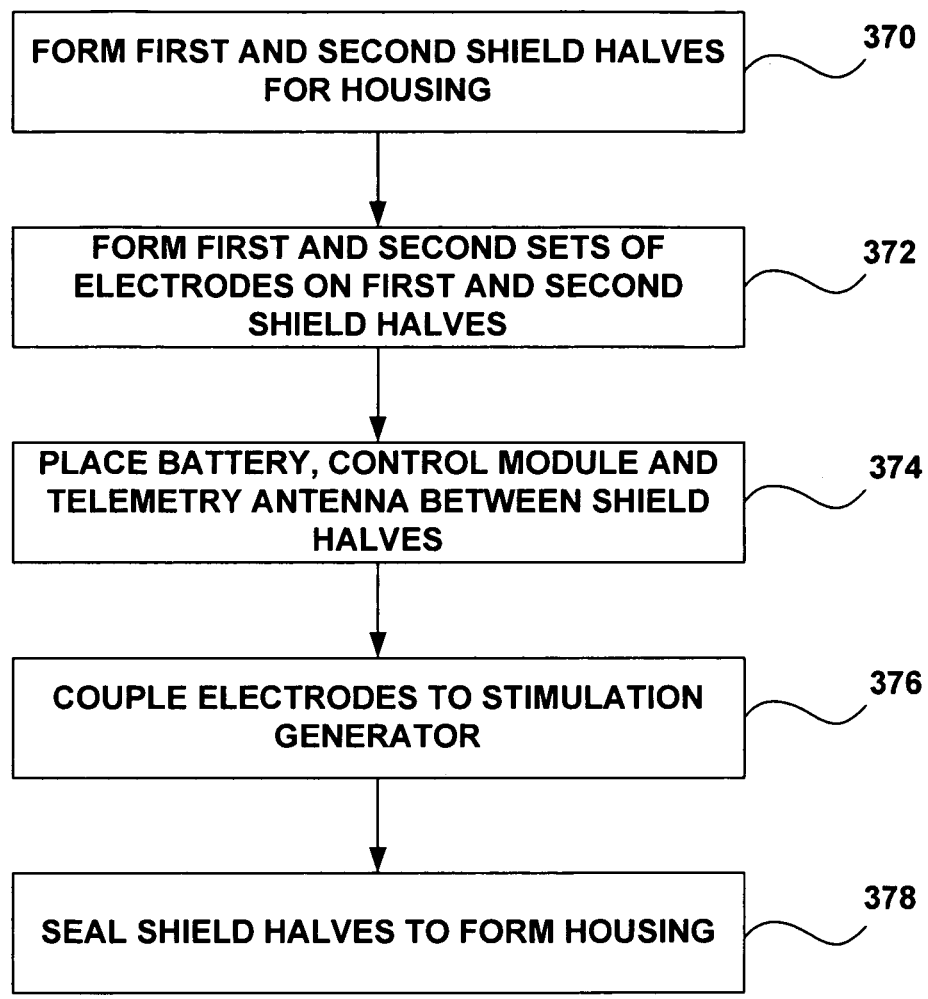
FIG. 25 is a flow diagram illustrating an example method of manufacturing an implantable medical device with electrodes located on multiple housing surfaces.

FIG. 25 is a flow diagram illustrating an example method of manufacturing an implantable medical device with electrodes located on multiple housing surfaces. According to the example method, first and second shield halves, e.g., shallow drawn titanium shield halves, are formed (370). The shield halves respectively include a top or bottom surface for the IMD housing, and may be formed to be concave or convex, or to have an angle, as described above.

First and second sets of electrodes are located on the respective surfaces provided by the shield halves (372). The electrodes may be welded or otherwise attached to the shield halves, or formed thereon by any process, e.g., a deposition process. Locating electrodes on the shield halves may include forming feedthroughs and then adding them through the shield halves for each of the electrodes, forming recess for the each of the electrodes in the shield halves, and placing insulative material on the shield halves for each of the electrodes, e.g., within the recesses.

A battery, control module and coil for the IMD may be placed between the shield halves (374). The electrodes, and more particularly the feedthrough conductors coupled to the electrodes, may be coupled to a stimulation generator, which may be provided by the control module (376). Coupling of the feedthrough conductors may be accomplished by welding or bonding. In some embodiments, a flex-tape circuit may be used to couple the feedthrough conductors to the control module. Insulation may be placed between the shield halves, which may then be hermetically sealed to form the housing for the IMD, e.g., by welding or brazing (378).

Figure 26:
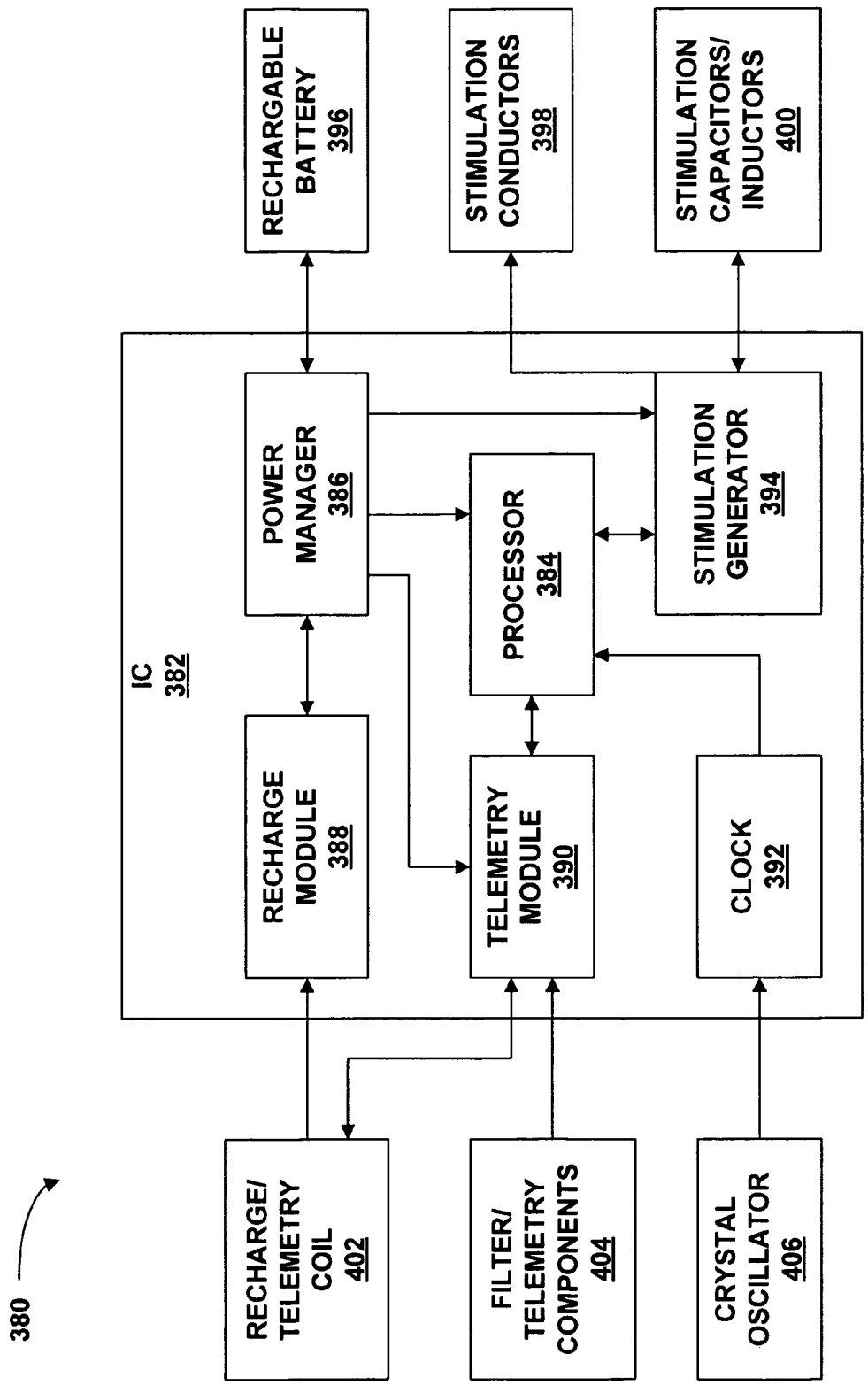
FIG. 26 is a block diagram illustrating an example control module for an implantable medical device.

FIG. 26 is a block diagram illustrating an example control module 380 included in an IMD, which may correspond to control module 266 of IMD 260 depicted in FIGS. 15A and 15B, or any of the other control modules discussed above. Control module 380 comprises an IC 382, stimulation capacitors and inductors 400, filter and telemetry components 404, and a crystal oscillator 406 positioned on a substrate board. The substrate board may comprise a minimal number of layers, e.g. four layers or less, and comprise a thickness equal to or less than approximately 0.4 mm (0.014 inches). Control module 380 is also coupled to a rechargeable battery 396, stimulation conductors 398 that connect to one or more stimulation electrodes of the IMD, and a recharge and telemetry coil 402.

IC 382 may be formed as an ASIC designed to minimize the number of components within the IMD. IC 382 may be designed using the 0.8 micron process in an effort to reduce the overall size and profile of the IMD. IC 382 may operate substantially similar to IC 268 of control module 266 (FIG. 15A). IC 382 includes a processor 384, a power manager 386, a recharge module 388, a telemetry module 390, a stimulation generator 394, and a clock 392.

Power manager 386 couples to rechargeable battery 396 to provide power to processor 384, recharge module 388, telemetry module 390, and pulse generator 394. Recharge module 388 couples to recharge and telemetry coil 402 and receives power via the coil to recharge battery 396. Telemetry module 390 also couples to recharge and telemetry coil 402 and receives stimulation programs and other instructions from a programmer operated by the patient or physician via coil 402. Filter components 404, power manager 386, and telemetry components 404 couple to telemetry module 390 to support reliable wireless communication. Filter and telemetry components 404 may be selected from Table 4 below.

TABLE 4

| Component | Characteristics |
|---|---|
| BPLUS Filter | 1 uF |
| VREG Filter | 0.1 uF |
| VDD Filter | 0.1 uF |
| Battery Bypass | 0.1 uF |
| Shottky Diode | — |
| Telemetry Tank Cap | 1500 pF |

Examples of filter, power management and telemetry components include a telemetry tank capacitor, voltage regulation filters, power supply filters, and battery bypass capacitors. Telemetry module 390 provides stimulation programs and other information received from programmers 240, 242 to processor 384, which stores the programs in a memory (not shown). As discussed above with reference to FIGS. 14A and 14B, the memory may also store program instructions that, when executed by processor 384, cause processor 384 to provide the functionality generally ascribed to processors, control modules and IMDs herein.

Crystal oscillator 406 is coupled to clock 392, which clocks processor 384 to run the stimulation programs. Processor 384 directs stimulation generator 394 to provide stimulation to the electrodes of the IMD via stimulation conductors 398. Processor 384 directs stimulation generator 394 according to the stimulation programs received from telemetry module 390 and/or stored in memory, and the clock cycle received from clock 392. In some embodiments, the memory may stored a plurality of programs, and processor 384 may select one or more programs from the plurality based on a schedule stored in memory or a signal received from a programmer 240, 242 via coil 402 and telemetry module 390.

As discussed above, each program may specify stimulation via a combination of electrodes that includes electrodes on a single surface of an IMD housing, or multiple surfaces of the IMD housing. Accordingly, respective programs may be tailored for stimulation of respective tissues or tissue layers via electrodes in respective locations or on respective surfaces, or a program may simultaneously stimulate multiple tissues and tissue layers. In some embodiments, processor 384 may control stimulation generator 394 to deliver stimulation according to a group of programs, each program including a respective electrode configuration involving one or more housing surfaces. Stimulation generator 394 may alternate delivery of stimulation according to the respective programs of the program group, e.g., may deliver each pulse according to a different one of the program, such that the patient cannot perceive transitions between the different programs. The memory of control module 380, which may be on or off IC 382, may store program groups received from programmers 240, 242, and processor 384 may select a program group, in the manner described above.

Stimulation generator 394 may be a voltage or current pulse generator, and may be coupled to stimulation capacitors and inductors 400, which include capacitors to store energy for stimulation pulses. Stimulation generator 394 may control a switching matrix (not shown) to couple stimulation capacitors and inductors 400 to selected electrodes via their corresponding stimulation conductors 398, as directed by a stimulation program. Stimulation capacitors and inductors 400 may contain components provided from Table 5.

TABLE 5

| Component | Characteristics |
|---|---|
| Stimulation Cap | 10 uF/20 V |
| Series Stimulation Cap | 10 uF/6 V |
| Bypass Cap | 47 uF/6 V |
| Inductor | 560 uH |

In some embodiments, control module 380 may include more or less components as needed by the IMD containing the control module. For example, multiple memories may be utilized in control module 380. One memory may be used to store operational protocols, one memory may be used to save any error data, and another memory may store stimulation programs for treating the patient. Control module 380 may be configured to conserve energy whenever possible.

Various embodiments of the invention have been described. However, one of ordinary skill in the art will appreciate that various modifications may be made to the described embodiments without departing from the scope of the invention. These and other embodiments are within the scope of the following claims.

The invention claimed is:

1. A method for treating pain of a patient comprising:
   delivering peripheral nerve field stimulation to a region of a body of the patient in which a patient experiences pain via at least one electrode implanted in the region; and
   delivering spinal cord stimulation to the patient via at least one electrode implanted in an epidural space of the patient in combination with the peripheral nerve field stimulation.

2. The method of claim 1, wherein delivering peripheral nerve field stimulation via at least one electrode implanted in the region comprises delivering peripheral nerve field stimulation via at least one electrode implanted within or between at least one of an intra-dermal, deep dermal, or subcutaneous layer of the region.

3. The method of claim 1, wherein delivering peripheral nerve field stimulation and spinal cord stimulation comprises delivering the peripheral nerve field stimulation and the spinal cord stimulation from a single implantable medical device.

4. The method of claim 1, wherein delivering peripheral nerve field stimulation and spinal cord stimulation comprises delivering the peripheral nerve field stimulation and the spinal cord stimulation simultaneously.

5. The method of claim 1, wherein delivering peripheral nerve field stimulation and spinal cord stimulation comprises alternating delivery of the peripheral nerve field stimulation and the spinal cord stimulation.

6. The method of claim 1, wherein delivering the spinal cord stimulation in combination with the peripheral nerve field stimulation comprises delivering the spinal cord stimulation and the peripheral nerve field stimulation according to at least one of different stimulation parameters or different duty cycles.

7. The method of claim 1, wherein delivering the spinal cord stimulation in combination with the peripheral nerve field stimulation comprises:
   delivering the spinal cord stimulation and the peripheral nerve field stimulation according to different programs within a group that includes a plurality of programs; and
   delivering each successive stimulation pulse from an implantable medical device according to a different one of the programs.

8. The method of claim 1, wherein delivering peripheral nerve field stimulation to a region of a body of the patient in which a patient experiences pain comprises delivering peripheral nerve field stimulation to an axial region of a back of the patient.

9. A method for treating pain of a patient comprising:
   delivering peripheral nerve field stimulation to a region of a body of the patient in which a patient experiences pain via at least one electrode implanted in the region; and
   delivering at least one therapeutic agent to the patient intrathecally in combination with the peripheral nerve field stimulation.

10. The method of claim 9, wherein delivering at least one therapeutic agent comprises delivering at least one of an opioid, cannabinoid, local anesthetic, baclofen, adenosine, alpha blocker, anti-inflammatory, steroid, muscle relaxant, antidepressant, or antiepileptic.

11. A system for treating pain of a patient comprising:
    at least one electrode implanted in a region of the body of the patient in which a patient experiences pain;
    at least one electrode implanted in an epidural space of the body of the patient;
    means for delivering peripheral nerve field stimulation via the at least one electrode implanted in the region of the body of the patient in which the patient experiences pain; and
    means for delivering spinal cord stimulation to the patient via the at least one electrode implanted in the epidural space of the body of the patient.

12. The system of claim 11, wherein the at least one electrode implanted in the region of the body of the patient in which the patient experiences pain is implanted within or between at least one of an intra-dermal, deep dermal, or subcutaneous layer of the region.

13. The system of claim 11, wherein the means for delivering peripheral nerve field stimulation and the means for delivering spinal cord stimulation comprise means for delivering the peripheral nerve field stimulation and the spinal cord stimulation simultaneously.

14. The system of claim 11, wherein the means for delivering peripheral nerve field stimulation and the means for delivering spinal cord stimulation comprise means for alternating delivery of the peripheral nerve field stimulation and the spinal cord stimulation.

15. The system of claim 11, wherein the means for delivering peripheral nerve field stimulation and the means for delivering spinal cord stimulation comprise means for delivering the peripheral nerve field stimulation and the spinal cord stimulation according to a least one of different stimulation parameters or duty cycles.

16. The system of claim 11, wherein the at least one electrode implanted in the region of the body of the patient in which the patient experiences pain comprises at least one electrode implanted in an axial region of a back of the patient.

17. A system for treating pain of a patient comprising:
    at least one electrode implanted in a region of a body of the patient in which a patient experiences pain;
    means for delivering peripheral nerve field stimulation via the at least one electrode; and
    means for delivering at least one therapeutic agent to the patient intrathecally in combination with the peripheral nerve field stimulation.

18. The system of claim 17, wherein the means for delivering at least one therapeutic agent comprises means for delivering at least one of an opioid, cannabinoid, local anesthetic, baclofen, adenosine, alpha blocker, anti-inflammatory, steroid, muscle relaxant, antidepressant, or antiepileptic.

19. A system for treating pain of a patient comprising:
    a first set of one or more electrodes implanted in a first region of a body of the patient in which the patient experiences pain;
    a second set of one or more electrodes implanted in an epidural space of the patient; and
    an implantable medical device coupled to the first and second sets of electrodes that delivers peripheral nerve field stimulation via the first set of electrodes and spinal cord stimulation via the second set of a electrodes.

20. The system of claim 19, wherein the first set of electrodes is implanted in an axial region of a back of the patient.

21. The system of claim 19, wherein the implantable medical device delivers the peripheral nerve field stimulation and the spinal cord stimulation simultaneously.

22. The system of claim 19, wherein the implantable medical device alternates delivery of the peripheral nerve field stimulation and the spinal cord stimulation.

23. The system of claim 19, wherein the implantable medical device selectively delivers at least one of the peripheral nerve field stimulation or the spinal cord stimulation based on at least one of a command received from a patient or a schedule.

24. The system of claim 19, wherein the implantable medical device delivers the peripheral nerve field stimulation and the spinal cord stimulation according to at least one of different stimulation parameters or duty cycles.

25. The system of claim 19, wherein the implantable medical device delivers stimulation according to a group of programs, the group of programs includes at least one peripheral nerve field stimulation program and at least one spinal cord stimulation program, and the implantable medical device delivers each successive pulse of a plurality of stimulation pulses according to a different one of the programs of the program group.

26. A system for treating pain of a patient comprising:
a first implantable medical device that delivers peripheral nerve field stimulation to a region of a body of the patient in which the patient experiences pain; and
a second medical device that delivers spinal cord stimulation to the patient via at least one electrode implanted in an epidural space of the patient.

27. The system of claim 26, wherein the first and second medical devices communicate to coordinate delivery of the peripheral nerve field stimulation and the spinal cord stimulation.

28. The system of claim 26, wherein the second medical device is implantable.

29. The system of claim 26, wherein the first implantable medical device comprises a housing implantable within the region of the body in which the patient experiences pain and an array of electrodes located on the housing, and delivers the peripheral nerve field stimulation via the electrodes located on the housing.

30. The system of claim 26, wherein the first implantable medical device delivers peripheral nerve field stimulation to an axial region of a back of the patient.

31. A system for treating pain of a patient comprising:
a first implantable medical device that delivers peripheral nerve field stimulation to a region of a body of the patient in which the patient experiences pain; and
a second medical device that delivers at least one therapeutic agent to the patient intrathecally.

* * * * *